US010039571B2

(12) United States Patent
Jackson

(10) Patent No.: US 10,039,571 B2
(45) Date of Patent: *Aug. 7, 2018

(54) BONE ANCHOR RECEIVER WITH TOP LOADED SNAP IN PLACE INSERT

(71) Applicant: Roger P. Jackson, Prairie Village, KS (US)

(72) Inventor: Roger P. Jackson, Prairie Village, KS (US)

(*) Notice: Subject to any disclaimer, the term of this patent is extended or adjusted under 35 U.S.C. 154(b) by 0 days.

This patent is subject to a terminal disclaimer.

(21) Appl. No.: 15/419,740

(22) Filed: Jan. 30, 2017

(65) Prior Publication Data

US 2017/0135731 A1 May 18, 2017

Related U.S. Application Data

(63) Continuation of application No. 14/557,945, filed on Dec. 2, 2014, now Pat. No. 9,662,143, which is a
(Continued)

(51) Int. Cl.
*A61B 17/70* (2006.01)
*A61B 17/86* (2006.01)

(52) U.S. Cl.
CPC ...... *A61B 17/7035* (2013.01); *A61B 17/7032* (2013.01); *A61B 17/864* (2013.01); *A61B 17/8625* (2013.01)

(58) Field of Classification Search
CPC ............ A61B 17/7035; A61B 17/7032; A61B 17/8625; A61B 17/864; A61B 17/701;
(Continued)

(56) References Cited

U.S. PATENT DOCUMENTS 854,956 A 5/1907 Martin
2,243,717 A 5/1941 Godoy et al.
(Continued)

FOREIGN PATENT DOCUMENTS

DE 20207850 10/2002
WO WO 95/013755 5/1995

OTHER PUBLICATIONS

European Search Report, EP14189707.4, dated Feb. 25, 2015.

*Primary Examiner* — Pedro Philogene
(74) *Attorney, Agent, or Firm* — Polsinelli PC

(57) ABSTRACT

A dynamic fixation medical implant includes a longitudinal connecting member assembly having an elongate coil-like outer member and an inner cylindrical core attached to the outer member at only one end thereof. Some assemblies include a second longitudinal connecting member in the form of a rod that is fixed to the inner core and extends outwardly from the assembly. Certain assemblies include a threaded core or threaded inserts that cooperate with a helical slit of the coil-like outer member. Two or more cooperating bone screw assemblies attach to the connecting member assembly. The bone screw assemblies may include upper and lower compression members for affixing to and cradling the coil-like outer member only, allowing relative movement between the outer member and the inner cylindrical core. Press fit or snap-on features attach one end of the coil-like outer member to one end of the inner cylindrical core.

28 Claims, 20 Drawing Sheets

Related U.S. Application Data continuation of application No. 13/815,054, filed on Jan. 28, 2013, now Pat. No. 8,900,272, which is a continuation of application No. 12/804,580, filed on Jul. 23, 2010, now Pat. No. 8,394,133, which is a continuation of application No. 11/522,503, filed on Sep. 14, 2006, now Pat. No. 7,766,915, which is a continuation-in-part of application No. 11/178,854, filed on Jul. 11, 2005, now Pat. No. 7,789,896, and a continuation-in-part of application No. 11/024,543, filed on Dec. 20, 2004, now Pat. No. 7,204,838, and a continuation-in-part of application No. 10/986,377, filed on Nov. 10, 2004, now Pat. No. 7,833,250.

(60) Provisional application No. 60/832,644, filed on Jul. 21, 2006, provisional application No. 60/736,112, filed on Nov. 10, 2005, provisional application No. 60/728,912, filed on Oct. 21, 2005, provisional application No. 60/725,445, filed on Oct. 11, 2005, provisional application No. 60/722,300, filed on Sep. 30, 2005, provisional application No. 60/655,239, filed on Feb. 22, 2005.

(58) Field of Classification Search
CPC ............ A61B 17/7008; A61B 17/7037; A61B 17/7031; A61B 17/7045; A61B 17/705; A61B 17/7082; A61B 17/7091; A61B 17/8605; A61B 2017/681; A61B 2017/567
USPC ............... 606/246–279, 86 A, 300–315, 328
See application file for complete search history.

(56) References Cited

U.S. PATENT DOCUMENTS

| | | |
|---|---|---|
| 2,524,095 A | 10/1950 | Williams |
| 2,531,892 A | 11/1950 | Reese |
| 2,532,972 A | 12/1950 | Vertin |
| 2,579,438 A | 12/1951 | Longfellow |
| 2,669,896 A | 2/1954 | Clough |
| 2,813,450 A | 11/1957 | Dzus |
| 3,013,244 A | 12/1961 | Rudy |
| 3,236,275 A | 2/1966 | Smith |
| 4,269,178 A | 5/1981 | Keene |
| 5,020,519 A | 6/1991 | Hayes |
| D346,217 S | 4/1994 | Sparker |
| 5,443,467 A | 8/1995 | Biedermann et al. |
| 5,961,517 A | 10/1999 | Biedermann et al. |
| 6,077,262 A | 6/2000 | Schlapfer et al. |
| 6,139,549 A | 10/2000 | Keller |
| 6,214,012 B1 | 4/2001 | Karpman et al. |
| 6,273,888 B1 | 8/2001 | Justis |
| 6,280,442 B1 | 8/2001 | Barker et al. |
| 6,287,311 B1 | 9/2001 | Sherman et al. |
| 6,302,888 B1 | 10/2001 | Mellinger et al. |
| 6,440,133 B1 | 8/2002 | Beale et al. |
| 6,530,929 B1 | 3/2003 | Justis et al. |
| 6,540,749 B2 | 4/2003 | Schafer et al. |
| 6,565,565 B1 | 5/2003 | Yuan et al. |
| 6,648,888 B1 | 11/2003 | Shluzas |
| 6,730,089 B2 | 5/2004 | Jackson |
| 6,755,829 B1 | 6/2004 | Bono et al. |
| 6,837,889 B2 | 1/2005 | Shluzas |
| 6,911,030 B1 | 6/2005 | Vanacker et al. |
| 6,932,822 B2 | 8/2005 | Oribe et al. |
| 7,066,937 B2 | 6/2006 | Shluzas |
| 7,087,057 B2 | 8/2006 | Konieczynski et al. |
| 7,090,679 B2 | 8/2006 | Saint-Martin et al. |
| 7,144,396 B2 | 12/2006 | Shluzas |
| 7,160,300 B2 | 1/2007 | Jackson |
| 7,179,261 B2 * | 2/2007 | Sicvol ............... A61B 17/7032 606/86 A |
| 7,250,052 B2 | 7/2007 | Landry et al. |
| 7,377,923 B2 | 5/2008 | Purcell et al. |
| 7,527,638 B2 | 5/2009 | Anderson et al. |
| 7,547,318 B2 | 6/2009 | Birkmeyer et al. |
| 7,618,444 B2 | 11/2009 | Shluzas |
| 7,666,188 B2 | 2/2010 | Anderson et al. |
| 7,686,835 B2 | 3/2010 | Warnick |
| 7,708,763 B2 | 5/2010 | Selover et al. |
| 7,722,651 B2 | 5/2010 | Kwak et al. |
| 7,862,587 B2 | 1/2011 | Jackson |
| 7,951,172 B2 | 5/2011 | Chao et al. |
| 7,985,242 B2 | 7/2011 | Forton et al. |
| 8,034,084 B2 | 10/2011 | Landry et al. |
| 8,043,343 B2 | 10/2011 | Miller et al. |
| 8,066,739 B2 | 11/2011 | Jackson |
| 8,075,592 B2 | 12/2011 | Landry et al. |
| 8,100,915 B2 | 1/2012 | Jackson |
| 8,100,946 B2 | 1/2012 | Strasbaugh et al. |
| 8,162,948 B2 | 4/2012 | Jackson |
| 8,262,704 B2 | 9/2012 | Matthis et al. |
| 8,377,067 B2 | 2/2013 | Jackson |
| 8,894,655 B2 | 11/2014 | Fallin et al. |
| 9,050,148 B2 | 6/2015 | Jackson |
| 9,101,415 B2 | 8/2015 | Jackson |
| 9,173,682 B2 | 11/2015 | Jackson |
| 9,192,413 B2 * | 11/2015 | Biedermann |
| 9,216,039 B2 | 12/2015 | Jackson |
| 9,265,534 B2 | 2/2016 | Jackson |
| 9,265,535 B2 | 2/2016 | Jackson |
| 9,265,536 B2 | 2/2016 | Jackson |
| 9,265,537 B2 | 2/2016 | Jackson |
| 9,271,767 B2 | 3/2016 | Jackson |
| 9,532,815 B2 | 1/2017 | Jackson |
| 9,662,143 B2 * | 5/2017 | Jackson ............. A61B 17/7028 |
| 2002/0026193 A1 | 2/2002 | Barker et al. |
| 2002/0133154 A1 | 9/2002 | Saint-Martin |
| 2002/0143341 A1 * | 10/2002 | Biedermann ....... A61B 17/7032 606/308 |
| 2003/0023240 A1 | 1/2003 | Amrein et al. |
| 2003/0100904 A1 | 5/2003 | Biedermann |
| 2004/0143265 A1 | 7/2004 | Landry et al. |
| 2004/0167525 A1 | 8/2004 | Jackson |
| 2004/0172022 A1 | 9/2004 | Landry et al. |
| 2005/0131408 A1 | 6/2005 | Sicvol et al. |
| 2005/0149036 A1 | 7/2005 | Varieur et al. |
| 2005/0192573 A1 | 9/2005 | Abdelgany et al. |
| 2005/0216003 A1 | 9/2005 | Biedermann et al. |
| 2006/0036252 A1 * | 2/2006 | Baynham ........... A61B 17/7035 606/308 |
| 2006/0079909 A1 | 4/2006 | Runco |
| 2006/0173454 A1 | 8/2006 | Spitler et al. |
| 2006/0247658 A1 | 11/2006 | Pond, Jr. et al. |
| 2006/0293693 A1 | 12/2006 | Farr et al. |
| 2009/0204155 A1 | 8/2009 | Aschmann |
| 2011/0015678 A1 | 1/2011 | Jackson |
| 2012/0071886 A1 | 3/2012 | Jackson |
| 2013/0304130 A1 | 11/2013 | Jackson |
| 2014/0222090 A1 | 8/2014 | Jackson |
| 2015/0080974 A1 | 3/2015 | Jackson |
| 2015/0142060 A1 | 5/2015 | Jackson |
| 2015/0182258 A1 | 7/2015 | Jackson |
| 2015/0265322 A1 | 9/2015 | Jackson |
| 2015/0272631 A1 | 10/2015 | Jackson |
| 2016/0015433 A1 | 1/2016 | Jackson |
| 2016/0074077 A1 | 3/2016 | Jackson |
| 2017/0181775 A1 | 6/2017 | Jackson |
| 2017/0209187 A1 | 7/2017 | Jackson |

* cited by examiner

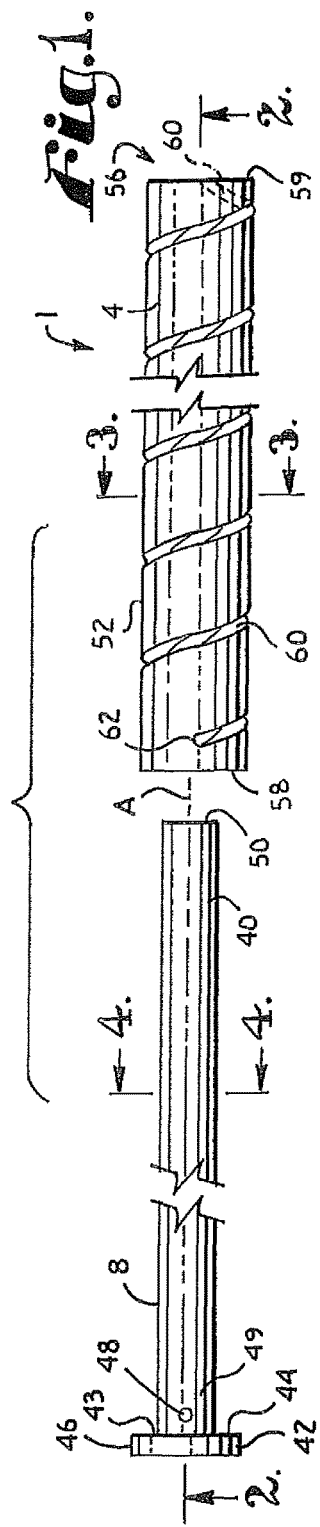
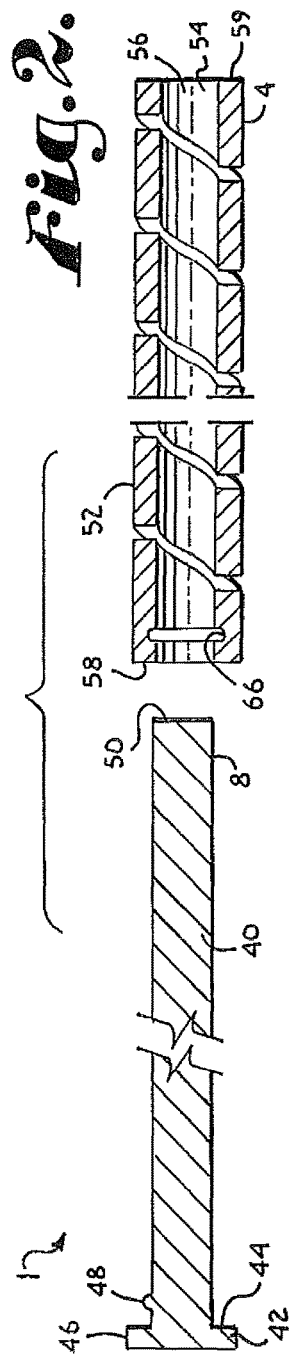
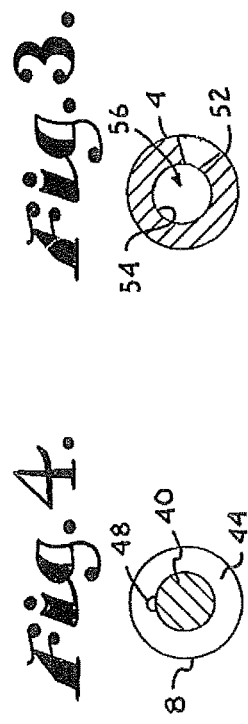
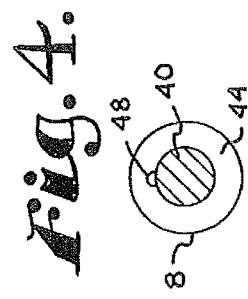

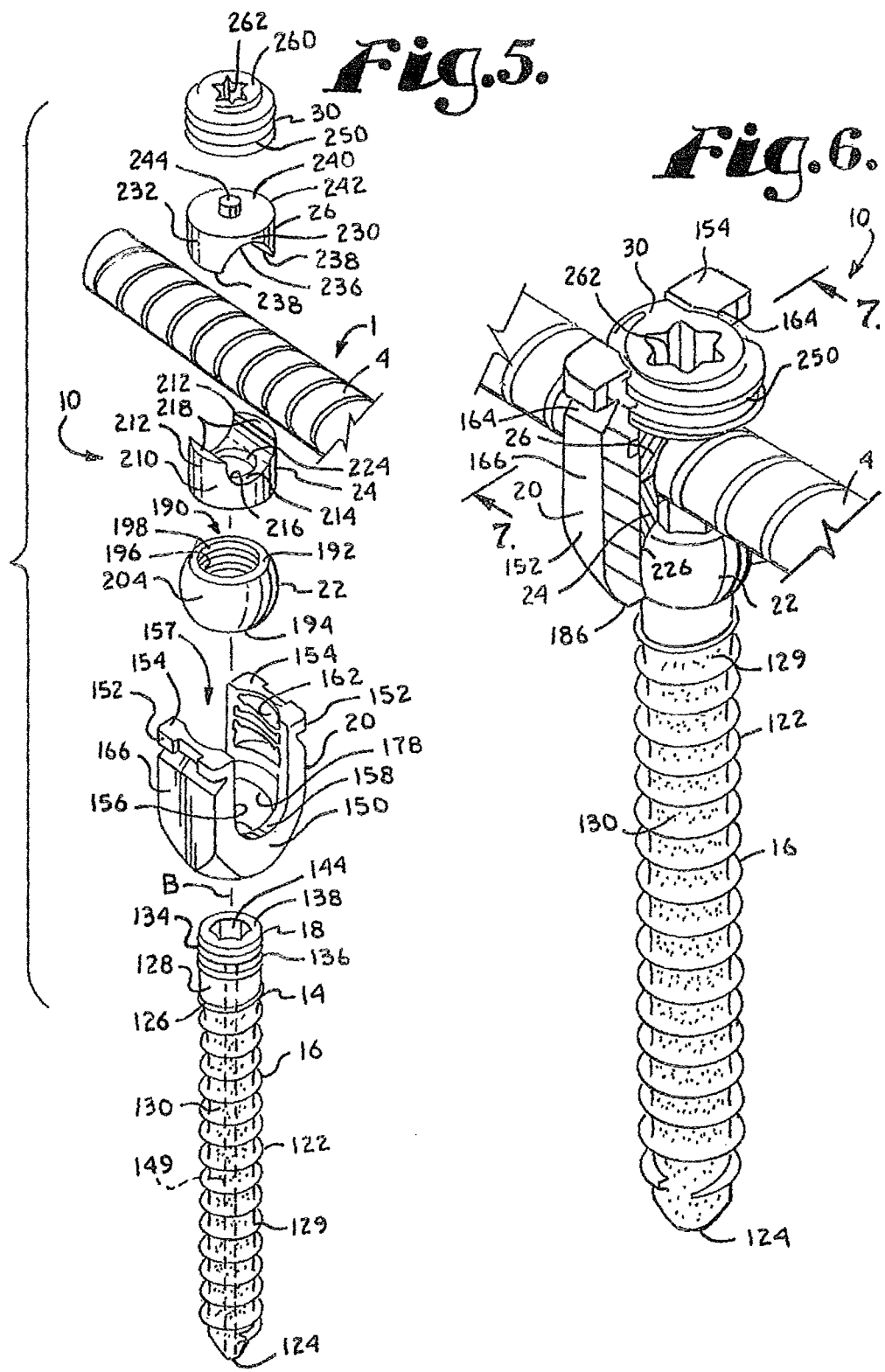

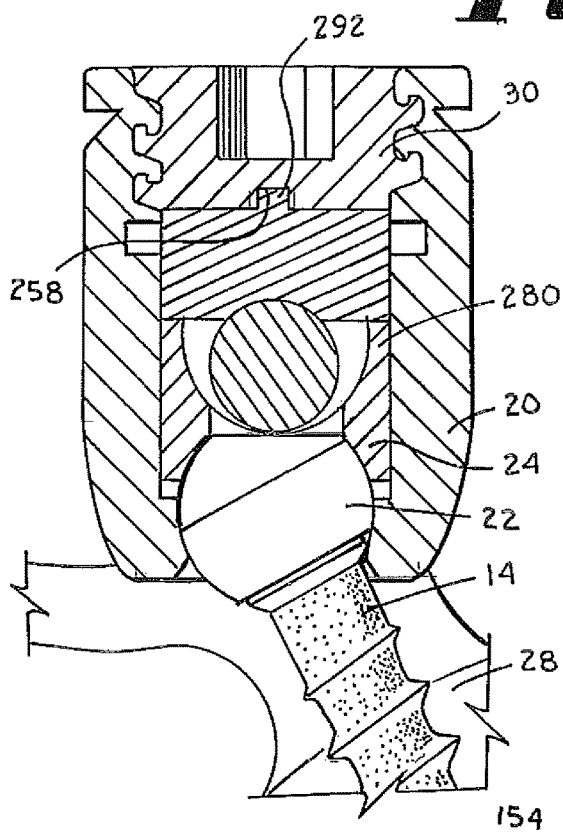

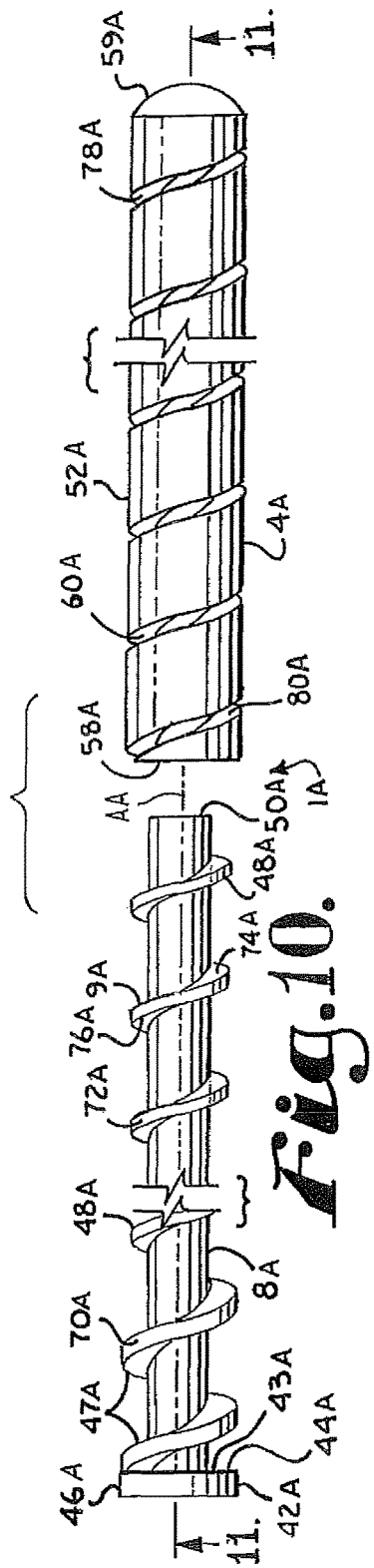
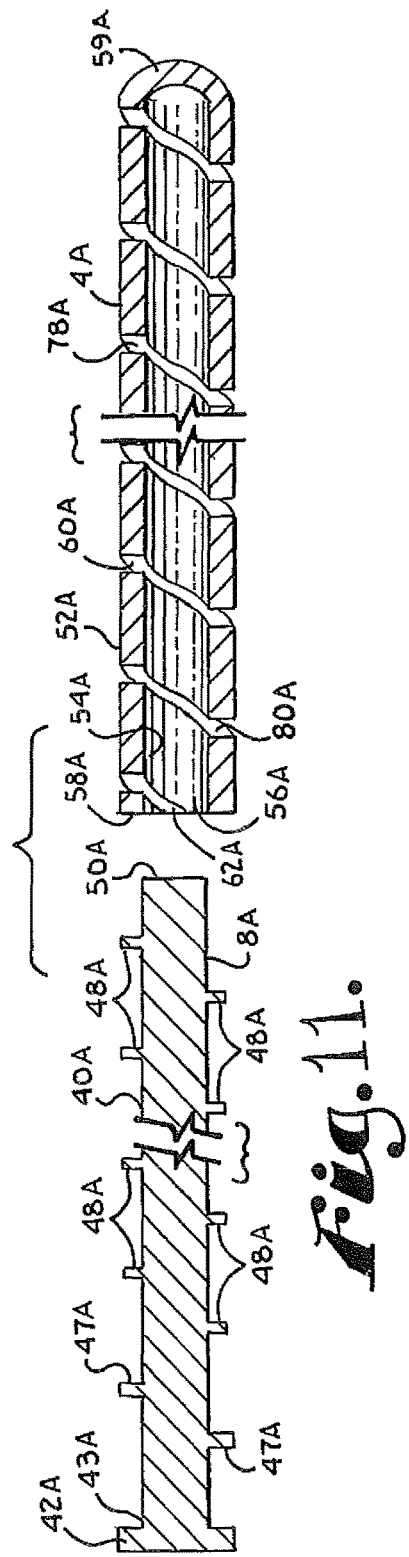

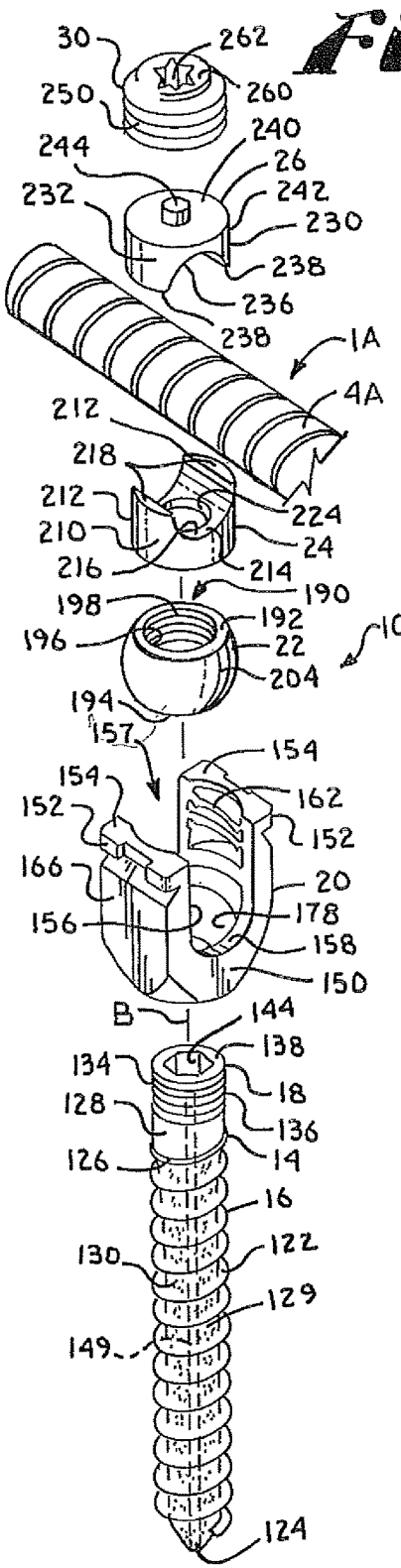
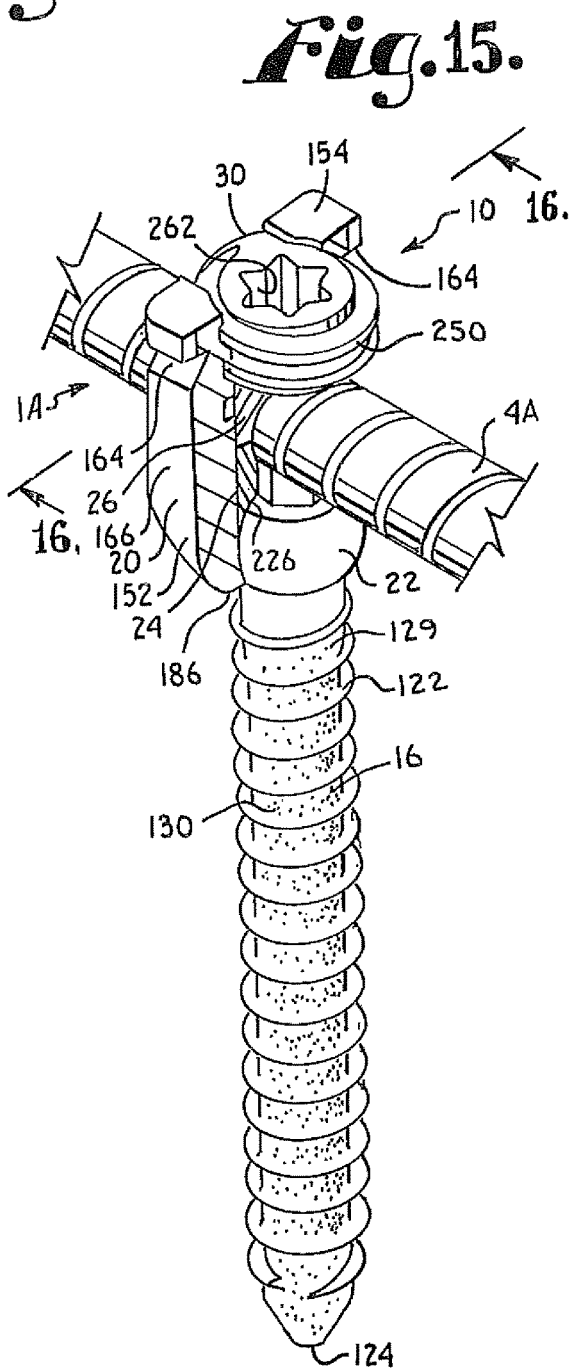
Fig. 14.
Fig. 15.

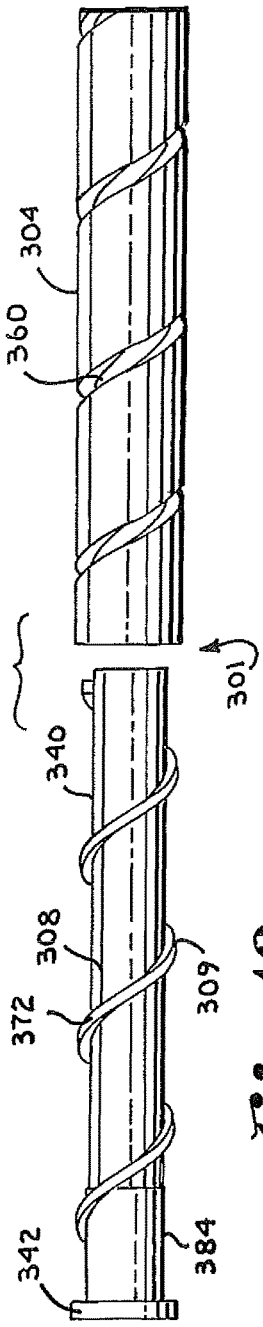
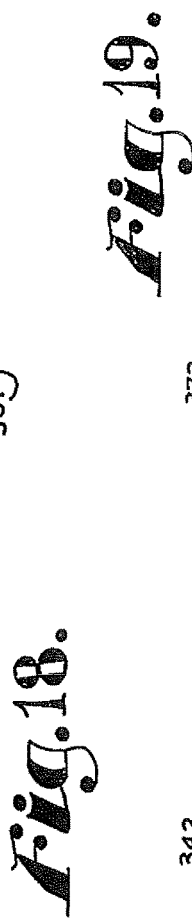
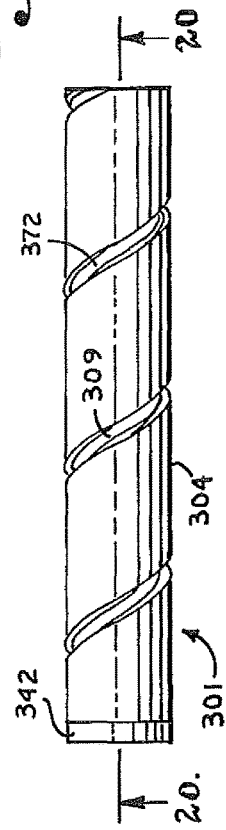
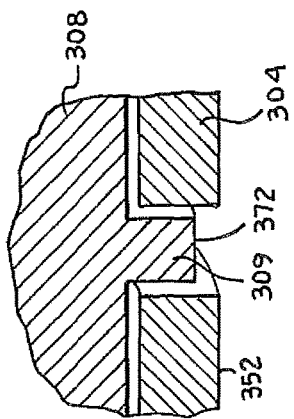

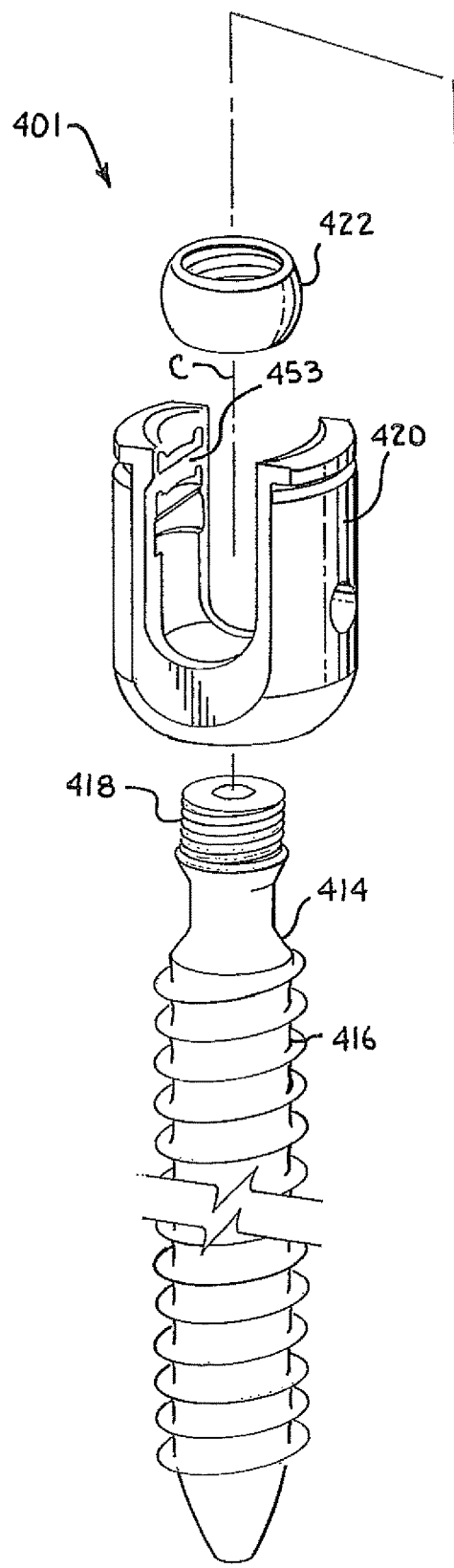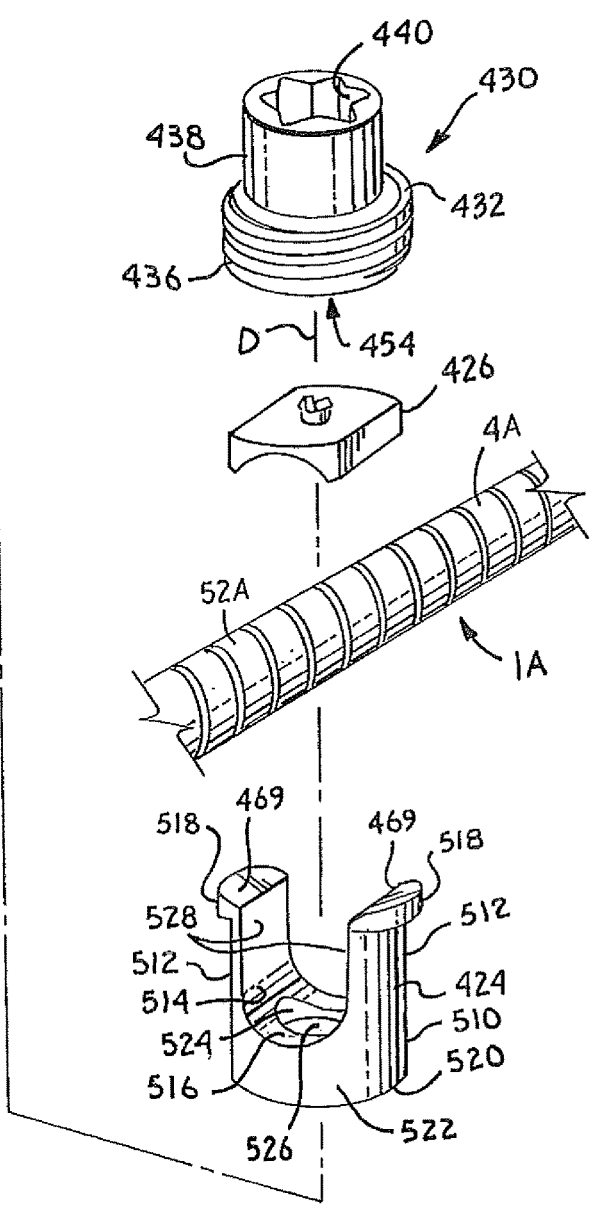
Fig. 22.

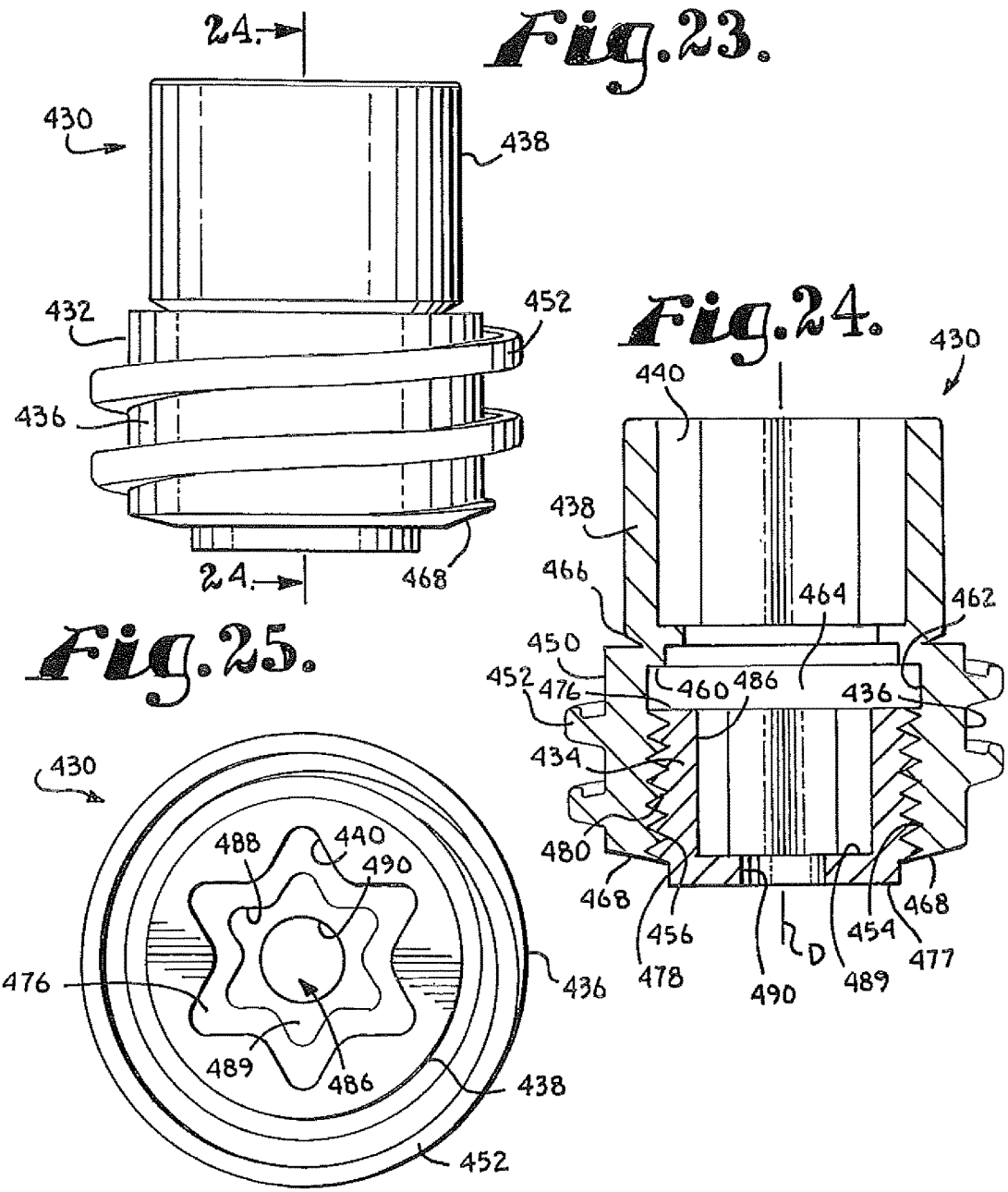

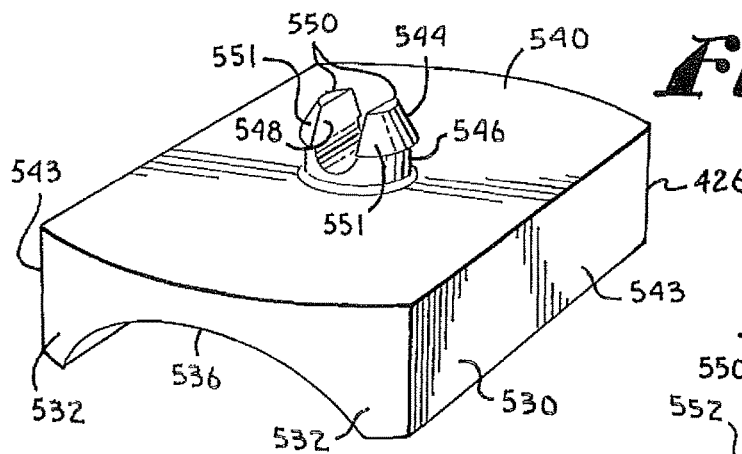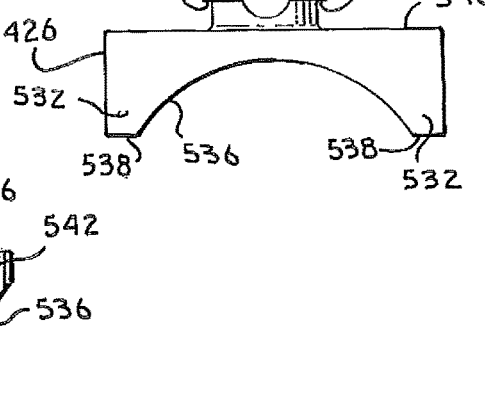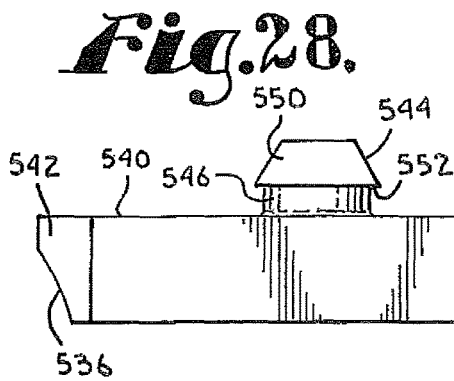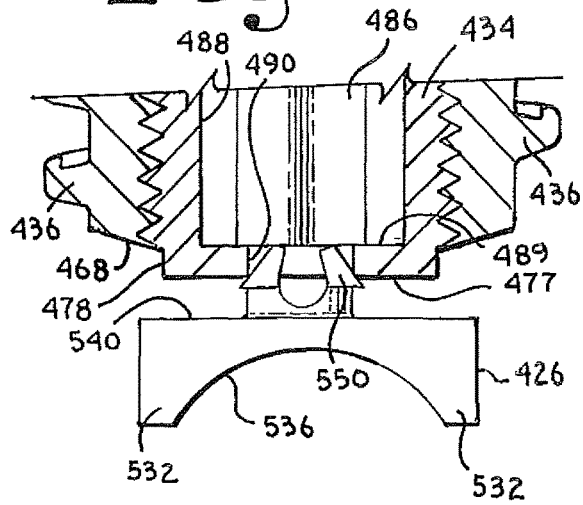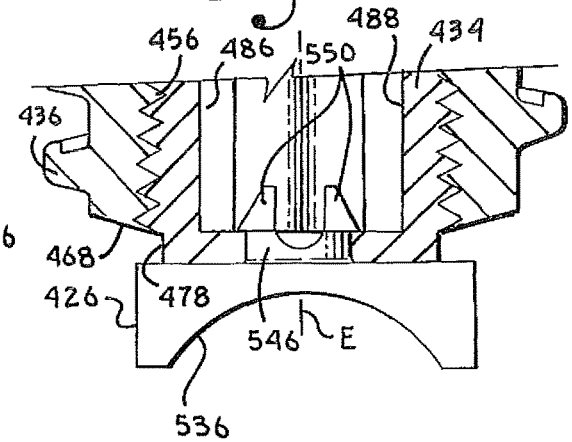

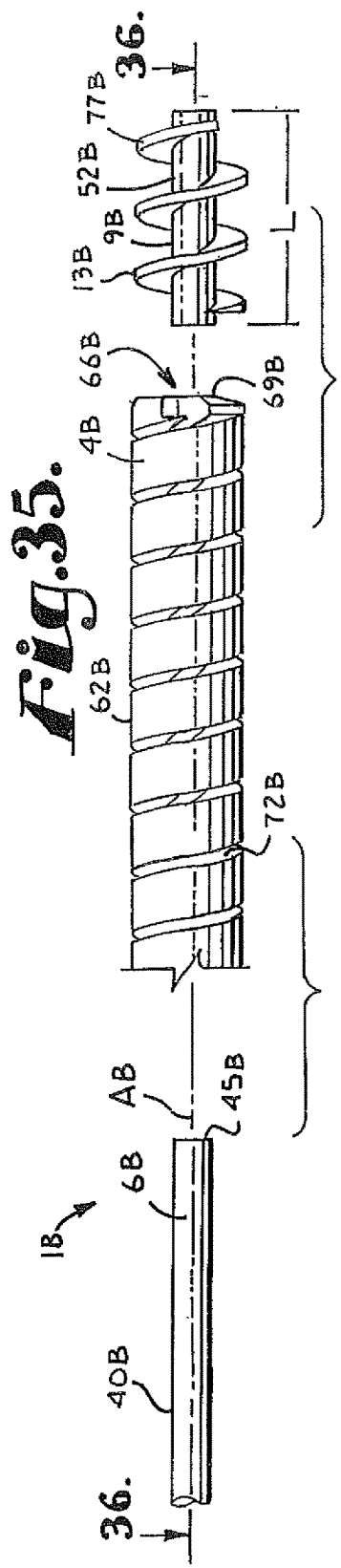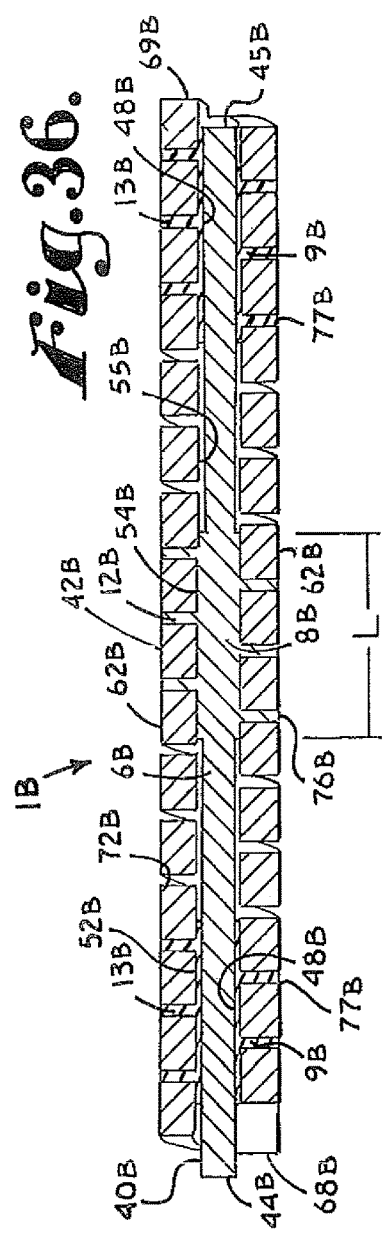

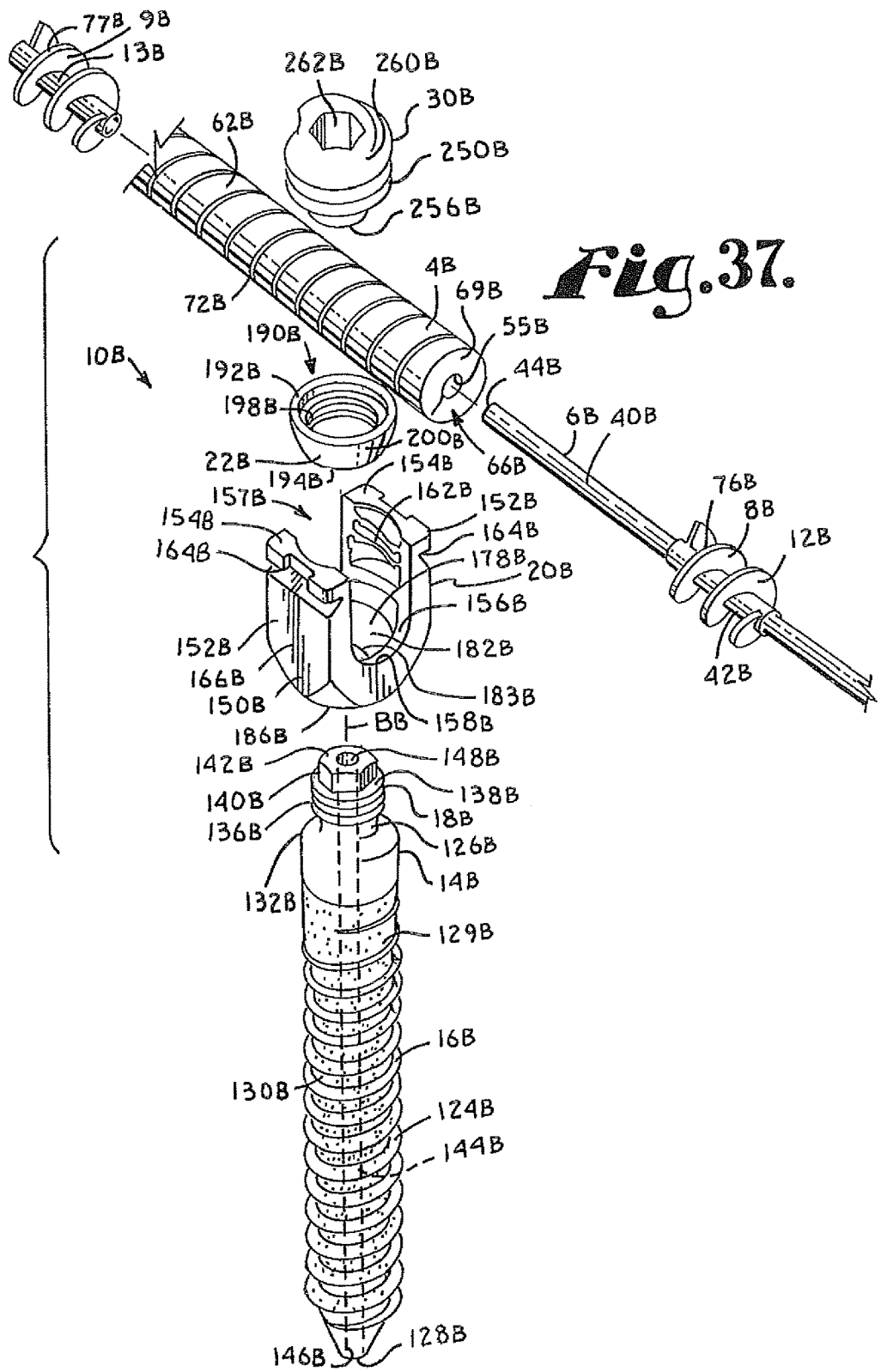

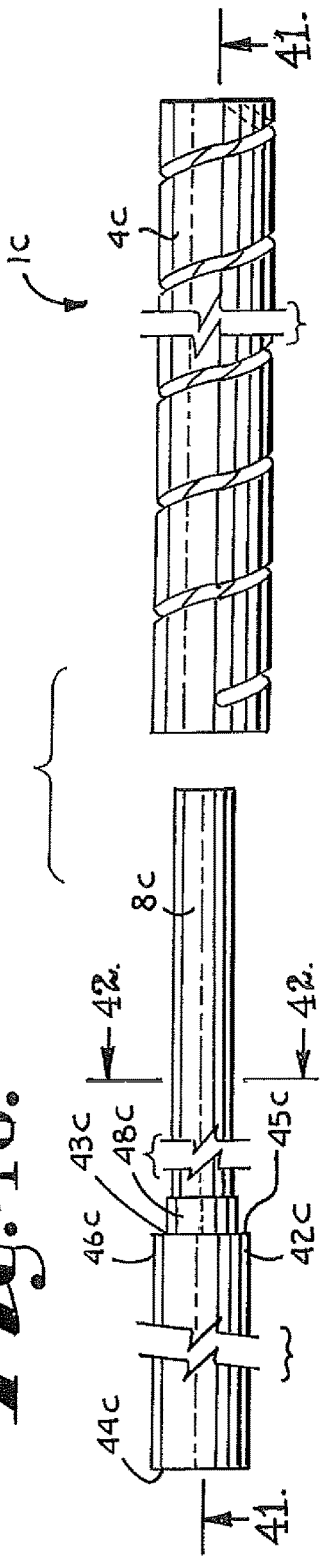
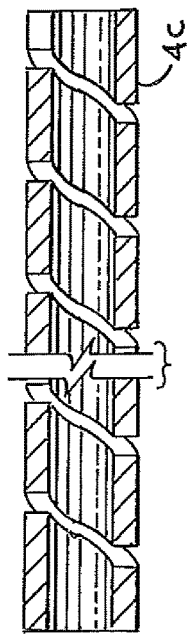
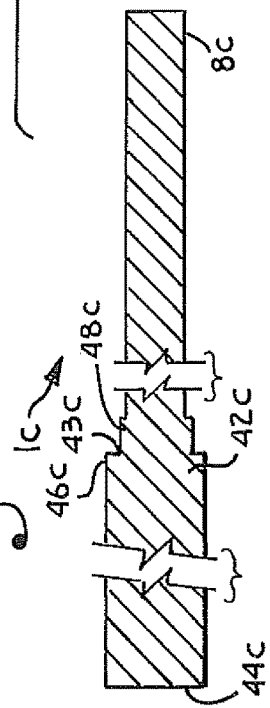
Fig. 40.
Fig. 41.
Fig. 42.

BONE ANCHOR RECEIVER WITH TOP LOADED SNAP IN PLACE INSERT

CROSS REFERENCE TO RELATED APPLICATIONS

This application is a continuation of application Ser. No. 14/557,945, filed Dec. 2, 2014, now U.S. Pat. No. 9,662,143, which is a continuation of application Ser. No. 13/815,054, filed Jan. 28, 2013, now U.S. Pat. No. 8,900,272, which is a continuation of application Ser. No. 12/804,580, filed Jul. 23, 2010, now U.S. Pat. No. 8,394,133, which is a continuation of application Ser. No. 11/522,503, filed Sep. 14, 2006, now U.S. Pat. No. 7,766,915, which claims the benefit of the following Provisional Applications: No. 60/832,644, filed Jul. 21, 2006; No. 60/736,112, filed Nov. 10, 2005; No. 60/728,912, filed Oct. 21, 2005; No. 60/725,445, filed Oct. 11, 2005; and No. 60/722,300, filed Sep. 30, 2005, all of which are incorporated by reference herein.

Application Ser. No. 11/522,503 is also a continuation-in-part of application Ser. No. 11/178,854, filed Jul. 11, 2005, now U.S. Pat. No. 7,789,896, which claims benefit of U.S. Provisional Application No. 60/655,239, filed Feb. 22, 2005, both of which are incorporated by reference herein. Application Ser. No. 11/522,503 is also a continuation-in-part of application Ser. No. 11/024,543, filed Dec. 20, 2004, now U.S. Pat. No. 7,204,838, which is incorporated by reference herein. Application Ser. No. 11/522,503 is also a continuation-in-part of application Ser. No. 10/986,377, filed Nov. 10, 2004, now U.S. Pat. No. 7,833,250, which is incorporated by reference herein.

BACKGROUND OF THE INVENTION

The present invention is directed to dynamic fixation assemblies for use in bone surgery, particularly spinal surgery, and in particular to longitudinal connecting members and cooperating bone anchors or fasteners for such assemblies, the connecting members being attached to at least two bone fasteners.

Historically, it has been common to fuse adjacent vertebrae that are placed in fixed relation by the installation therealong of bone screws or other bone anchors and cooperating longitudinal connecting members or other elongate members. Fusion results in the permanent immobilization of one or more of the intervertebral joints. Because the anchoring of bone screws, hooks and other types of anchors directly to a vertebra can result in significant forces being placed on the vertebra, and such forces may ultimately result in the loosening of the bone screw or other anchor from the vertebra, fusion allows for the growth and development of a bone counterpart to the longitudinal connecting member that can maintain the spine in the desired position even if the implants ultimately fail or are removed. Because fusion has been a desired component of spinal stabilization procedures, longitudinal connecting members have been designed that are of a material, size and shape to largely resist flexure, extension, torsion, distraction and compression, and thus substantially immobilize the portion of the spine that is to be fused. Thus, longitudinal connecting members are typically uniform along an entire length thereof, and usually made from a single or integral piece of material having a uniform diameter or width of a size to provide substantially rigid support in all planes.

Fusion, however, has some undesirable side effects. One apparent side effect is the immobilization of a portion of the spine. Furthermore, although fusion may result in a strengthened portion of the spine, it also has been linked to more rapid degeneration and even hyper-mobility and collapse of spinal motion segments that are adjacent to the portion of the spine being fused, reducing or eliminating the ability of such spinal joints to move in a more normal relation to one another. In certain instances, fusion has also failed to provide pain relief.

An alternative to fusion and the use of more rigid longitudinal connecting members or other rigid structure has been a "soft" or "dynamic" stabilization approach in which a flexible loop-, S-, C- or U-shaped member or a coil-like and/or a spring-like member is utilized as an elastic longitudinal connecting member fixed between a pair of pedicle screws in an attempt to create, as much as possible, a normal loading pattern between the vertebrae in flexion, extension, distraction, compression, side bending and torsion. Problems may arise with such devices, however, including lack of adequate spinal support and lack of fatigue strength or endurance limit. Fatigue strength has been defined as the repeated loading and unloading of a specific stress on a material structure until it fails. Fatigue strength can be tensile or distraction, compression, shear, torsion, bending, or a combination of these. The complex dynamic conditions associated with spinal movement therefore provide quite a challenge for the design of elongate elastic longitudinal connecting members that exhibit an adequate fatigue strength to provide stabilization and protected motion of the spine, without fusion, and allow for some natural movement of the portion of the spine being reinforced and supported by the elongate elastic or flexible connecting member.

SUMMARY OF THE INVENTION

Polyaxial bone screw assemblies according to the invention include longitudinal connecting members that provide dynamic, protected motion of the spine. One aspect of the invention is a dynamic medical implant assembly that includes at least two bone attachment structures and further includes an elastic and flexible longitudinal connecting member having an inner cylindrical core and an outer coil-like member. In a neutral unloaded position, the outer coil-like member is in contact with and attached to the cylindrical core at only one location. The cylindrical core is receivable in the coil-like member along a substantial length thereof. The outer coil-like member is thus in sliding engagement with the inner cylindrical core in both an axial direction and torsionally about a substantial length of the core when the core is fixed with respect to coil-like member at a discrete location, for example at ends thereof.

According to another aspect of the invention, the inner cylindrical core includes a helical thread for cooperating with the outer coil-like member. The thread may be integral with or otherwise fixed to the inner cylindrical core. The thread of the cylindrical core has substantially the same pitch as the helical slit of the outer coil-like member and is thus threadably receivable in the outer member adjacent to the internal surface and extending along a substantial length of the outer member. The outer coil-like member is in sliding engagement with the inner cylindrical core in a direction along the axis and torsionally when the core is fixed to and/or in contact with the coil-like member at one end thereof. The inner thread is sized and shaped to extend only partially into the helical slit of the outer core. Furthermore, the thread is spaced from the coil surfaces defining the helical slit, such that there is an axial gap between the core thread and the surfaces defining the helical slit. The threaded core and the coil may be coated, using methods such as ion bonding, to provide an ultra hard, ultra thin, ultra smooth and ultra slick coating to provide wear resistant hardness and limited wear debris between the contact surfaces.

According to another aspect of the invention, one or more threaded inserts are provided that slidingly mate with the inner cylindrical core and threadably cooperate with the outer coil-like member. The inner core further includes a support structure fixedly attached or integral thereto, that may be, for example, a solid rod disposed at an end of the inner core and sized and shaped to extend outwardly away from the coil-like member. Alternatively or additionally, the support structure may be in the form of a helical projection disposed at any desired location along the inner core and sized and shaped to protect the outer coil-like flexible member from being crushed or otherwise deformed by a closure member or compression insert pressing against the flexible member at the bone attachment structure. One or more tubular adjustable support structures are also provided, each with a helical projection for cooperation with the outer coil-like member. The tubular support structures are receivable on the inner core with the thread thereof receivable in the slit of the coil-like member and also extendible therethrough. In one of the illustrated embodiments, the outer coil-like member is clamped to each of the bone attachment structures at the location of the fixed and adjustable tubular supports, with the projection of each respective support extending through the slit in the outer flexible member directly resisting clamping pressure exerted by a closure structure or other compression member or insert that captures or otherwise connects with the longitudinal connecting member within a receiver of the attachment structure.

In the illustrated embodiments, the outer coil-like member includes an internal substantially cylindrical surface and an external substantially cylindrical surface. The outer coil-like member further defines a helical slit extending through the internal surface and the external surface and also preferably runs along a substantial length of the coil-like member and may include the entire length of the coil-like member. The cylindrical core is thus receivable in the outer member adjacent to the internal surface and extends along a substantial length of the outer member, the outer coil-like member being moveable with respect to the inner cylindrical core in a direction along the axis and torsionally when the core is fixed to and/or in contact with the coil-like member at least one location. While the illustrated embodiment of the invention are illustrated as linear, it is foreseen that they could be curvilinear.

In certain embodiments of the invention, the inner cylindrical core may be connected to the coil-like member with a snap-on, press fit, or other type of connection. Alternatively or additionally, when the inner core includes a helical thread, an end portion of the helical thread may be thickened to engage the coil-like member surfaces at the helical slit thereof, and be of a radial length to completely extend through the helical slit of the coil-like member. This creates a type of press fit between the core and coil-like member that is reinforced when a bone attachment structure placed at the press fit location presses against both the coil and a portion of the thread of the core. The thread winding along a remainder of the core has an outer diameter that is reduced, such that any other bone attachment structures along the length of the core and coil combination do not press against the thread of the core, but press exclusively against the coil outer cylindrical surface.

According to an aspect of the invention, the outer coil-like member external surface is clamped to each of the bone attachment structures in such a manner that the inner cylindrical core remains movable with respect to the outer coil-like member internal surface and also with at least one bone attachment structure and therefore the cylindrical core does not participate in or provide any means for torsional elasticity or axial compression and distraction along the coil-like member. Specifically, upper and lower compression members disposed in each of the bone attachment structures have radiused inner surfaces sized and shaped for exclusive frictional engagement with the outer coil-like member external surface. The compression members cooperate to clamp only the outer coil to one or more of the bone attachment structures and not crush or otherwise press against the inner cylindrical core on at least one end thereof. Thus the inner cylindrical core remains in slidable relationship with respect to the outer coil-like member along a length thereof. In certain embodiments the upper and lower compression members directly contact one another, with the upper compression member pressing upon both the lower compression member and the outer coil-like member. In another illustrated embodiment, the compression members cooperate with a closure structure that includes an outer fastener and an inner set screw. The outer fastener is pressable upon the lower compression member while the inner set screw is pressable on the upper compression member, the upper and lower compression members being in slidable contact.

According to another aspect of the invention, the bone attachment structure includes a shank or other anchor that has a surface altered by a surface roughening treatment and/or a coating to provide a bioactive interface between the bone attachment structure and a vertebra, or at least some component of bone bonding or bone ingrowth into the bone screw shank or other anchor. Such assemblies may include bone screw shanks that are either treated to provide for a roughened or porous surface, such as by plasma spraying, cleaning or coating. Furthermore, such treatment may include coating with a metal to create a scaffold for bone ingrowth or coating with other materials such as calcium phosphate bio-ceramics including hydroxyapatite and tricalcium phosphate that actively take part in bone bonding. A further aspect of the invention includes providing the longitudinal connecting member with a coating, slit filling and/or covering or sheath sized and shaped to prevent bone and/or soft tissue ingrowth on or in the coil-like member and the helical slit or slits formed thereby. In addition, the inner core and/or internal surface of the coil-like member can be coated, chemically treated or sheathed with hard, low friction materials to improve performance and decrease wear debris.

According to a further aspect of the invention, the smooth cylindrical or threaded inner core may be fixedly attached or integral with an additional connecting member at one end thereof, that is illustrated herein as a rod having a length for attachment to at least one and up to a plurality of bone screws. The illustrated additional connecting member is solid, but may be hollow, and typically has a diameter greater than a diameter of the inner core but of equal, greater or lesser diameter than an outer diameter of the coil-like member. The additional connecting member is typically cylindrical, having a circular cross section, but may also be of other shapes including rectangular, square, or other polygonal or curved cross sections.

OBJECTS AND ADVANTAGES OF THE INVENTION

Therefore, it is an object of the present invention to overcome one or more of the problems with bone attachment assemblies described above. An object of the invention is to provide dynamic medical implant stabilization assemblies having longitudinal connecting members that include an inner core insertable into an outer coil-like portion that is movable relative to the inner core when implanted. Another object of the invention is to provide dynamic medical implant stabilization assemblies that include bone screws having an affinity to bone. Also, it is an object of the invention to provide a bone fixation assembly that includes a receiver with an open channel, a shank pivotally, hingedly, or otherwise connected to the receiver, a longitudinal connecting member having a coil-like outer portion and an inner cylindrical core, a first lower compression structure disposed between the shank and the connecting member and a second upper compression structure disposed between the connecting member and a closure, the first and second compression members engaging the coil-like outer portion without engaging the inner cylindrical core. A further or alternative object of the invention is to provide adjustable inserts for such longitudinal connecting members for placement within a bone screw receiver or other bone attachment member, providing for adequate gripping and clamping of the longitudinal assembly as well as directly resisting clamping pressure, thus protecting the longitudinal member from deformation due to clamping forces. Another object of the invention is to provide a more rigid or solid connecting member surface, if desired, such as a solid rod portion integral or otherwise fixed to the inner core for bone screw attachment to such solid surface. Additionally, it is an object of the invention to provide a lightweight, reduced volume, low profile assembly including at least two bone screws and a longitudinal connecting member therebetween. Furthermore, it is an object of the invention to provide apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded and partial front elevational view of a dynamic fixation connecting member assembly according to the invention including a coil-like member and a cylindrical core.

FIG. 2 is an exploded and partial cross-sectional view taken along the line 2-2 of FIG. 1.

FIG. 3 is a cross-sectional view of the coil-like member, taken along the line 3-3 of FIG. 1.

FIG. 4 is a cross-sectional view of the cylindrical core, taken along the line 4-4 of FIG. 1.

FIG. 5 is a partial and exploded perspective view of a dynamic fixation bone screw assembly according to the invention including a bone screw shank, a receiver, a retaining structure, a first lower compression member, the dynamic fixation connecting member assembly of FIG. 1, a second upper compression member and a closure member.

FIG. 6 is an enlarged perspective view of an assembled dynamic fixation assembly of FIG. 5 with portions broken away to show detail thereof.

FIG. 7 is an enlarged and partial cross-sectional view taken along the line 7-7 of FIG. 6 of the receiver, the first and second compression members, the dynamic fixation connecting member assembly and the closure member, also shown with the shank in side elevation implanted in a vertebra and disposed at an angle with respect to the receiver.

FIG. 9 is an enlarged and partial cross-sectional view, similar to FIGS. 7 and 8, showing the different sized connecting member and cooperating upper compression member fully inserted in the receiver with the same closure top as illustrated in FIG. 7.

FIG. 10 is an exploded and partial front elevational view of a second embodiment of a dynamic fixation connecting member assembly according to the invention including a coil-like outer member and an inner threaded core.

FIG. 11 is an exploded and partial cross-sectional view taken along the line 11-11 of FIG. 10.

FIG. 14 is a partial and exploded perspective view of the dynamic fixation assembly according to the invention illustrated in FIG. 5 replacing the connecting member assembly of FIGS. 1-4 with the connecting member assembly of FIGS. 10-13.

FIG. 15 is an enlarged perspective view of an assembled dynamic fixation assembly of FIG. 14 with portions broken away to show detail thereof.

FIG. 18 is an exploded front elevational view of a third embodiment of a dynamic fixation connecting member assembly according to the invention including an outer coil-like member and an inner threaded core.

FIG. 19 is an enlarged front elevational view of the dynamic fixation connecting member of FIG. 18, showing the threaded core fully inserted in the coil-like member.

FIG. 20 is an enlarged cross-sectional view taken along the line 20-20 of FIG. 19.

FIG. 21 is an enlarged and partial cross-sectional view of a portion of the assembly shown in FIG. 20.

FIG. 22 is an enlarged, partial and exploded perspective view of a second, alternative dynamic fixation bone screw assembly according to the invention including a bone screw shank, a receiver, a retaining structure, a first lower compression member, the dynamic fixation connecting member assembly of FIG. 10, a second upper compression member and a closure member.

FIG. 23 is an enlarged front elevational view of the closure member of FIG. 22.

FIG. 24 is a cross-sectional view taken along the line 24-24 of FIG. 23.

FIG. 25 is an enlarged top plan view of the closure member of FIG. 23.

FIG. 26 is an enlarged perspective view of the upper compression member of FIG. 22.

FIG. 27 is an enlarged front elevational view of the upper compression member of FIG. 26.

FIG. 28 is an enlarged side elevational view of the upper compression member of FIG. 26.

FIG. 29 is an enlarged and partial cross-sectional view of the closure member, similar to FIG. 24 and further showing the upper compression member in front elevation prior to attachment to the closure member.

FIG. 30 is an enlarged and partial cross-sectional view of the closure member and front elevational view of the upper compression member, similar to FIG. 29, showing the upper compression member attached to the closure member and free to rotate with respect thereto.

FIG. 35 is an exploded and partial front elevational view of a fourth embodiment of a dynamic fixation connecting member assembly according to the invention including a coil-like member, a cylindrical core with fixed integral and adjustable supports having helically wound projections.

FIG. 36 is a partial cross-sectional view taken along the line 36-36 of FIG. 35.

FIG. 37 is a partial and exploded perspective view of a third embodiment of a dynamic fixation bone screw assembly according to the invention including a bone screw shank, a receiver, a retaining structure, the dynamic fixation connecting member assembly of FIG. 35, and a closure member.

FIG. 40 is an exploded and partial front elevational view of a fifth embodiment of a dynamic fixation connecting member assembly according to the invention including an outer coil-like member, an inner cylindrical core and a solid rod integral to the cylindrical core.

FIG. 41 is an exploded and partial cross-sectional view taken along the line 41-41 of FIG. 40.

FIG. 42 is a cross-sectional view of the inner coil-like member, taken along the line 42-42 of FIG. 40.

DETAILED DESCRIPTION OF THE INVENTION

Figure 8:
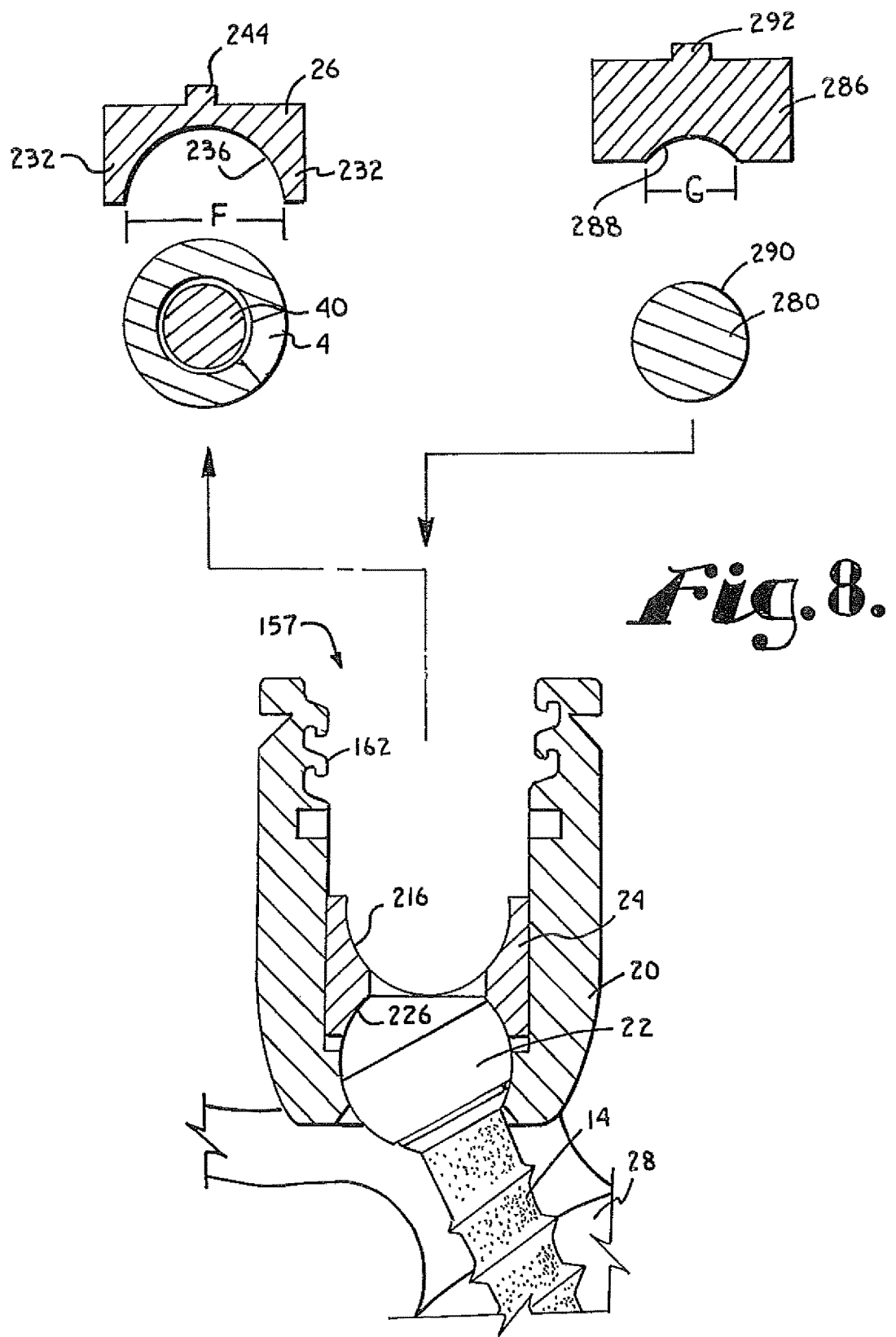
FIG. 8 is an enlarged and partial cross-sectional view, similar to FIG. 7, shown without the closure member and showing the dynamic fixation connecting member assembly and the second upper compression member removed and further showing a different sized connecting member and cooperating upper compression member for insertion in the receiver.
Figure 12:
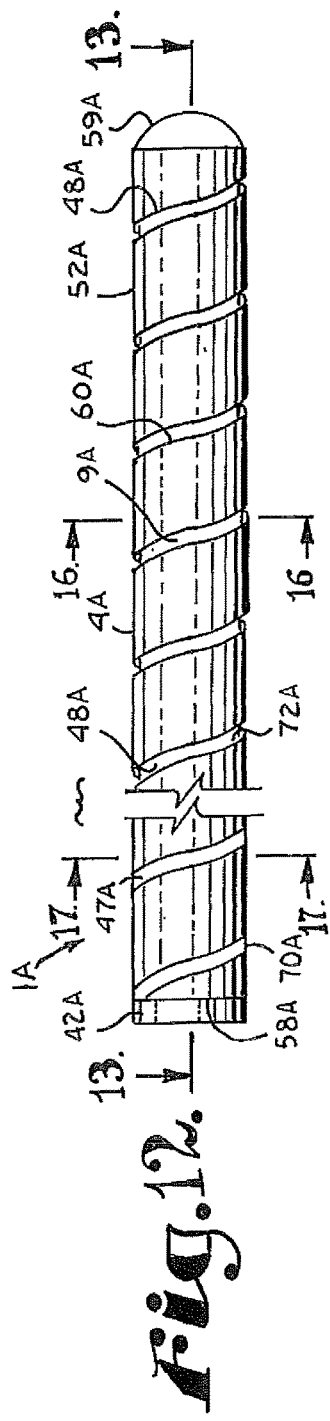
FIG. 12 is a partial front elevational view of the dynamic fixation connecting member of FIG. 10, showing the threaded core fully inserted in the coil-like member.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

With reference to FIGS. 1-7, the reference numeral 1 generally designates a non-fusion dynamic stabilization longitudinal connecting member assembly according to the present invention. The connecting member assembly 1 includes an outer, cannulated coil-like connecting member 4 and a solid cylindrical core or insert 8, receivable in the coil-like member 4 and fixed thereto at only one end of the inert 8 as will be described more fully below. The dynamic connecting member assembly 1 cooperates with at least a pair of fixed or polyaxial bone screw assemblies according to the invention, one of such assemblies, generally 10, being shown in the drawings. With reference to FIGS. 5-7, the assembly 10 includes a shank 14 that further includes a body 16 integral with an upwardly extending, substantially cylindrical upper end or capture structure 18; a receiver or head 20; a retaining and articulating structure 22; a first lower compression structure 24 and a second upper compression structure 26. The shank 14, the receiver 20, the retaining and articulating structure 22 and the first compression structure 24 are preferably assembled prior to implantation of the shank body 16 into a vertebra 28. It is noted that any reference to the words top, bottom, up and down, and the like, in this application refers to the alignment shown in the various drawings, as well as the normal connotations applied to such devices, and is not intended to restrict positioning of the assemblies 1 and 10 in actual use.

FIGS. 5-7 further show a closure structure, generally 30, of the invention for capturing the longitudinal connecting member assembly 1 within the receiver 20. Upon installation, which will be described in greater detail below, the closure structure 30 presses against the second compression structure 26 that in turn presses against the outer coil-like member 4 that in turn presses against the compression structure 24. The compression structure 24 in turn presses against the retaining and articulating structure 22 that is threadably mated or in other ways connected to the capture structure 18. As will be discussed in greater detail below, the compression structure 26 also presses against the compression structure 24 and the compression structures 24 and 26 bias the retaining and articulating structure 22 into fixed frictional contact with the receiver 20, so as to substantially attach and orient the longitudinal connecting member assembly 1 relative to the vertebra 28 and yet allow for relative movement of the outer coil-like member 4 with respect to the inner cylindrical core 8, providing relief (e.g., shock absorption) and protected movement with respect to flexion, extension, distraction and compressive forces placed on the assembly 1 and two or more connected assemblies 10. The coil-like member 4 is also able to twist or turn with respect to the cylindrical core 8, providing relief for torsional stresses. However, the solid inner core 8 does not participate in or provide any means for torsional elasticity or axial compression and distraction along a length of the outer coil 4.

Furthermore, the receiver 20, the shank 14, the retaining and articulating structure 22 and the compression structures 24 and 26 cooperate in such a manner that the receiver 20 and the shank 14 can be secured at any of a plurality of angles, articulations or rotational alignments relative to one another and within a selected range of angles both from side to side and from front to rear, to enable flexible or articulated engagement of the receiver 20 with the shank 14 until both are locked or fixed relative to each other. Alternatively, it is foreseen that the connecting assembly 1 could involve the use of an upper compression member in an open receiver that is integral or fixed in position with respect to a bone screw shank or bone hook, or that the receiver could have limited angular movement with respect to the shank, such as a hinged connection.

The longitudinal connecting member assembly 1, best illustrated in FIGS. 1-4 is elongate, with the outer coil-like member 4 being made from metal or metal alloys or other suitable materials, including plastic polymers, PEEK and UHMWP, and the inner cylindrical core 8 also made from plastics, such as polyurethanes, or metals, preferably from a metal or metal alloy that is coated or covered with a thin, hard slick material applied to it or chemically treated on it. Specifically, the core 8 includes a solid elongate, smooth-surfaced cylinder 40 having a central axis A. It may at times include a stop or rim 42 integral or fixedly attached to the cylinder 40 at an end 43 thereof. The stop 42 is substantially coaxial with the cylinder 40. In the embodiment shown, the stop 42 includes a flat abutment surface 44 and an outer cylindrical surface 46. A snap-on attachment nob or nub 48 protrudes in a radial direction from a lower portion 49 of the elongate cylinder 40 and near the end 43 thereof. Near an opposite end 50 thereof, the cylinder 40 does not include structure for fixed attachment to the coil-like member 4. The cylinder 40 has a substantially uniform outer radius that is slightly smaller than an inner radius of an internal substantially cylindrical surface 54 of the coil-like member 4, providing a slight gap 51 about the cylinder 40 (FIG. 7), substantially annular in cross-section, located between the cylinder 40 and the surface 54 when the cylinder 40 is inserted into and fully received by the coil-like member 4. The gap 51 that spans along a substantial length of the cylinder 40 from the lower portion 49 to the end 50 allows for sliding, axial (back and forth) movement of the coil-like member 4 with respect to the cylinder 40, along the axis A as well as twisting or torsional movement by the member 4.

The coil-like member 4 is also substantially cylindrical with an external substantially cylindrical surface 52 and the internal substantially cylindrical and smooth surface 54 previously identified herein. The surface 54 defines a bore 56 with a circular cross section, the bore 56 extending completely or substantially through the coil-like member 4. The member 4 has a substantially flat and annular end surface 58 and a substantially flat and annular opposite end surface 59. The member 4 further includes a helical slit 60 that extends therethrough from the external surface 52 to the internal surface 54 and beginning at a location 62 near the end surface 58 and winding along an entire or substantial length of the coil-like member 4. The slit 60 illustrated in FIG. 1 runs through the end surface 59 (shown in phantom). Alternatively, it is foreseen that the slit 60 may end at or near the end surface 59. It is also foreseen that the slit 60 may extend through the end surface 58. A circular, U-shaped surface 66 defines a recess 68 at the internal surface 54 and located between the end surface 58 and the location 62 marking the beginning of the helical slit 60. The recess 68 is substantially annular and is sized and shaped to receive the nob 48 at any location therealong when the inner core 8 is received in the outer coil-like member 4 with the surface 58 abutting the surface 44. The cooperation between the nob 48 and the recess 68 provides a "snap" fit between the core 8 and the outer coil-like member 4, fixing the core 8 to the member 4 at the respective ends 43 and 58.

The coil-like member internal cylindrical surface 54 is of a slightly greater diameter than an outer diameter of the cylinder 40, allowing for axially directed sliding movement of the coil-like member 4 with respect to the solid cylinder 40. It is foreseen that the lower portion 49 of the cylinder 40 may have a diameter slightly greater than the diameter of a remainder of the solid cylinder 40, providing for frictional engagement between the lower portion 49 and the internal surface 54 of the coil-like member 4, giving some additional attachment and reinforcement of the snap fit between the member 4 and the core 8 near or at the nob 48. When the cylindrical core 8 is inserted in the coil-like member 4 and the nob 48 engages the recess 68, the core 8 extends completely or substantially through the bore 56 along the axis A and along a substantial length of the coil-like member 4 to near the end surface 59, with the end surface 50 being near or adjacent the end surface 59. The coil-like member 4 is not fixed to the solid core 8 at or near the end surfaces 50 and 59. Furthermore, as will be described more fully below, the bone screw assembly 10 is sized and shaped to frictionally engage the coil-like member 4 without crushing or otherwise frictionally engaging or fixing the coil-like member 4 against the core 8 within any cooperating bone screw assembly 10, thus allowing for relative movement between the coil-like member 4 and the solid core 8 along a substantial length of the assembly 1.

It is noted that the core 8 may be sized and made from such materials as to provide for a relatively more rigid assembly 1 or a relatively more flexible assembly 1 with respect to flex or bendability along the assembly 1. Such flexibility therefore may be varied by changing the outer diameter of the core 8 and thus likewise changing the diametric size of the coil-like member 4. Also, it is noted that longer assemblies 1 may need to be stiffer and thus larger in diameter than shorter assemblies 1. In addition, since the distance between the bone screw assembly receivers or heads can vary, the coil-case assembly may need to be more or less stiff.

It is foreseen that in order to keep scar tissue from growing into the coil-like member 4 through the helical slit 60, an inner or outer sleeve or sheath-like structure may be placed, adhered or otherwise applied to either the external surface 52 or the internal surface 54 of the coil-like member 4. Such a sheath-like structure would be of a size and shape such that axial movement of the coil-like member 4 is not hindered and thus any relative movement between the coil-like member 4 and the cylindrical core 8 is not hindered or prevented.

The shank 14 of the bone screw assembly 10, best illustrated in FIGS. 5-7, is elongate, with the shank body 16 having a helically wound, radially outwardly extending bone implantable thread 122 axially extending from near a tip 124 of the body 16 to near a slanted or sloped surface 126 that is adjacent to a smooth cylindrical surface 128 located adjacent to the capture structure 18. The laterally projecting cylindrical surface 128 includes a buttress stop feature for frictional engagement with and placement of the retaining and articulating structure 22. During use, the body 16 utilizing the thread 122 for gripping and advancement is implanted into the vertebra 28 leading with the tip 124 and driven down into the vertebra 28 with an installation or driving tool so as to be implanted in the vertebra 28 to near the sloped surface 126.

To provide a biologically active interface with the bone, an outer surface 129 of the shank body 16 that includes the thread 121 and extends between the surface 126 and the tip 124 is coated, perforated, made porous or otherwise treated 130. The treatment 130 may include, but is not limited to a plasma spray coating or other type of coating of a metal or, for example, a calcium phosphate; or a roughening, perforation or indentation in the surface 129, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate $(Ca_3(PO_4)_2)$, tetra-calcium phosphate $(Ca_4P_2O_9)$, amorphous calcium phosphate and hydroxyapatite $(Ca_{10}(PO_4)_6(OH)_2)$. Coating with hydroxyapatite, for example, is desirable as hydroxyapatite is chemically similar to bone with respect to mineral content and has been identified as being bioactive and thus not only supportive of bone ingrowth, but actively taking part in bone bonding.

The sloped surface 126 extends radially outward and axially upward from the shank body 16 to the cylindrical projection 128. Further extending axially from the projection 128 is the capture structure 18 that provides a connective or capture apparatus disposed at a distance from the threaded shank body 16 and thus at a distance from the vertebra 28 when the body 16 is implanted in the vertebra 28.

The capture structure 18 is configured for connecting the shank 14 to the receiver 20 and capturing the shank 14 in the receiver 20. The capture structure 18 has an outer substantially cylindrical surface 134 having a helically wound guide and advancement structure thereon which in the illustrated embodiment is a V-shaped thread 136 extending from adjacent the cylindrical surface 128 to adjacent an annular top or upper surface 138. The upper surface 138 is disposed substantially perpendicular to an axis of rotation B of the shank 14. A diameter of the cylindrical surface 134 measured between roots of the thread 136 is smaller than a diameter of the projected cylindrical surface 128. A diameter measured between crests of the thread 136 is illustrated equal to and may be smaller than the diameter of the cylindrical surface 128. Although a simple thread 136 is shown in the drawings, it is foreseen that other structures including other types of threads, such as buttress, square and reverse angle threads, and non threads, such as helically wound flanges with interlocking surfaces, may be alternatively used in place of the thread 136 in alternative embodiments of the present invention.

A hex-shaped driving formation 144 extends from the upper surface 138 into the capture structure 18. The driving formation 144 is sized and shaped to cooperate with a hex-driver for rotating and driving the shank body 16 into bone. It is foreseen that other driving features or apertures, such as slotted, tri-wing, hexalobular (such as the 6-point star shaped pattern sold under the trademark TORX), spanner, or the like may also be utilized according to the invention.

In the illustrated embodiment, the shank 14 is cannulated with a small central bore 149 extending an entire length of the shank along axis B. The bore 149 is coaxial with the threaded body 16 and the capture structure outer surface 134, providing a passage through the shank interior for a length of wire or pin inserted into the vertebra 28 prior to the insertion of the shank body 16, the wire or pin providing a guide for insertion of the shank body 16 into the vertebra 28.

Also with reference to FIGS. 5-7, the receiver 20 includes a base 150 integral with a pair of opposed upstanding arms 152 that extend from the base 150 to a top surface 154. The arms 152 form a U-shaped cradle and define a U-shaped channel 156 between the arms 152 and include an upper opening 157 and a lower seat 158 having substantially the same radius as the outer coil-like member 4 of the longitudinal connecting member assembly 1 for operably snugly receiving the member assembly 1.

Each of the arms 152 has an interior surface that defines an inner cylindrical profile and includes a partial helically wound guide and advancement structure 162. In the illustrated embodiment, the guide and advancement structure 162 is a partial helically wound flangeform configured to mate under rotation with a similar structure on the closure member 30, as described more fully below. However, it is foreseen that the guide and advancement structure 162 could alternatively be a buttress thread, a square thread, a reverse angle thread or other thread like or non-thread like helically wound advancement structures for operably guiding under rotation and advancing the closure 30 downward between the arms 152 and having such a nature as to resist splaying of the arms 152 when the closure 30 is advanced into the U-shaped channel 156.

Each of the arms 152 includes a V-shaped or undercut tool engagement groove 164 formed on a substantially planar outer surface 166 thereof which may be used for holding the receiver 20 with a holding tool (not shown) having projections that are received within the grooves 164 during implantation of the shank body 16 into the vertebra 28. The grooves 164 may also cooperate with a holding tool during bone screw assembly and during subsequent installation of the connecting member 1 and closure 30. It is foreseen that tool receiving grooves or apertures may be configured in a variety of shapes and sizes and be disposed at other locations on the arms 152.

Communicating with the U-shaped channel 156 and located within the base 150 of the receiver 20 is a chamber or cavity 178 partially defined by an inner cylindrical surface 180 and a substantially spherical seating surface 182, the cavity 178 opening upwardly into the U-shaped channel 156. The base 150 further includes a restrictive neck 183 adjacent the seating surface 182. The neck 183 defines an opening or bore communicating with the cavity 178 and a lower exterior 186 of the base 150. The neck 183 is conically counterbored or beveled to widen the angular range of the shank 14. The neck 183 is sized and shaped to be smaller than a radial dimension of a fixed or fully expanded retaining and articulating structure 22 so as to form a restriction at the location of the neck 183 relative to the retaining and articulating structure 22, to prevent the structure 22 from passing from the cavity 178 and out into the lower exterior 186 of the receiver 20 when the retaining and articulating structure 22 is seated on the seating surface 182. It is foreseen that the retaining and articulating structure could be compressible (such as where such structure has a missing section) and could be loaded through the neck 183 and then allowed to expand and fully seat in the spherical seating surface 182. Other bottom loading capture structures could be utilized.

The retaining and articulating structure 22 has an operational central axis that is the same as the elongate axis B associated with the shank 14. The retaining and articulating structure 22 has a central bore 190 that passes entirely through the structure 22 from a top surface 192 to a bottom surface 194 thereof. An inner cylindrical surface 196 defines a substantial portion of the bore 190, the surface 196 having a helically wound guide and advancement structure thereon as shown by a v-shaped helical rib or thread 198 extending from adjacent the top surface 192 to near the bottom surface 194. Although a simple helical rib 198 is shown in the drawings, it is foreseen that other helical structures including other types of threads, such as buttress and reverse angle threads, and non threads, such as helically wound flanges with interlocking surfaces, may be alternatively used in an alternative embodiment of the present invention. The inner cylindrical surface 196 with the thread 198 are configured to mate under rotation with the capture structure outer surface 134 and helical guide and advancement structure or thread 136.

The illustrated retaining and articulating structure 22 has a radially outer partially spherically shaped surface 204 sized and shaped to mate with the partial spherically shaped seating surface 182 of the receiver and having a radius approximately equal to the radius associated with the surface 182. The retaining and articulating structure radius is larger than the radius of the neck 183 of the receiver 20. Although not required, it is foreseen that the outer partially spherically shaped surface 204 may be a high friction surface such as a knurled surface or the like.

It is also foreseen that the retaining and articulating structure outer surface may be elliptical or ellipsoid in shape rather than spheroid in shape. Such an elliptical surface would be sized and shaped to contact and seat within a substantially spherical seating surface, such as the seating surface 182. Such an ellipsoid structure may be attachable to the shank upper portion by threads, a pin, compression, or the like as previously described with respect to the substantially spherical retaining and articulating structure 22. Furthermore, it is foreseen that an ellipsoid retaining structure may be integral with the bone screw shank and may include threads that allow the ellipsoid to be threadably received into a base of a bone screw receiver. Again, it is foreseen that other types of retaining structure, articulating and not, could be used to keep the upper end of the shank contained within the receiver.

The illustrated retaining and articulating structure top surface 192 extends from the central bore 190 to the outer surface 204. The top surface 192 is disposed perpendicular to an axis of rotation of the structure 22. The bottom surface 294 also is disposed perpendicular to the structure 22 axis of rotation.

The lower compression structure 24 includes a body 210 of substantially circular cross-section integral with a pair of upstanding arms 212. The body 210 and arms 212 form a generally U-shaped, open, through-channel 214 having a partially U-shaped bottom seating surface 216 having a radius substantially conforming to an outer radius of the coil-like member 4 and thus configured to operably snugly engage the coil member 4 at the outer surface 52 thereof. The arms 212 disposed on either side of the channel 214 each include a top surface 218 that is parallel to an annular bottom surface 220. The compression structure 24 includes a substantially cylindrical outer surface 222 and an inner cylindrical wall 224 defining a central through-bore extending along a central axis of the compression structure 24. The top surface 218 and the bottom surface 220 are substantially parallel. Extending between the inner cylindrical wall 224 and the bottom surface 220 is a curved or spherical surface 226 sized and shaped to frictionally engage and mate with the outer spherical surface 204 of the retaining and articulating structure 22. The cylindrical surface 222 has a diameter slightly smaller than a diameter between crests of the guide and advancement structure 162 allowing for top loading of the compression structure 24. The cylindrical surface 222 diameter and a height of the compression structure 24 measured from the top surface 218 to the bottom surface 220 are sized such that the compression structure 24 is received within the cylindrical surface 180 of the receiver 20 below the guide and advancement structure 162, but the bottom surface 220 is spaced from a surface 227 of the receiver base 150 regardless of the angular position of the shank 14 with respect to the receiver 20.

The upper or second compression structure 26 includes a body 230 of substantially circular cross-section integral with a pair of downwardly extending arms 232. The body 230 and the arms 232 form a generally U-shaped, open, through-channel having a substantially U-shaped seating surface 236 having a radius substantially conforming to the outer radius of the coil-like member 4 and thus configured to operably snugly engage the coil member 4 at the external surface 52 thereof opposite the first or lower compression structure 24. The arms 232 each included a bottom surface 238 that is parallel to a planar top surface 240. The compression structure 26 includes a substantially cylindrical outer surface 242. A pin 244 of substantially circular cross section is disposed centrally on the top surface 240 and extends upwardly therefrom, being sized and shaped to fit within a central aperture of the closure 30 to be discussed more fully below. The cylindrical surface 242 has a diameter slightly smaller than a diameter between crests of the guide and advancement structure 162 allowing for top loading of the compression structure 26. The second compression structure 26 is sized and shaped to abut against both the compression structure 24 and the coil-like member 4 when pressed upon by the closure 30, allowing for clamping of the coil-like member 4 between the insert 26 and the insert 24 as well as additional compressive force being placed against the compression structure 24 that in turn presses the retaining and articulating structure 22 against the spherical seating surface 182 of the receiver 20, clamping the bone screw shank 14 into a fixed angular position with respect to the receiver 20 as illustrated in FIG. 7.

With reference to FIGS. 5-7, the closure structure 30 can be any of a variety of different types of closure structures for use in conjunction with the present invention with suitable mating structure on the upstanding arms 152 of the receiver 20. The closure structure 30 is rotatable between the spaced arms 152, but could be a slide-in closure structure. The illustrated structure closure structure 30 is substantially cylindrical and includes an outer helically wound guide and advancement structure in the form of a flange form 250. The illustrated guide and advancement structure 250 operably joins with the guide and advancement structure 162 disposed on the interior of the arms 152. In the illustrated embodiment, the flange form 250 has a protrusion 251 that projects rearwardly from a trailing surface thereof that effectively locks the closure structure 30 to the structure 162 within which it is set so as to prevent splaying of the arms 152 upon which mating guide and advancement structure 162 is mounted. The guide and advancement structure 250 utilized in accordance with the present invention may take other forms, including those described in Applicant's U.S. Pat. No. 6,726,689, which is incorporated herein by reference. It is also foreseen that according to the invention the guide and advancement structure 250 could alternatively be a buttress thread, a square thread, a reverse angle thread or other thread like or non-thread like helically wound advancement structure for operably guiding under rotation and advancing the closure structure 30 downward between the arms 152 and having such a nature as to resist splaying of the arms 152 when the closure structure 30 is advanced into the U-shaped channel 156.

The closure structure 30 includes a lower surface 256 having a central recess 258 formed thereon. The recess 258 is substantially cylindrical having a central axis operationally coaxial with the receiver 20 and the second compression structure 26. The lower surface 256 is planar. The central recess 258 is sized and shaped to receive the pin 244 of the compression structure 26, with the lower surface 256 frictionally engaging the top planar surface 240 of the compression structure 26 when fully mated therewith, as illustrated in FIG. 7.

The closure structure 30 has a top surface 260 with an internal drive in the form of an aperture 262, illustrated as a star-shaped internal drive, for example, sold under the trademark TORX. A driving tool (not shown) sized and shaped for engagement with the internal drive 262 is used for both rotatable engagement and, if needed, disengagement of the closure 30 from the arms 152. Although a star-shaped internal drive 258 is shown in the drawings, the tool engagement structure may take a variety of tool-engaging forms and may include but is not limited to a hex shape or more than one aperture of various shapes. It is also foreseen that the closure structure 30 may alternatively include a break-off head designed to allow such a head to break from a base of the closure at a preselected torque, for example, 70 to 140 inch pounds. Such a closure structure would also include a base having an internal drive to be used for closure removal.

During installation, the lower surface 256 engages the upper compression structure 26 that in turn engages the outer coil-like member 4 of the connecting assembly 1. The closure structure 30 is rotated, using a tool engaged with the inner drive 262 until a selected pressure is reached at which point the longitudinal connecting assembly 1 is urged toward, but not completely to the lower seat 158 of the channel 156. In turn, the coil-like member 4 braces against the lower compression structure 24. The pressure placed on the outer surface of the coil-like member 4 by the closure structure 30 is sufficient to clamp the member 4 between the upper and lower compression structures 24 and 26, but not enough to crush or press the coil-like member 4 into fixed engagement with the cylinder 40 of the core 8 because of the engagement of the lower surfaces 238 of the compression structure 26 with the top surfaces 218 of the compression structure 24. Engagement between the surfaces 238 and 218 allow for additional torquing of the closure structure 30 to fix the bone screw shank 14 between the compression structure 24 and the receiver seating surface 182, without crushing the coil-like member 4 against the core 8. For example, about 50 to about 80 inch pounds of pressure are required for fixing the connecting assembly 1 in place without crushing the coil-like member 4 against the core 8. However, about 80 to about 120 inch pounds pressure may be required for fixing the bone screw shank 14 with respect to the receiver 20. The cooperation between the compression members 24 and 26 at the surfaces 218 and 238, respectively, and the cradling of the assembly 1 between the compression members 24 and 26 due to cylindrical inner surfaces thereof, allow for a total torquing of 80 to 120 inch pounds, with only 50 to 80 inch pounds of that force being placed on the coil-like member 4.

Prior to the polyaxial bone screw assembly 10 being implanted in the vertebra 28, the retaining and articulating structure 22 is typically first inserted or top-loaded, into the receiver U-shaped channel 156, and then into the cavity 178 to dispose the structure 22 adjacent the inner seating surface 182 of the receiver 20. The shank capture structure 18 is preloaded, inserted or bottom-loaded into the receiver 20 at the neck bore 183. The retaining and articulating structure 22, now disposed in the receiver 20 is coaxially aligned with the shank capture structure 18 so that the helical v-shaped thread 136 rotatingly mates with the thread 198 of the retaining and articulating structure 22. The shank 14 and/or the retaining and articulating structure 22 are rotated to fully mate the structures 136 and 198, fixing the capture structure 18 to the retaining and articulating structure 22. At this time the shank 14 is in slidable and rotatable engagement with respect to the receiver 20, while the retaining and articulating structure 22 and the lower aperture or neck 183 of the receiver 20 cooperate to maintain the shank body 16 in rotational relation with the receiver 20. The shank body 16 can be rotated through a substantial angular rotation relative to the receiver 20, both from side to side and from front to rear so as to substantially provide a universal or ball joint wherein the angle of rotation is only restricted by engagement of the sloped surface 126 of the shank body 16 with the neck 183 of the receiver 20.

In the embodiment shown, the compression structure 24 is then loaded into the receiver 20 with the U-shaped seating surface 216 aligned with the receiver 20 U-shaped channel 156. The compression structure 24 is initially top or down-loaded into the receiver 20 until the arms 212 are disposed adjacent to the surface 180 and the bottom spherical surface 226 is in contact with the surface 204 of the retaining and articulating structure 22. To ready the assembly 10 for implantation into bone, the shank 14, the receiver 20 and the compression structure 24 central axes are aligned along axis B, providing access to the hex-shaped formation 144 on the shank capture structure 18 through the central bore formed by the inner cylindrical wall 224 of the compression structure 24.

The assembly 10 is then typically screwed into a bone, such as the vertebra 28, by rotation of the shank 14 using a driving tool (not shown) with an Allen type driving formation that operably drives and rotates the shank 14 by engagement thereof with the shank at the driving formation 144. It is foreseen that in other embodiments according to the invention, the hex-shaped driving formation 144 may be replaced by other types of foot print type tool engaging formations or recesses. Through the driving formation aperture, the retaining structure and the shank may also be crimped together so as to not come apart with rotation.

At least two and up to a plurality of bone screw assemblies 10 are implanted into vertebrae for use with the longitudinal connecting member assembly 1. Each vertebra 28 may be pre-drilled to minimize stressing the bone. Furthermore, when a cannulated bone screw shank is utilized, each vertebra will have a guide wire or pin (not shown) inserted therein that is shaped for the bone screw cannula 149 of the bone screw shank and provides a guide for the placement and angle of the shank 14 with respect to the vertebra 28. A further tap hole may be made and the shank body 16 is then driven into the vertebra 28, by rotation of the driving tool (not shown). It is foreseen that the screws and the longitudinal connecting member can be inserted in a percutaneous or minimally invasive surgical manner.

With particular reference to FIGS. 1-4, the longitudinal connecting member assembly 1 is assembled by inserting the cylinder 40 of the core 8 into the bore 56 defined by the inner cylindrical surface 54 of the coil-like member 4. The end 50 of the core 8 is placed into the open end 58 of the coil-like member 4 and the member 4 is moved toward the stop or rim 42 until the nub 48 snaps into the recess 68, with the end 58 preferably in frictional contact with the flat abutment surface 44.

The connecting member assembly 1 is eventually positioned in an open or percutaneous manner within the U-shaped channels 156 of two or more bone screw assemblies 10. The assembly 1 can be straight, pre-bent or curvilinear. The second or upper compression structure 24 is then placed in each assembly 10 with the U-shaped seating surface 236 facing the coil-like member 4. The closure structure 30 is then inserted into and advanced between the arms 152. As the closure structure 30 is rotated between the arms 152, the central recess or aperture 258 receives the pin 244 of the compression member 26, centering the member 26 with respect to the receiver 20 and the connecting member assembly 1. Continued rotation of the closure structure 30 results in engagement between the surfaces 240 and 256, uniformly pressing the compression member 26 against the coil-like member 4 at the seating surface 236 of the compression member 26 and the outer substantially cylindrical, but discontinuous surface 52 of the coil-like member 4. The coil-like member 4 in turn presses downwardly against the seating surface 216 of the lower compression structure 24, pressing the structure 24 downwardly into engagement with the retaining and articulating structure outer surface 204 to set the angle of articulation of the shank body 16 with respect to the receiver 20. As previously described, the compression structure 26 also presses against the compression structure 24 at the surface 218 as the closure structure is torqued 30, clamping the shank body 16 into a fixed position with respect to the receiver 20. However, the cylindrical surfaces 216 and 236 of the compression structures 24 and 26, respectively, cradle and protect the coil-like member 4 from crushing against the core 8. Thus, although torquing of the closure structure 30 against the compression structure 26 clamps the coil-like member 4 with enough force to keep the member 4 in a fixed position in the receiver 20, the upper and lower compression structures 24 and 26 provide for the gap 51 to exist between the cylinder 40 of the core 8 and the coil-like member 4 such that relative movement between the cylinder 40 and the member 4 is possible, along substantially the entire length of the cylinder 40 with the exception of the end portion 49 that is attached to the member 4 with the snap-on nob 48 and cooperating recess 68 formed by the inner surface 66. As will be described more fully below, in some embodiments according to the invention it is possible to insert the closure structure pre-attached to the upper compression structure with the two parts snapped together.

If removal of the assembly 1 from any of the assemblies 10 is necessary, or if it is desired to release the assembly 1 at a particular location, disassembly is accomplished by using the driving tool (not shown) with a star-shaped driving formation on the closure structure 30 internal drive 262 to rotate and remove the closure structure 39 from the receiver 20. Disassembly of the assembly 10 is accomplished in reverse order to the procedure described previously herein for assembly.

The polyaxial bone screw assembly 10 according to the invention advantageously allows for the removal and replacement of the longitudinal connecting member assembly 1 with another longitudinal connecting member having a different overall or outer diameter, utilizing the same receiver 20 and the same lower compression structure 24. For example, as illustrated in FIGS. 8 and 9, the flexible longitudinal member connecting assembly 1 having an outer diameter F may be removed and replaced by a more rigid assembly, such as a solid rod 280 having an outer diameter G that is smaller than the diameter F of the outer coil-like member 4. The rod 280 is inserted into the receiver opening 157 followed by a cooperating upper compression structure 286, and then the closure structure 30 is re-inserted and tightened within the receiver 20. The upper compression structure 286 is substantially similar to the compression structure 26 with the exception that the structure 286 is sized and shaped to include a mating surface 288 for closely cooperating with and contacting an outer cylindrical surface 290 of the longitudinal connecting member 280. For example, in the embodiment shown, the surface 288 has an inner radius of curvature almost identical to an outer radius of curvature of the surface 290. The compression structure 286 further includes an upper pin 292 identical or substantially similar to the pin 244 described previously with respect to the compression structure 26. The pin 292 is receivable in the central recess 258 of the closure structure 30, ensuring that when fully assembled in the receiver 20, the compression structure 26 is properly centered and in full contact with the rod 280, which in turn centers the rod 280 with respect to the lower compression member 24 for optimum contact between the rod 280 and the lower compression member 24. It is not necessary that the lower compression member 24 be in contact with the rod 280 along the entire surface 216 thereof for adequate capture and fixing of the solid rod 280 with respect to the receiver 20 and the shank 14.

With reference to FIGS. 10-13, the reference numeral 1A generally designates a second embodiment of a non-fusion dynamic stabilization longitudinal connecting member assembly according to the present invention. The connecting member assembly 1A includes an outer, cannulated coil-like connecting member 4A and a substantially cylindrical core or insert 8A, having an outer helical thread 9A, the core being threadably receivable in the coil-like member 4A and fixed thereto at only one end of the core 8A as will be described more fully below. The dynamic connecting member assembly 1A cooperates with at least a pair of polyaxial bone screw assemblies according to the invention, one of such assemblies, generally 10, shown in FIGS. 14-17 and previously described herein with reference to FIGS. 5-9. The closure structure 30 also shown in FIGS. 14-17 and previously described herein with respect to FIGS. 5-7, also cooperates with the connecting member 1A and the bone screw assembly 10 in the manner previously described herein with respect to the connecting member 1. The bone screw assembly 10 and cooperating closure 30, and in particular, the compression structures 24 and 26 bias the retaining and articulating structure 22 into fixed frictional contact with the receiver 20, so as to substantially attach and orient the longitudinal connecting member assembly 1A relative to the vertebra 28 and yet allow for some relative movement of the outer coil-like member 4A with respect to the inner cylindrical core 8A, providing relief (e.g., shock absorption) with respect to flexion, extension and compressive and distractive forces placed on the assembly 1A and two or more connected assemblies 10. The coil-like member 4A is also able to twist or turn with respect to the cylindrical core 8A, providing relief for torsional stresses. However, the inner core 8A does not participate in or provide any means for torsional elasticity or axial compression and distraction along a length of the outer coil 4A.

The longitudinal connecting member assembly 1A, best illustrated in FIGS. 10-13 is elongate, with both the outer coil-like member 4A and the inner core 8A being made from metal, metal alloys, composites or other suitable materials, including plastic polymers, such as ultra-high molecular weight polyethylene (UHMWP) and/or polyetheretherketone (PEEK). Also, in order to result in adequate hardness and low or no wear debris, the member 4A surfaces and the core 8A surfaces may be coated with an ultra thin, ultra hard, ultra slick and ultra smooth coating, such as may be obtained from ion bonding techniques and/or other gas or chemical treatments.

The core 8A illustrated in the drawing figures is solid, elongate cylinder, having a central axis AA. It is foreseen that the core 8A may also be a hollow cylinder. The core 8A includes a smooth cylindrical surface 40A. The core 8A may include a stop or rim 42A integral or fixedly attached to the core 8A at an end 43A thereof. The stop 42A is substantially coaxial with the cylinder 40A. In the embodiment shown, the stop 42A includes a flat abutment surface 44A and an outer cylindrical surface 46A. As will be described in more detail below, the stop 42A may be replaced by an elongate connecting member, such as a solid rod, allowing for more rigid support, and fusion, if desired, along a portion of the spine adjacent to the spine portion receiving dynamic stabilization by the connector 1A.

The helical thread 9A extends radially outwardly from the surface 40A of the inner core 8A and winds about the inner core 8 substantially along a length thereof. The illustrated thread 9A includes an end portion 47A having a thickness and radially length greater than a remainder portion 48A of the thread 9A. The end portion 47A is sized and shaped to have an axial length along the axis AA that corresponds to a width of the receiver 20 that receives and clamps the assembly 1A into engagement with the assembly 10. The core 8A is sized and shaped to attach to the coil-like member 4A at the cylinder end 43A, with the end portion 47A of the thread 9A frictionally engaging the coil-like member 4A as will be described more fully below. Near an opposite end 50A thereof, the core 8A does not include structure for fixed attachment to the coil-like member 4A. The cylindrical surface 40A has a substantially uniform outer radius that is slightly smaller than an inner radius of an internal substantially cylindrical surface 54A of the coil-like member 4A, providing a slight gap 51A about the cylindrical surface 40A, annular in cross-section, located between the cylindrical surface 40A and the surface 54A when the inner core 8A is inserted and threaded into and fully received by the coil-like member 4A. The gap 51A that spans along the length of the cylinder 40A from near the end stop 42A to the end 50A allows for limited sliding, axial (back and forth) movement of the coil-like member 4A with respect to the core 8A, along the axis AA as well as some twisting or torsional movement by the member 4A about the core 8A.

The outer coil-like member 4A is also substantially cylindrical with an external substantially cylindrical surface 52A and the internal substantially cylindrical and smooth surface 54A previously identified herein. The surface 54A defines a bore 56A with a circular cross section, the bore 56A extending completely or substantially through the coil-like member 4A. The member 4A has a substantially flat and annular end surface 58A and a curved or bullet-nosed opposite end 59A. It is noted that in some embodiments, the end surface 59A may also be substantially flat and annular. The bullet-nosed end 59A allows for ease in implanting the assembly 1A, particularly in minimally invasive or less invasive procedures, that may be percutaneous in nature. The member 4A further includes a helical slit 60A that extends therethrough from the external surface 52A to the internal surface 54A and beginning at a location 62A at the end surface 58A and winding along an entire or substantial length of the coil-like member 4A. In the illustrated embodiment 1A, the slit 60A runs to near the bullet nose end 59A. The slit 60A extends through the end surface 58A to allow for threadably mating the thread 9A of the inner core 8A with the slit 60A. The cooperation between the thickened end portion 47A of the thread 9A and the surfaces defining the slit 60A provide a friction or press fit between the inner core 8A and the outer coil-like member 4A, fixing the core 8A to the member 4A near the respective ends 43A and 58A, but allowing for an axial gap or space between the remainder portion 48A of the thread 9A and the surfaces defining the slit 60A. When the inner core 8A is fully assembled within the coil-like member 4A, an outer surface 70A of the thread portion 47A is flush with the outer coil surface 52A. Thus, a bone screw assembly 10 receiving and fixing the dynamic fixation assembly 1A near the stop or rim 42A frictionally engages both the outer surface 52A of the coil-like member 4A and the outer surface 70A of the thread 9A of the inner core 8A. In the illustrated embodiment, the coil-like member internal cylindrical surface 54A is of a slightly greater diameter than an outer diameter of the cylindrical surface 40A, allowing for axially directed sliding movement of the coil-like member 4A with respect to the solid cylinder 40A along the thread portion 48A. It is foreseen that a portion of the cylindrical surface 40A near the end 43A may have a diameter slightly greater than the diameter of a remainder of the cylindrical surface 40A, providing for frictional engagement between the surface 40A and the internal surface 54A of the coil-like member 4A, giving some additional attachment and reinforcement of the friction fit between the thread portion 47A and the member 4A near the end 43A. When the cylindrical inner core 8A is inserted in the coil-like member 4A and the thread portion 47A frictionally engages the coil-like member 4A at the slit 60A, the core 8A extends completely or substantially through the bore 56A along the axis AA and along a substantial length of the coil-like member 4A to near the end surface 59A, with the end surface 50A being near or adjacent the end surface 59A. The coil-like member 4A is not fixed to the solid core 8A at or near the end surfaces 50A and 59A. Also an outer surface 72A of the portion 48A of the thread 9A is not flush with the outer surface 52A of the coil-like member, but rather inset or positioned radially inwardly of the surface 52A, such that when the bone screw assembly 10 frictionally engages the surface 52A, the surface 72A is spaced from the bone screw assembly 10. Furthermore, similar to what was previously described with respect to the connector 1, the bone screw assembly 10 is sized and shaped to frictionally engage the coil-like member 4A without crushing or otherwise frictionally engaging or fixing the coil-like member 4A against the core 8A within a cooperating bone screw assembly 10 located along the coil-like member 4A receiving the portion 48A of the thread 9A, thus allowing for relative movement between the coil-like member 4A and the core 8A.

Figure 13:
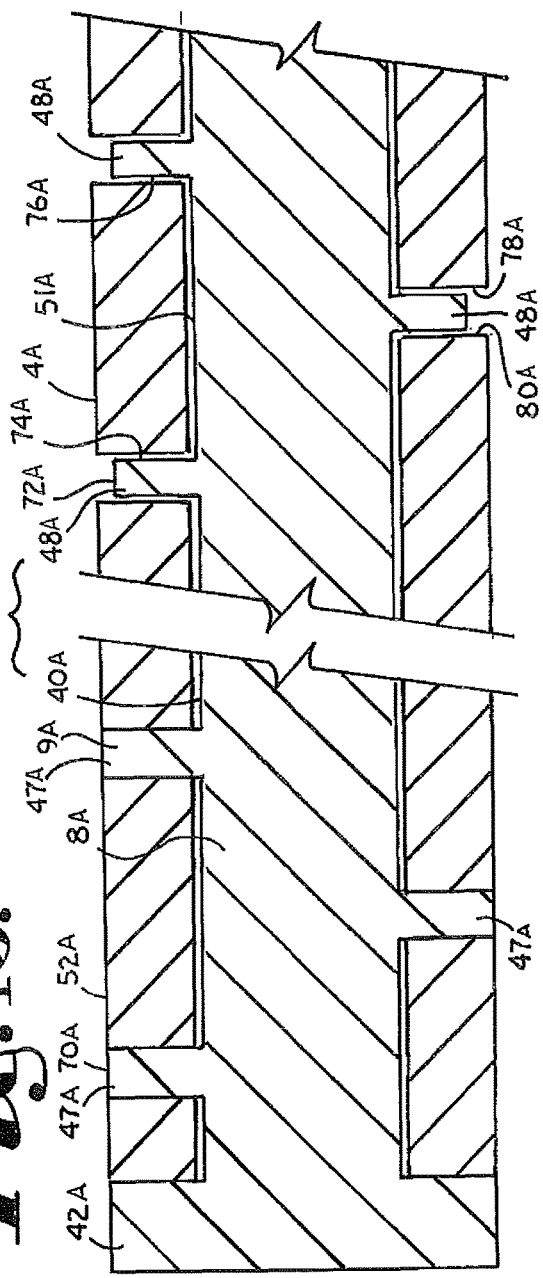
FIG. 13 is an enlarged and partial cross-sectional view taken along the line 13-13 of FIG. 12.
Figure 16:
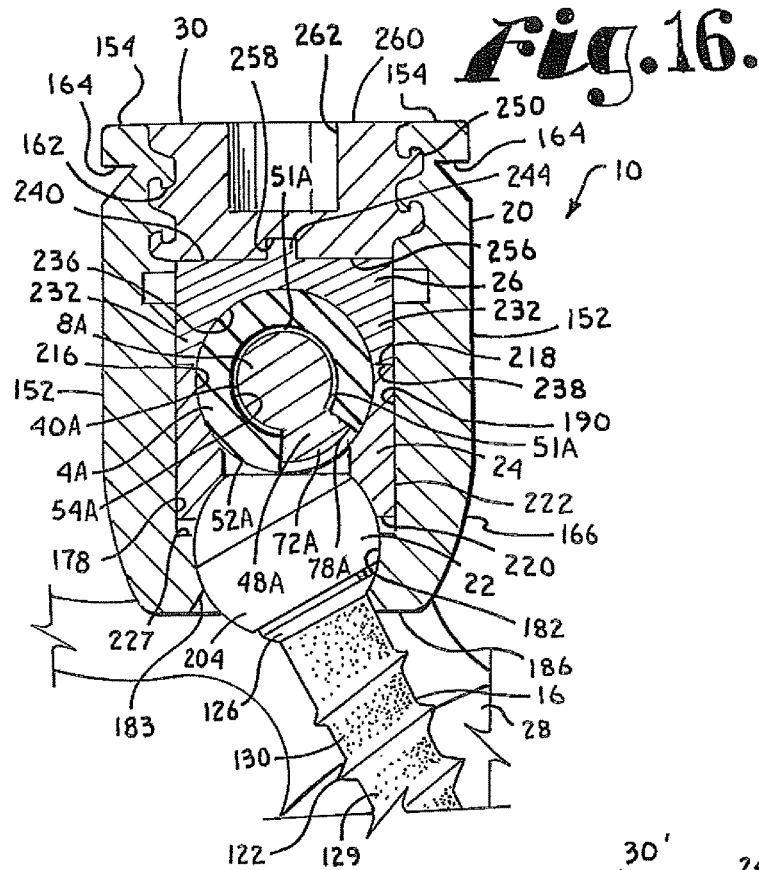
FIG. 16 is an enlarged and partial cross-sectional view taken along the line 16-16 of FIG. 15 and along the line 16-16 of FIG. 12, but shown with the shank in side elevation implanted in a vertebra and disposed at an angle with respect to the receiver.

As shown in the drawing figures, and in particular reference to FIGS. 13 and 16, the substantial portion 48A of the thread 9A of the inner core 8A is sized and shaped such that the thread portion 48A is uniformly spaced from the surfaces defining the helical slit 60A of the coil-like member 4A. In particular, the substantially square thread 9A includes a leading surface 74A and a trailing surface 76A. The coil-like member has surfaces 78A and 80A that form the helical slit 60A. All along the thread portion 48A, the thread surface 74A is spaced from the surface coil surface 78A and the thread surface 76A is spaced from the coil surface 80A. This spacing, along with the gap 51A between the outer cylindrical surface 40A of the thread 9A and the inner surface 54A of the coil-like member 4A, allows for axial and twisting movement of the inner core 8A with respect to the coil-like member 4A until an axial movement or motion is sufficient to cause the surface 74A to abut against the surface 78A and/or the surface 76A to abut against the surface 80A. It is foreseen that the square thread 48A could be V-shaped or some other shape.

For the desired spacial alignment of the thread 9A with respect to the slit 60A to occur, the pitch of the slit 60A is substantially the same as the pitch of the thread 9A of the core 8A. Pitch is the distance measured parallel to the axis AA, between corresponding points on adjacent thread forms in the same axial plane and on the same side of the axis. The amount or degree of pitch of the thread 9A and the slit 60A may be chosen based upon the rigidity or stiffness requirements for the assembly 1A and shock absorption desired. For example, it is noted that increasing the pitch (i.e., forming a more acute angle between the slant of the thread 9A and the slit 60A with respect to the axis AA and therefore increasing the distance between corresponding points on adjacent thread forms in the same axial plane) results in a stiffer assembly with respect to bending and axial displacements. Furthermore, a benefit of increasing pitch is a lessening of impact loading between the thread 9A and the surfaces of the member 4A defining the helical slit 60A. Stated in another way, when there is relative movement between the coil-like member 4A and the core 8A such that surfaces 74A and 76A of the thread portion 48A abut against or make momentary impact with surfaces 78A and 80A defining the slit 60A, when the pitch is greater, the facing surfaces 74A and 78A and also the facing surfaces 76A and 80A slide with respect to one another rather than coming to an abrupt impact as occurs when the pitch is not as great. Therefore, increasing the pitch dampens the jolts of an impact between the surfaces of the thread portion 48A and the surfaces of the member 4A that define the slit 60A, thus improving shock absorption.

It is noted that the inner core 8A may be sized and made from such materials as to provide for a relatively more rigid assembly 1A or a relatively more flexible assembly 1A with respect to flex or bendability along the assembly 1A. Such flexibility therefore may be varied by changing the outer diameter of the inner core 8A and thus likewise changing the diametric size of the coil-like member 4A. Also, it is noted that longer assemblies 1A may need to be stiffer and thus larger in diameter than shorter assemblies 1A. In addition, since the distance between the bone screw assembly heads can vary, the coil-like assembly may need to be more or less stiff.

It is foreseen that in order to keep scar tissue from growing into the coil-like member 4A through the helical slit 60A, an inner or outer sleeve or sheath-like structure may be placed, adhered or otherwise applied to either the external surface 52A or the internal surface 54A of the coil-like member 4A. Such a sheath-like structure would be of a size and shape such that axial movement of the coil-like member 4A is not hindered and thus any relative movement between the coil-like member 4A and the cylindrical core 8 is not hindered or prevented.

The longitudinal connecting member assembly 1A cooperates with the bone screw assembly 10 and the closure structure 30 in the same manner as previously described herein with respect to the longitudinal connecting member assembly 1. With particular reference to FIGS. 10-13, the longitudinal connecting member assembly 1A is first assembled by inserting the inner core 8A into the bore 56A defined by the inner cylindrical surface 54A of the coil-like member 4A. The end 50A of the inner core 8A is placed into the open end 58A of the coil-like member 4A with the thread 9A being received by the slit 60A at the location 62A. The core 8A is then rotated, advancing the thread portion 48A toward the nose 59A until the thread portion 47A engages the surfaces 78A and 80A that form the slit 60A, with the surface 44A of the stop 42A abutting against the end surface 58A of the coil-like member. As illustrated in FIG. 13, the thread portion 47A, having a thickness greater than the portion 48A, frictionally engages the surfaces 78A and 80A at respective surfaces 74A and 76A, fixing the core 8A to the coil-like member 4A near the stop 42A.

The connecting member assembly 1A is eventually positioned in an open or percutaneous manner within the U-shaped channels 156 of two or more bone screw assemblies 10. The second or upper compression structure 24 is then placed in each assembly 10 with the U-shaped seating surface 236 facing the coil-like member 4A. The closure structure 30 is then inserted into and advanced between the arms 152. It is noted that it is also possible to insert the closure structure pre-attached to the upper compression structure with the two parts snapped together. As the closure structure 30 is rotated between the arms 152, the central recess or aperture 258 receives the pin 244 of the compression member 26, centering the member 26 with respect to the receiver 20 and the connecting member assembly 1A. Continued rotation of the closure structure 30 results in engagement between the surfaces 240 and 256, uniformly pressing the compression member 26 against the coil-like member 4A at the seating surface 236 of the compression member 26 and the outer substantially cylindrical, but discontinuous surface 52A of the coil-like member 4A. The coil-like member 4A in turn presses downwardly against the seating surface 216 of the lower compression structure 24, pressing the structure 24 downwardly into engagement with the retaining and articulating structure outer surface 204 to set the angle of articulation of the shank body 16 with respect to the receiver 20.

With particular reference to FIG. 16, the compression structure 26 also presses against the compression structure 24 at the surface 218 as the closure structure is torqued 30, clamping the shank body 16 into a fixed position with respect to the receiver 20. However, the cylindrical surfaces 216 and 236 of the compression structures 24 and 26, respectively, cradle and protect the coil-like member 4A from crushing against the inner core 8A. Thus, although torquing of the closure structure 30 against the compression structure 26 clamps the coil-like member 4A with enough force to keep the member 4A in a fixed position in the receiver 20, the compression structures 24 and 26 allow for maintaining the gap 51A between the cylindrical surface 40A of the core 8A and the coil-like member 4A, and also keep the thread portion 48A spaced from the surfaces 78A and 80A that form the slit 60A and the outer surface 72A of the thread portion 48A spaced from the compression members, such that relative movement between the inner core 8A and the member 4A is possible, along a length of the core 8A having the thread portion 48A thereon.

Figure 17:
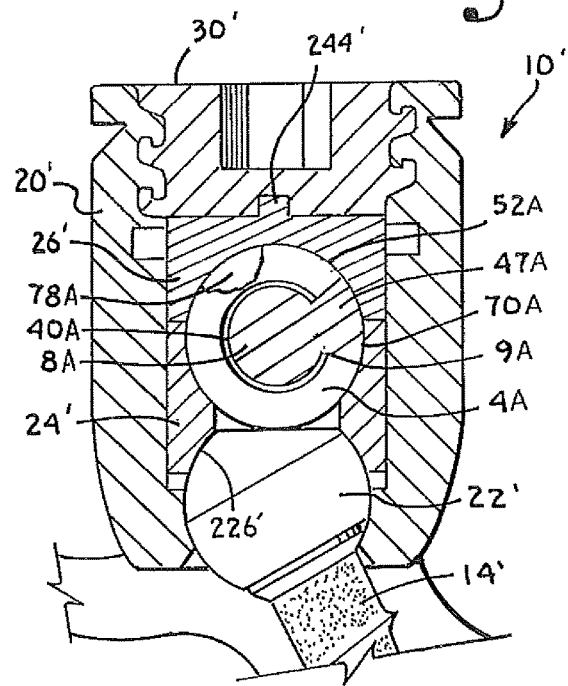
FIG. 17 is an enlarged and partial cross-sectional view, similar to FIG. 16, showing a second bone screw assembly attached to the dynamic fixation assembly of FIG. 1 near an end thereof, along the line 17-17 of FIG. 12, and with a further portion broken away to show detail thereof.

With reference to FIG. 17, a second bone screw assembly 10' is illustrated, attached to the assembly 1A near the end stop 42A at the location of the thicker thread portion 47A. The assembly 10' includes a shank 14', a receiver 20', a retaining and articulating structure 22', a first compression structure 24', a second compression structure 26' and a closure structure 30' the same or substantially similar to the respective shank 14, receiver 20, retaining and articulating structure 22, first compression structure 24, second compression structure 26 and closure structure 30 of the assembly 10, and all other corresponding structure previously described herein with respect to the assembly 10. As illustrated in FIG. 17, the outer surface 70A of the thread portion 47A is flush with the outer surface 52A of the coil-like member 4A. Therefore, the compression structures 24' and 26' engage both the surfaces 52A and 70A when the closure structure 30' engages the receiver 20' and the compression structure 26', fixing both the coil-like member 4A and the inner core 8A within the receiver 20' of the assembly 10'.

If removal of the assembly 1A from any of the assemblies 10 or 10' is necessary, or if it is desired to release the assembly 1A at a particular location, disassembly is accomplished by using the driving tool (not shown) with a star-shaped driving formation on the closure structure 30 internal drive 262 to rotate and remove the closure structure 39 from the receiver 20. Disassembly of the assembly 10 or 10' is accomplished in reverse order to the procedure described previously herein for assembly.

With reference to FIGS. 18-21 an alternative embodiment of a dynamic longitudinal connecting member assembly, generally 301 is illustrated. The connecting member assembly 301 includes an outer, cannulated coil-like connecting member 304 and a substantially cylindrical core or insert 308, having an outer helical thread 309 extending radially from an outer cylindrical surface 340, the core 308 being threadably receivable in the coil-like member 304 and fixed thereto at only one end near an end stop 342, the thread 309 sized and shaped to be received in spaced relation to a helical slit 360 of the coil-like member 304. The dynamic connecting member assembly 301 cooperates with at least a pair of polyaxial bone screw assemblies according to the invention, such as the assembly 10 previously described herein.

The connecting member assembly 301 is substantially similar to the assembly 1A with the exception that the thread 309 is substantially uniform in size and shape along an entire length thereof, having an outer surface 372 that is disposed radially inwardly of an outer surface 352 of the coil-like member 304, similar to the surface 72A of the thread portion 48A of the assembly 1A. Near the end stop 342, the core 308 includes a cylindrical portion 384 of greater diameter than the remaining cylindrical surface 340, the portion 384 sized and shaped to provide a frictional press fit between the coil-like member 304 and the core 308 at only the portion 384, when the core 308 is fully received in the coil-like member 304. Thus, other than at the portion 384, the core cylindrical surface 340 and the thread 309 are in slidable engagement with the coil-like member 304.

It is noted that assemblies 1A, 301 and 10 according to the invention advantageously allow for replacement of the assembly 1A or 301 with other connecting member assemblies (dynamic or rigid) having the same or reduced outer diameter. For example, if it is found that a patient requires a connecting member with additional rigidity, the closure structures 30 may be removed, followed by removal of the upper compression structure 26, followed by removal of the assembly 1A or 301 and then an assembly 1A or 301 may be implanted having a slit with greater pitch but the same outer diameter. Such an assembly may be more rigid, but would be sized and shaped to properly engage both the lower compression structure 24 and the upper compression structure 26 and be cradled, with the outer coil being held rigidly in place thereby. If, it is desired to replace the assembly 1A or 301 with a rigid rod having an outer diameter that is smaller than the outer diameter of the assembly 1A or 301, such a rod may be placed on the lower compression structure 24. Then, an upper compression structure sized and shaped to cooperate with both the rigid rod and the closure structure 30 can be utilized to hold the rigid rod properly centered in place within the receiver 20. The fact that such a rigid rod of reduced diameter would not be closely held by the lower compression structure 24 is not of concern because the upper compression structure in combination with the closure structure 30 provides adequate centering support.

With reference to FIGS. 22-34, the reference numeral 401 generally designates an alternative polyaxial bone screw assembly according to the invention for use with the dynamic stabilization longitudinal connecting member assemblies 1, 1A and 301 previously described herein and the assemblies 1B, 1C, 1D and 1E described below. The bone screw assembly 401 includes a shank 414 that further includes a body 416 integral with an upwardly extending, substantially cylindrical upper end or capture structure 418; a receiver or head 420 having a central axis C; a retaining and articulating structure 422; a first lower compression structure 424 and a second upper compression structure 426. The shank 414, the receiver 420, the retaining and articulating structure 422 and the first compression structure 424 are preferably assembled prior to implantation of the shank body 416 into a vertebra (not shown). The shank 414, the receiver 420 and the retaining and articulating structure 422 are identical or substantially similar to the shank 14, receiver 20 and retaining and articulating structure 22 previously described herein with respect to the bone screw assembly 10 and such discussion is incorporated by reference herein with respect to the assembly 401. The lower compression structure 424 and the upper compression structure 426 are substantially similar to the respective lower compression structure 24 and the upper compression structure 26 of the assembly 10, with the exception that they cooperate with one another in a slidable fashion rather than abut one another. In particular, the upper compression structure 426 is receivable in the lower compression structure 424, with the compression structures cooperating independently with a nested set-screw type closure structure, generally 430, in a manner that will be described in greater detail below.

FIGS. 22-25 show the nested set-screw type closure structure 430 of the invention for capturing the longitudinal connecting member assemblies according to the invention, such as the assembly 1A, within the receiver 420. The closure structure 430 includes an outer fastener 432 and an uploaded set screw 434. The fastener 432 includes a base 436 integral or otherwise attached to a break-off head 438. The base 436 cooperates with the receiver 420 to capture the longitudinal connecting member 1A (or any other longitudinal connecting member according to the invention) within the bone screw receiver 420. The break-off installation head 438 includes an internal drive or aperture 440 sized and shaped for engagement with a tool (not shown) for installing the fastener 432 to the bone screw receiver 420 and there-after separating the break-off head 438 from a respective base 436 when installation torque exceeds selected levels.

The base 436 of the fastener portion 432 is substantially cylindrical, having an axis of rotation D and an external surface 450 having a guide and advancement structure 452 disposed thereon. The guide and advancement structure 452 is matingly attachable to a guide and advancement structure 453 of the bone screw receiver 420. The cooperating guide and advancement structures 452 and 453 can be of any type, including V-type threads, buttress threads, reverse angle threads, or square threads, and are preferably helically wound flange forms that interlock and are splay resistant, and thus do not exert radially outward forces on the arms of the receiver 420, thereby avoiding tendencies toward splaying of the receiver arms when the fastener portion 432 is tightly torqued into the receiver 420.

The fastener portion 432 includes an internal, centrally located bore 454. At the base 436 the bore 454 is substantially defined by a guide and advancement structure, shown in FIG. 24 as an internal V-shaped thread 456. The thread 456 is sized and shaped to receive the threaded set screw 434 therein as will be discussed in more detail below. Although a traditional V-shaped thread 456 is shown, it is foreseen that other types of helical guide and advancement structures may be used. Near a top of the base 436, an abutment shoulder 460, extends uniformly radially inwardly. The abutment shoulder 460 is spaced from the V-shaped thread 456 and sized and shaped to be a stop for the set screw 434, prohibiting the set screw 434 from advancing upwardly out of the base 436. It is foreseen that alternatively, the set screw may be equipped with an outwardly extending abutment feature near a base thereof, with complimentary alterations made in the fastener base 436, such that the set screw 434 would be prohibited from advancing upwardly out of the top of the base 436 due to abutment of such outwardly extending feature against a surface of the base 436.

An inner cylindrical wall 462 separates the abutment shoulder 460 from the thread 456. The cylindrical wall 462 has a diameter equal to or slightly greater than a root or major diameter of the internal thread 456. The wall 462 partially defines a cylindrical space or passage 464 for axial adjustable placement of the screw 434 with respect to the longitudinal connecting member 1A.

The fastener break-off head 438 is integral or otherwise attached to the fastener 432 at a neck or weakened region 466. The neck 466 is dimensioned in thickness to control the torque at which the break-off head 438 separates from the fastener 432. The preselected separation torque of the neck 466 is designed to provide secure engagement between the fastener 432 and the lower compression structure 424 that in turn presses against the retaining and articulating structure 422 that is threadably mated to the shank 414, clamping the shank 414 in a desired angular orientation with respect to the receiver 420 and the longitudinal connecting member 1A. The fastener 432 thus captures the longitudinal connecting member 1A within the receiver 420 before the head 438 separates, by abutting against the lower compression member 512 without making contact with the coil-like member 4A. For example, 120 inch pounds of force may be a selected break-off torque to lock the bone screw shank in place without placing any pressure on the coil-like member 4A. The illustrated internal driving feature 440 of the break-off head 438 enables positive, non-slip engagement of the head 438 by an installation and torquing tool. Separation of the break-off head 438 leaves only the more compact base 436 of the fastener 432 installed in the bone screw receiver 420, so that the installed fastener 432 has a low profile. As will be described in greater detail below, the set screw 434 may then be rotated and moved downwardly into secure engagement with the coil-like member 4A without forcing the coil-like member into contact with the threaded core 8A.

Figure 31:
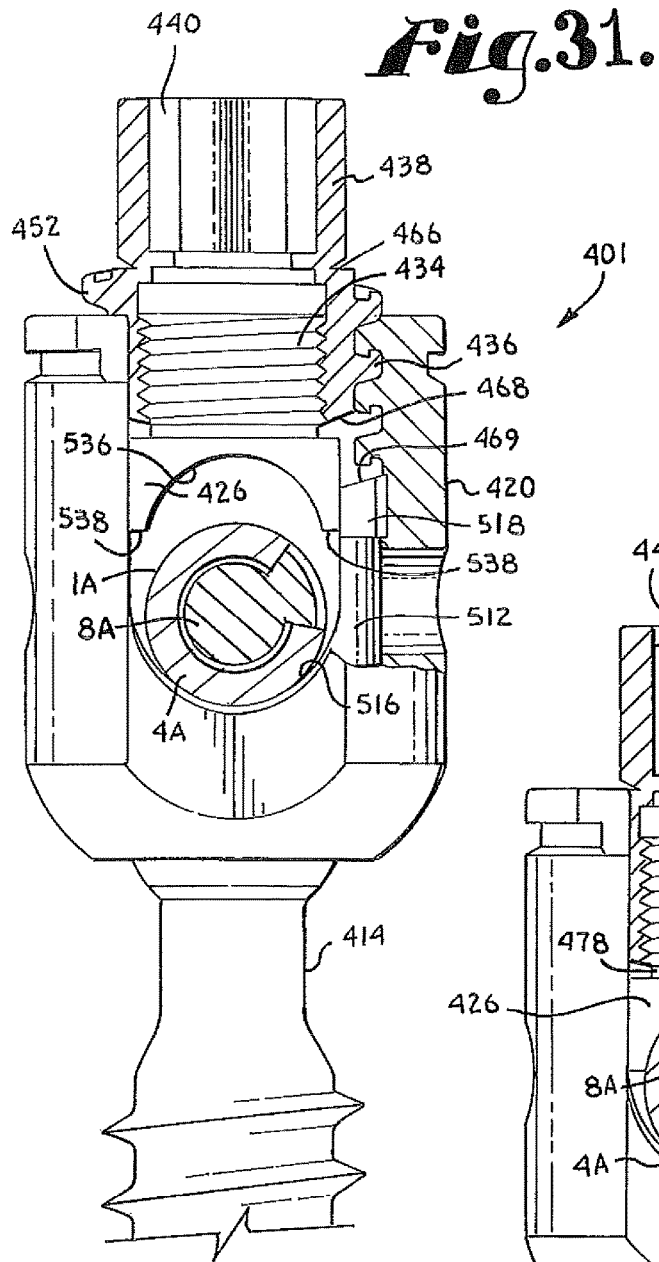
FIG. 31 is an enlarged and partial front elevational view of the assembly of FIG. 22 with portions broken away to show the detail thereof and further showing the upper compression member and closure member partially inserted in the receiver.
Figure 32:
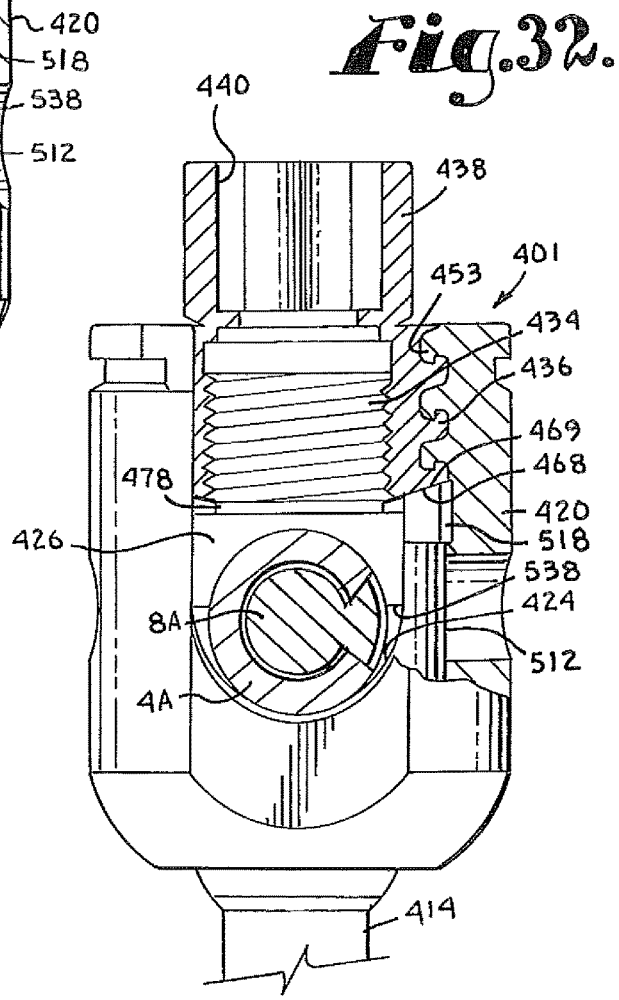
FIG. 32 is an enlarged and partial front elevational view similar to FIG. 31 showing the upper compression member and closure member fully seated in the receiver prior to removal of the closure member break-off head.

The base 436 of the fastener 432 preferably includes a ramped or incline surface or structure 468 for cooperating frictional engagement with an inclined surface 469 of the lower compression structure 424 as best illustrated in FIGS. 31 and 32. Both surfaces 468 and 469 slope downwardly radially from the guide and advancement structure 452 toward the axes C and D when the fastener and compression structures are assembled in the receiver 420. Ramped contact between the fastener 432 and the lower compression structure 424 strengthens the structure 424 and prevents capture of the upper compression structure 426.

The uploadable set screw 434 has a substantially annular and planar top 476 and a substantially annular and planar bottom 477. The screw 434 is substantially cylindrical in shape and coaxial with the fastener 432. The screw 434 includes an outer cylindrical surface 478 disposed near the bottom 477 and a threaded surface 480 extending from the top 476 to the cylindrical surface 478. The v-shaped thread 480 is sized and shaped to be received by and mated with the inner thread 456 of the fastener base 436 in a nested, coaxial relationship.

As illustrated, for example, in FIGS. 24 and 25, The set screw 434 includes a central aperture 486 formed in the top 476 and defined by side walls 488 that define a driving feature similar to but of smaller dimensions than the driving feature 440 of the fastener 432. The driving feature further includes a seating surface or bottom 489, aiding in a positive, non-slip engagement by a set screw installment and removal tool (not shown) that may be inserted through the aperture formed by the driving feature 440 of the fastener 432 and then into the aperture 486 and into engagement with the walls 488 defining the set screw driving feature. A lower central aperture or bore 490 extends between the central aperture 486 and the bottom 477 of the set screw 434. The bore 490 is sized and shaped to receive and hold an upper portion of the upper compression structure 426 as will be described more fully below.

With reference to FIG. 24, the central set screw aperture 486 cooperates with the central internal bore 454 of the fastener 432 for accessing and uploading the set screw 434 into the fastener 432 prior to engagement with the bone screw receiver 420. After the closure structure 430 is inserted and rotated in the bone screw receiver 420, and the break-off head 438 is broken off, the set screw 434 is rotated by a tool engaging the drive feature walls 488 to place the set screw bottom 477 into frictional engagement with the outer coil-like member 4A. Such frictional engagement is therefore readily controllable by a surgeon so that the coil-like member 4A remains in slidable engagement with the thread 9A of the core 8A. Furthermore, if desired, the set screw 434 may be rotated to a further extent to result in pressure being placed on the thread 9A and/or the core 8A by the coil-like member 4A, resulting in a fixed engagement between the set screw, coil and core.

There are circumstances under which it is desirable or necessary to release the longitudinal connecting member 1A from the bone screw assembly 401. For example, it might be necessary for a surgeon to re-adjust components of a spinal fixation system, including the longitudinal connecting member 1A, during an implant procedure, following an injury to a person with such a system implanted. In such circumstances, the tool that engages and rotates the set screw 434 at the driving feature 488 may be used to remove both the set screw 434 and attached fastener base 436 as a single unit, with the set screw 434 contacting and contained within the base 436 by the abutment shoulder 460. Thus, rotation of the set screw tool engaged with the set screw 434 backs both the set screw 434 and the fastener base 436 out of the guide and advancement structure 453 in the receiver 420, thereby releasing the longitudinal connecting member 1A for removal from the bone screw receiver 420 or repositioning of the longitudinal connecting member 1A. It is foreseen that other removal structures such as side slots or other screw receiving and engagement structures may be used to engage the set screw 434 that is nested in the fastener base 436.

With reference to FIGS. 22, 31 and 32, the lower compression structure 424 includes a substantially cylindrical body 510 integral with a pair of upstanding arms 512. The body 510 and arms 512 form a generally U-shaped, open, through-channel 514 having a partially U-shaped bottom seating surface 516 having a radius substantially conforming to an outer radius of the coil-like member 4A and thus configured to operably snugly engage the coil member 4A at the outer surface 52A thereof. The arms 512 disposed on either side of the channel 514 each include a top flanged portion 518, each portion 518 including the ramped or inclined surface 469 previously described herein, sized and shaped to engage the inclined surface 468 of the fastener 432. The compression structure 424 further includes a bottom surface 520 and a substantially cylindrical outer surface 522. An inner cylindrical wall 524 defining a central through-bore extends along a central axis of the compression structure 424 and extends between the seating surface 516 and a substantially spherical surface 526. The surface 526 extends between the inner cylindrical wall 524 and the bottom surface 520. The surface 526 is substantially similar to the spherical surface 226 of the compression structure 24 previously described herein, the surface 526 being sized and shaped to frictionally engage and mate with the outer spherical surface of the retaining and articulating structure 422. The cylindrical surface 522 has an outer diameter slightly smaller than a diameter between crests of the guide and advancement structure 453 of the receiver 420 allowing for top loading of the compression structure 424. The top surface portions 518 disposed on each of the upstanding arms 512 may be snapped into place within the receiver 420 during installation as the arms 512 have sufficient flexibility so that the flanged arms 512 may be pressed toward one another during top loading, with the flanged top portions 518 clearing the guide and advancement structure 453. The lower compression structure 424 is sized such that the compression structure 424 is ultimately received within the cylindrical surface of the receiver 420 below the guide and advancement structure 453 with the flanged top portions 518 received in recesses formed below the guide and advancement structure 453 and the bottom surface 520 being spaced from the receiver base. The receiver 420 fully receives the lower compression structure 424 and blocks the structure 424 from spreading or splaying in any direction. It is noted that assembly of the shank 414 and the retaining structure 422 within the receiver 420, followed by insertion of the lower compression structure 424 into the receiver 420 are assembly steps typically performed at the factory, advantageously providing a surgeon with a polyaxial bone screw with the lower insert firmly snapped into place and thus ready for insertion into a vertebra. The through-channel 514 is sized and shaped such that the upper compression structure 426 is receivable in the channel 514 between opposed upper substantially planar walls 528 that define an upper portion of the channel 514 near the top surfaces 469, each wall 528 extending upwardly to a respective inclined surface 469. Adequate clearance is provided such that the upper compression structure 426 is in slightly spaced or in sliding relationship with the walls 528, allowing for independent movement of the upper compression structure 426 with respect to the lower compression structure 424 and thus into greater or lesser frictional engagement with the coil-like member 4A by pressure being placed directly on the upper compression structure 426 by the set screw 434.

With reference to FIGS. 26-30, the upper or second compression structure 426 includes a body 530 having a pair of downwardly extending legs 532. The body 530 and the legs 532 form a generally U-shaped, open, through-channel having a substantially U-shaped seating surface 536 having a radius substantially conforming to the outer radius of the coil-like member 4A and thus configured to operably snugly engage the coil member 4A at the external surface 52A thereof opposite the seating surface 516 of the lower compression structure 424. The legs 532 each include a bottom surface 538 that is substantially parallel to a planar top surface 540. The compression structure 426 includes a pair of opposed curved outer surfaces 542 substantially perpendicular to the top surface 540 and extending between the top surface 540 and the seating surface 536. The curved surfaces 542 further extend along the legs 532 and terminate at the bottom surfaces 538. A pair of opposed substantially planar outer surfaces 543 are disposed between the curved surfaces 542 and are also disposed substantially perpendicular to the top surface 540, each planar surface 543 extending between the top surface 540 and a respective bottom surface 538.

A pin 544 of substantially circular cross section is disposed centrally on the top surface 540 and extends upwardly therefrom, being sized and shaped to fit within the centrally located lower bore 490 formed in the set screw 434. The pin 544 further includes a substantially cylindrical base 546 and a U-shaped channel 548 formed by a pair of opposed, flanged arms 550 that extend from the base 546 upwardly and substantially parallel to one another. Each of the flanged arms includes a partially conical surface portion 551 and a flat bottom surface 552 that is substantially parallel to the top planar surface 540 of the compression structure body 530. As illustrated in FIGS. 29 and 30, the pin 544 is receivable in the bore 440 with surfaces forming the bore pressing and deforming the flanged arms 550 toward one another as the upper compression structure 426 is pressed against the set screw 434 that has already been up-loaded into a fastener portion 432. Once the conical surface portions 551 clear the bore 440 and enter the set screw aperture 486, the flanged arms 550 return to the original upright and substantially parallel form with the surfaces 552 being in contact with and seated upon a portion of the bottom surface 489 as illustrated in FIG. 30. The flanged arms 550 thus keep the compression structure 426 attached to the set screw 434 and yet rotatable with respect thereto about an axis of rotation E of the cylindrical base 546 of the structure that is coaxial with the axis D of the set screw 434 and fastener 432, providing a centered relationship between the closure structure 430 and the compression structure 426 while allowing the compression structure 426 to freely rotate into a position centered over and in gripping engagement with the longitudinal connecting member 1 when assembled thereon. Furthermore, if removal of the fastener and uploaded set screw is desired, the attached compression structure 426 is advantageously removed along therewith.

With reference to FIGS. 24 and 29-33, in use, the set screw 434 is assembled with the fastener 432 by inserting a set screw tool (not shown) through the bore 454 of the fastener 432 and into the aperture 486 of the set screw 434, with outer features of the tool engaging the inner walls 488 of the set screw 434. The set screw 434 is then uploaded into the fastener 432 by rotation of the set screw 434 with respect to the fastener 432 to mate the set screw thread 480 with the fastener inner thread 456 until the set screw top surface 476 is spaced from the abutment shoulder 460, but substantially nested in the fastener 432, with only the cylindrical surface 478 extending from the fastener base 436. The upper compression structure 424 is then attached to the set screw 434 as previously described with the pin 544 being received by the bore 490 and inserted therethrough until the arms 550 are disposed within the aperture 486, with the lower surfaces 552 of the flanged arms seated on the bottom 489 of the set screw aperture 486, capturing the flanged arms 550 within the aperture 486. The nested assembly shown in FIG. 24 and attached to an upper compression structure as shown in FIGS. 29 and 30 is now pre-assembled and ready for use with a bone screw receiver 420 and cooperating longitudinal connecting member assembly 1A.

Figure 33:
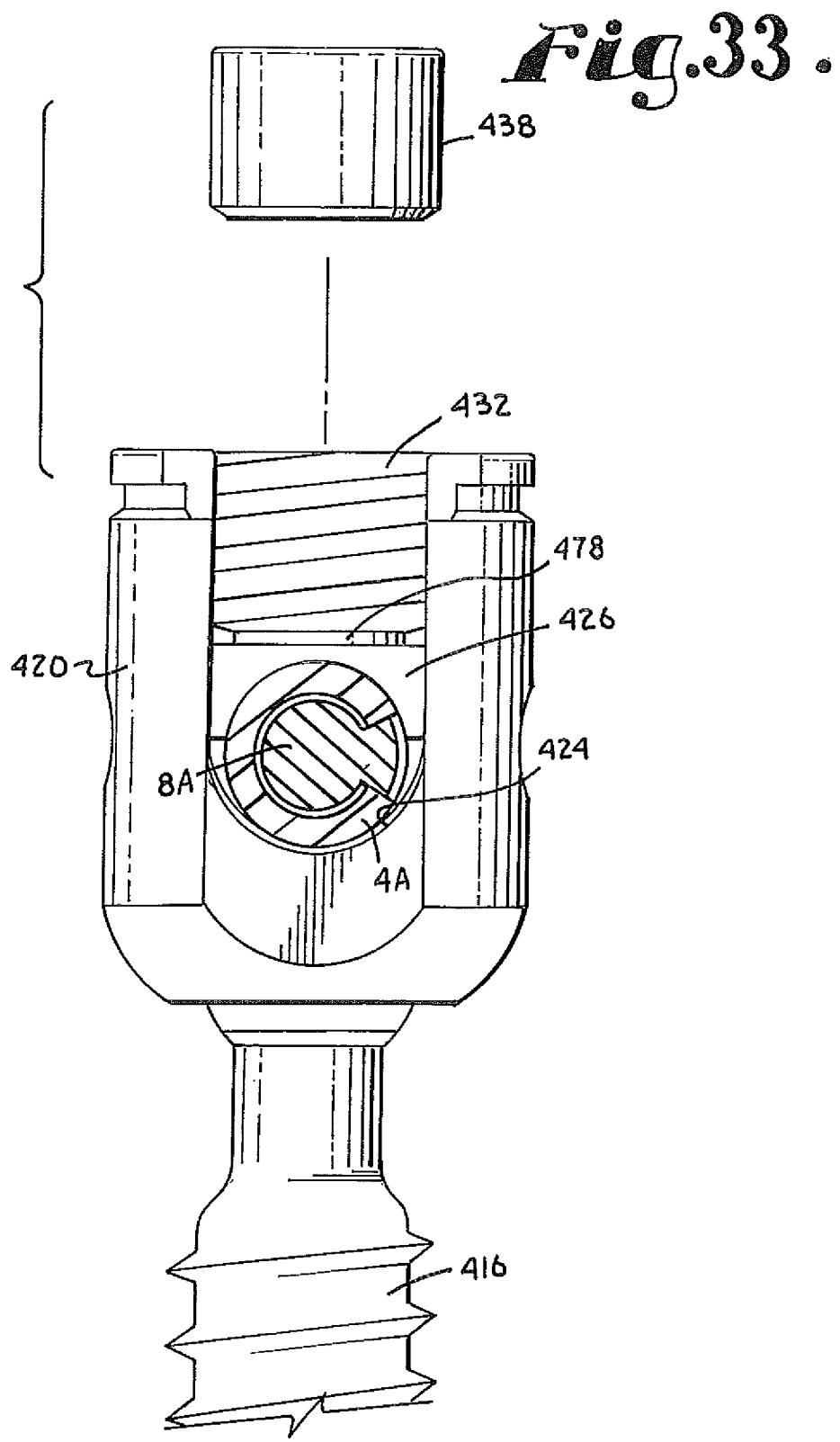
FIG. 33 is an enlarged and partial front elevational view of the assembly of FIG. 22 with portions broken away to show the detail thereof, and further showing the closure member break-off head removed.

With reference to FIGS. 31 and 32, the longitudinal connecting member 1A is eventually placed in the bone screw receiver 420 that has been previously attached to the bone screw shank 414, retaining and articulating structure 422 and lower compression structure 424. A driving tool (not shown) is used to rotate the closure structure by engagement with the drive feature 440 of the break-off head 438, mating the guide and advancement structures 452 and 453. During installation, the fastener inclined surface 468 frictionally engages the inclined surface 469 of the lower compression structure 424, that in turn presses against the retaining and articulating structure 422 that is threadably mated to the capture structure at the shank upper end 418, biasing the retaining and articulating structure 422 into fixed frictional contact with the receiver 420, such that the receiver 420 and the shank 414 can be independently secured at a desired angle with respect to the receiver while the longitudinal connecting member 1A remains movable within the receiver and yet substantially captured between the compression structures 424 and 426. With reference to FIG. 33, the closure structure is rotated until a selected pressure is reached at which time the head 438 breaks off, preferably about 80 to about 120 inch pounds that adequately fixes the bone screw shank 414 with respect to the receiver 420. When the break-off head is removed, the upper compression structure 426 is preferably in contact with the coil-like member 4A, but placing little if any pressure thereon. Then, a set screw driving tool (not shown) is inserted into the drive feature 488 and the set screw 434 is rotated downwardly, into contact with the coil-like member, pressing the coil-like member 4A to a desired amount, preferably enough to substantially attach and orient the longitudinal connecting member assembly 1A relative to the vertebrae and yet allow for some relative movement of the outer coil-like member 4A with respect to the inner core 8A, providing some relief (e.g., shock absorption) with respect to flexion, extension, compressive and distractive forces placed on the assembly 1A and two or more connected bone screw assemblies 401. The coil-like member 4A is also able to twist or turn with respect to the threaded core 8A, providing relief for torsional stresses. However, the solid core 8A does not participate in or provide any means for torsional elasticity or axial compression and distraction along a length of the outer coil 4A. In most instances, the pressure placed on the outer surface of the coil-like member 4A by the set screw 434 is sufficient to clamp the member 4A between the upper and lower compression structures 424 and 426, but not enough to crush or press the coil-like member 4A into fixed engagement with the inner core 8A. The cooperation between the compression members 424 and 426 cradles the assembly 1A therebetween due to the cylindrical inner surfaces thereof, with pressure from the independent set screw 434 upon the upper compression member 426 of preferably approximately only 50 to about 80 inch pounds, that in turn places such pressure on the coil-like member 4A. However, if desired, the set screw 434 may be rotated further, placing additional pressure on the coil-like member and further limiting or blocking relative movement between the core 8A and the coil-like member 4A.

Figure 34:
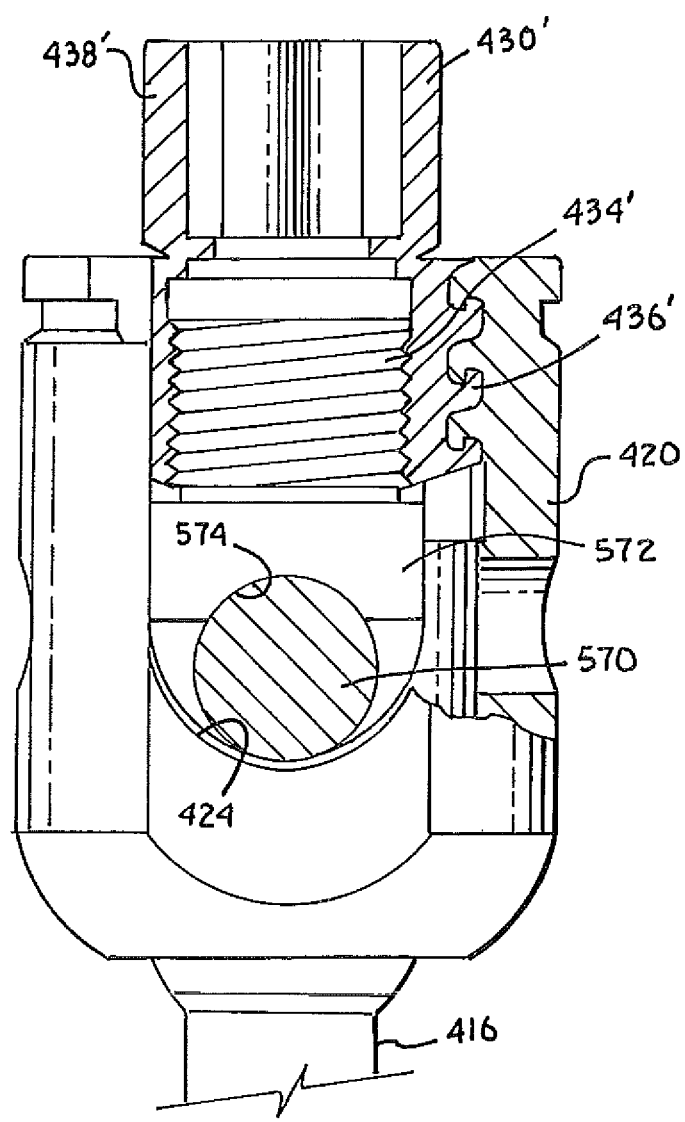
FIG. 34 is an enlarged and partial front elevational view, similar to FIG. 32, with portions broken away to show the detail thereof and further showing the longitudinal connecting member assembly and upper compression structure of FIG. 32 being replaced by a solid rod and a replacement upper compression structure.

The polyaxial bone screw assembly 401 according to the invention advantageously allows for the removal and replacement of the longitudinal connecting member assembly 1A with another longitudinal connecting member having a different overall or outer diameter, utilizing the same receiver 420 and the same lower compression structure 424. For example, as illustrated in FIG. 34, the flexible longitudinal member connecting assembly 1A is removed and replaced by a more rigid assembly, such as a solid rod 570 having an outer diameter that is smaller than an outer diameter of the coil-like member 4A. The rod 570 is inserted into the receiver 420 followed by a cooperating upper compression structure 572 attached to a replacement break-off head closure structure 430' identical to the closure structure 430. The upper compression structure 572 is substantially similar to the compression structure 426 with the exception that the structure 572 is sized and shaped to include a mating surface 574 for closely cooperating with and contacting an outer cylindrical surface of the replacement longitudinal connecting member 570. It is not necessary that the lower compression member 424 be in full contact with the rod 570 for adequate capture and fixing of the solid rod 570 with respect to the receiver 420 and the shank 414 as the rod 570 is centered and received fully by the replacement upper compression structure 572 that also includes a pin (not shown) that is centrally received in the set screw 434' of the replacement closure structure 430'.

With reference to FIGS. 35-39, the reference numeral 1B generally designates a non-fusion dynamic stabilization flexible longitudinal connecting member assembly according to the present invention. The connecting member assembly 1B includes an outer, cannulated coil-like connecting member 4B and a solid cylindrical core 6B receivable in the coil-like member 4B. The cylindrical core 6B generally includes at least one integral support member 8B and one or more adjustable support members 9B slidably mountable on the core 6B. Each support member 8B and 9B includes an outer helically wound projection 12B and 13B, respectively, adapted for cooperation with the coil-like member 4B as will be described more fully below.

Figure 39:
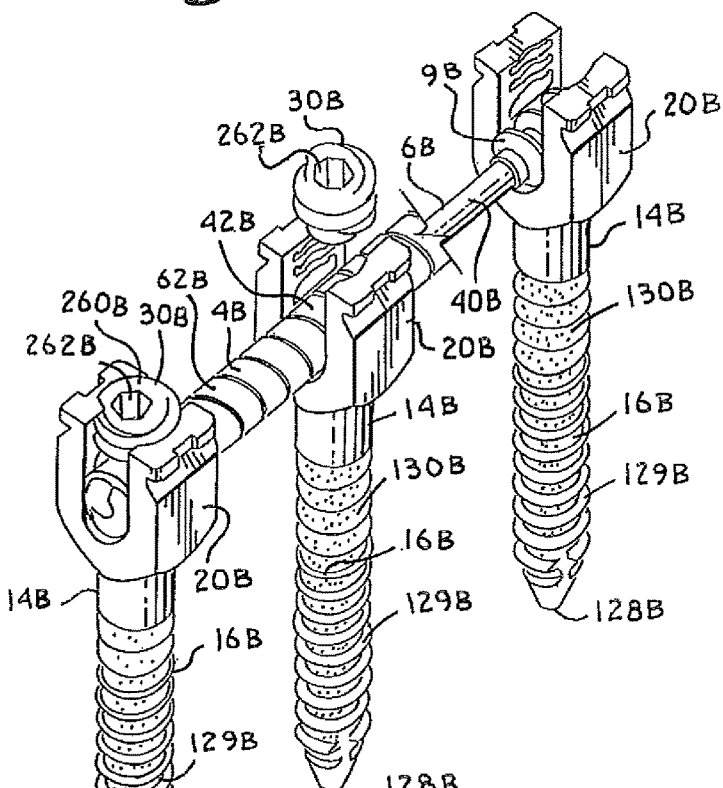
FIG. 39 is a perspective view showing three bone screw assemblies according to FIG. 37 with the dynamic fixation connecting member assembly of FIG. 35 and including two adjustable supports of FIG. 38, with a portion exploded and portions broken away to show detail thereof.
Figure 38:
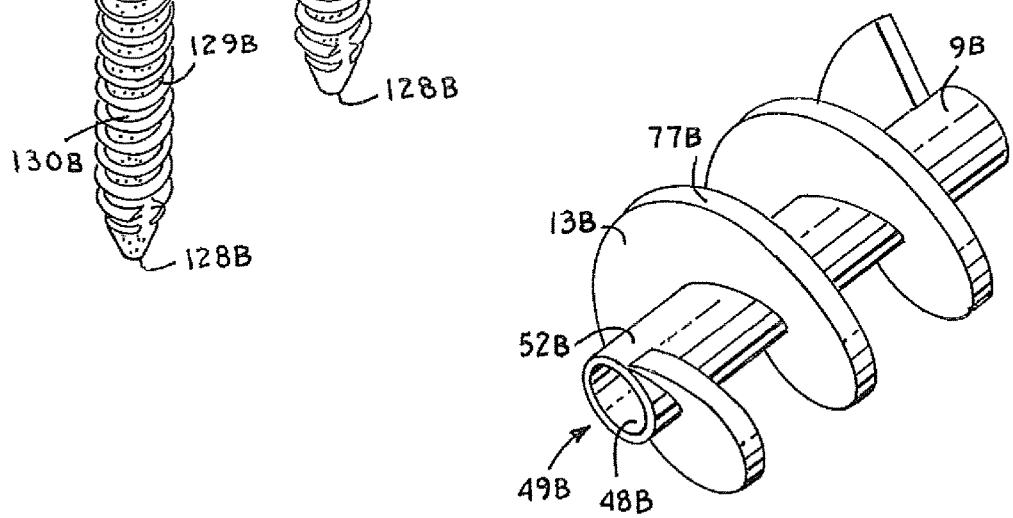
FIG. 38 is an enlarged perspective view of an adjustable support of FIG. 35.

The dynamic connecting member assembly 1B cooperates with at least a pair of polyaxial bone screw assemblies according to the invention, one such assembly, generally 10B, is shown in FIG. 37 and three polyaxial bone screw assemblies 10B are shown in FIG. 39, cooperating with one dynamic connecting member assembly 1B. With reference to FIG. 37, the assembly 10B includes a shank 14B that further includes a body 16B integral with an upwardly extending, substantially cylindrical upper end or capture structure 18B; a receiver or head 20B; and a retaining and articulating structure 22B. The shank 14B, the receiver 20B, and the retaining and articulating structure 22B are preferably assembled prior to implantation of the shank body 16B into a vertebra (not shown).

FIGS. 37 and 39 further show a closure structure 30B of the invention for capturing the longitudinal connecting member assembly 1B within the receiver 20B. Upon installation, which will be described in greater detail below, the closure structure 30B presses against the outer coil-like member 4B and also the helical projection 12B or 13B of a respective support 8B or 9B that is disposed within the coil-like member 4B. Therefore, the flexible coil-like member 4B is not crushed or otherwise deformed by the closure structure 30B. With respect to the support 9B, in addition to supporting the coil-like member 4B, the support 9B allows for relative movement between the core 6B and the portion of the coil-like member 4B supported by the support 9B. The coil-like member 4B supported by the support 8B or 9B in turn presses against the shank upper portion 18B that is threadably mated to the retaining and articulating structure 22B.

As will be discussed in greater detail below, the retaining and articulating structure 22B is in turn pressed into fixed frictional contact with the receiver 20B, so as to substantially attach and orient the longitudinal connecting member assembly 1B relative to the vertebra and yet allow for relative movement of the coil-like member 4B with respect to the inner cylindrical core 6B, providing relief (e.g., shock absorption) with respect to tensile and compressive forces placed on the assembly 1B and two or more connected assemblies 10B. Also, because the adjustable supports 9B are slidably attached to the core 6B, the coil-like member 4B may twist or turn with respect to the cylindrical core 6B, providing relief for torsional stresses. The solid inner core 6B, however, does not participate in or provide any means for torsional elasticity or axial compression and distraction along a length of the outer coil-like member 4B. Furthermore, the receiver 20B, the shank 14B, and the retaining and articulating structure 22B cooperate in such a manner that the receiver 20B and the shank 14B can be secured at any of a plurality of angles, articulations or rotational alignments relative to one another and within a selected range of angles both from side to side and from front to rear, to enable flexible or articulated engagement of the receiver 20B with the shank 14B until both are locked or fixed relative to each other. Alternatively, it is foreseen that the connecting assembly 1B may be inserted into a receiver for a hook or into a receiver that is fixed in position with respect to a bone screw shank, such as a bone screw receiver with an integral shank extending therefrom, or within a receiver with limited angular movement with respect to the shank, such as a hinged connection.

The longitudinal connecting member assembly 1B, illustrated in FIGS. 35-38, is elongate, with the outer coil-like member 4B being made from metal or metal alloy or other suitable materials, including plastics and composites; and the solid inner cylindrical core 6B, and the supports 8B and 9B also being made from metal, metal alloy, plastic or composite material. In order to reduce the production of micro wear debris, that in turn may cause inflammation, it is possible to make the coil-like member 4B from a different material than the core 6B. For example, the coil-like member 4B may be made from a metallic material, such as titanium, while the core member 6B and attached support 8B may be made from polyethylene, such as an ultra high molecular weight polyethylene. Also, it may be desirable to coat the components with thin, hard, super-slick and super-smooth substances or otherwise design the support 9B such that wear debris does not occur between the support 9B and the core 6B. Such combinations result in lower friction between the components 4B, 6B, 8B and 9B, and thus result in lower wear. Alternatively, the core may be made from metal and the coil-like member made from some other material. Another alternative is to coat either the coil-like member 4B or the core 6B with a material other than metal such that adjacent, sliding surfaces are not both metallic. Such metal to non-metal cooperation desirably results in at most, minor amounts of particulate matter formed between cooperating surfaces of the coil-like member 4B, the core 6B and the supports 8B and 9B.

With reference to FIGS. 35-39, the core 6B is solid and elongate, having a central axis AB and a smooth cylindrical surface 40B. The support 8B is integral or otherwise fixedly attached to the core 6B at the cylindrical surface 40B. In the illustrated embodiment of the assembly 1B shown in FIGS. 35-39, that is designed for use with three bone screw assemblies 10B, the support 8B that is integral to the core 6B is at a location 42B disposed substantially centrally between an end 44B and an opposite end 45B of the elongate core 6B. It is noted however, that the integral or fixed support 8B may be at any location along the axis AB. For example, the integral support 8B is typically located near the end 44B or the end 45B of the core (not shown) when only two bone screw assemblies 10B are used to hold a connecting assembly 1B. It may also be desirable to have the fixed support 8B be near the end 44B or the end 45B when a longer assembly 1B is implanted using three or more bone screw assemblies. Thus the fixed or integral support 8B may be at any location along a length of the core 6B, providing support for the coil-like member 4B at a particular bone screw assembly 10B, the surgeon then readily adjusting the location of any other slidingly mountable support 9B based upon the location or locations of the other bone screw assemblies 10B being used to hold the connecting member assembly 1B in place.

The helical projections 12B and 13B of the respective supports 8B and 9B are sized and shaped to extend radially from the cylindrical surface 40B and wind about the surface 40B along the axis AB. An axially directed length L of each helical form or projection 12B and 13B is sized to fit partially or completely within the receiver 20B of the bone screw assembly 10B, providing stability to a portion of the coil-like member 4B that is at least partially received within the receiver 20B and pressed upon by the closure structure 30B. The projections 12B and 13B are sized and shaped to cooperate with the coil-like member 4B in size and helical pitch, extending radially into a helical slit of the member 4B as will be described in greater detail below.

With respect to the support 9B, an inner cylindrical wall 48B defines a through-bore 49B sized and shaped to receive the core 6B and slidingly mate with the outer cylindrical surface 40B thereof. The support 9B has an outer cylindrical surface 52B from which the helical projection 13B extends. The integral support 8B also includes an outer cylindrical surface 54B from which the helical projection 12B extends. The cylindrical surfaces 52B and 54 are both smooth and identical or substantially similar in outer radius and diameter. The radii of the cylindrical surfaces 52B and 54B are slightly smaller than an inner radius of an inner surface 55B of the coil-like member 4B, providing for sliding engagement between the surfaces 52B, 54B and the inner surface 55B. Furthermore the cylindrical surface 40B of the core 6B has a substantially uniform outer radius that is slightly smaller than the radii of the surfaces 52B and 54B, providing a gap of annular cross-section between the surface 40B and the inner surface 55B when the core 6B is inserted in the coil-like member 4B and fully received in the coil-like member 4B. Thus, with the exception of the one location wherein the fixed support 8B engages the coil-like member 4B within a bone screw assembly 10B, the core 6B can move relative to the coil-like member 4B along the axis AB, including the portions of the core 6B within bone screw assemblies 10B in which the coil-like member 4B is supported by a sliding, adjustable support 9B. Twisting or torsional movement of the coil-like member 4B is possible between bone screw assemblies 10B, with both the support 8B and the support or supports 9B fixing the coil-like member 4B within a receiver 20B. However, because of the helically wound nature of the supports 8B and 9B, the coil-like member 4B is not crushed by a closure structure 30B pressing thereon.

The coil-like member 4B is substantially cylindrical with an outer substantially cylindrical surface 62B and the inner substantially cylindrical and smooth surface 55B previously identified herein. The surface 55B defines a bore 66B with a circular cross section, the bore 66B extending completely through the coil-like member 4B. The member 4B has an end surface 68B and an opposite end surface 69B. The member 4B further includes a helical slit 72B that extends therethrough from the outer surface 62B to the inner surface 55B and beginning near the end surface 68B and winding along an entire length of the coil-like member 4B to near the end surface 69B. Alternatively, it is foreseen that the slit 72B may extend through one or both of the end surfaces 68B and 69B. A width measured across the slit 72B is only slightly larger than a width of the helical projections 12B and 13B, such that when the coil-like member 4B engages the supports 8B and 9B, the respective projections 12B and 13B snugly fit with the member 4B by extending there into at the slit 72B, with respective end surfaces 76B and 77B of the projections 12B and 13B being substantially flush with the outer cylindrical surface 62B of the member 4B.

When the cylindrical core 6B is inserted in the coil-like member 4B the member 4B is rotated about the core 6B at the fixed support 8B until the core 6B extends completely through the bore 66B along the axis AB and substantially along an entire length of the coil-like member 4B as shown in FIG. 36. Initially, the coil-like member 4B is only attached to the core 6B by the projection 12B of the support 8B extending into the slit 72B. The member 4B is not otherwise fixedly attached to the solid core 6B. A support 9B may then be rotated about the core 6B with the projection 13B being fed through the slit 72B until a desired location of the support 9B is reached along the axis A corresponding to a location of a bone screw assembly 10B relative to the bone screw assembly 10B cooperating with the coil-like member 4B at the support 8B. Any additional supports 9B (for supporting the member 4B at any additional bone screw assemblies 10B) are fed into the coil-like member in the same manner until such supports 9B are at desired locations along the coil-like member 4B.

It is noted that the core 6B may be sized and/or made from such materials so as to provide for a relatively rigid assembly or a relatively flexible assembly with respect to flex or bendability along the assembly 1B. Such flexibility therefore may be varied by changing the outer diameter of the core 6B and thus likewise changing the diametric size of the coil-like member 4B or by changing the material from which the core 6B and/or coil-like member 4B are made. Also, it is noted that longer assemblies 1B may need to be stiffer and thus larger in diameter than shorter assemblies 1B. The flexibility of the assembly 1B may also be varied by varying the pitch of the helical slit 72B.

It is foreseen that in order to keep scar tissue from growing into the coil-like member 4B through the helical slit 72B, an inner or outer sleeve or sheath-like structure may be placed, adhered or otherwise applied to either the outer surface 62B or the inner surface 55B of the coil-like member 4B. Such a sheath-like structure would be of a size and shape such that axial movement of the coil-like member 4B is not hindered and thus any relative movement between the coil-like member 4B and the cylindrical core 6B is not hindered or prevented. Such a sheath-like structure could also capture any wear debris.

The shank 14B of the bone screw assembly 10B, best illustrated in FIG. 37, is elongate, with the shank body 16B having a helically wound bone implantable thread 124B extending from near a neck 126B located adjacent to the capture structure 18B to a tip 128B of the body 16B and extending radially outward therefrom. During use, the body 16B utilizing the thread 124B for gripping and advancement is implanted into a vertebra leading with the tip 128B and driven down into the vertebra with an installation or driving tool (not shown), so as to be implanted in the vertebra to near the neck 126B. The shank 14B has an elongate axis of rotation generally identified by the reference letter BB.

To provide a biologically active interface with the bone, an outer surface 129B of the shank body 16B that includes the thread 124B and extends between the neck 126B and the tip 128B is coated, perforated, made porous or otherwise treated 130B. The treatment 130B may include, but is not limited to a plasma spray coating or other type of coating of a metal or, for example, a calcium phosphate; or a roughening, perforation or indentation in the surface 129B, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

The neck 126B of the shank 14B extends axially outward and upward from the shank body 16B. The neck 126B is of reduced radius as compared to an adjacent top 132B of the body 16B. Further extending axially and outwardly from the neck 126B is the capture structure 18B that provides a connective or capture apparatus disposed at a distance from the body top 132B and thus at a distance from the vertebra when the body 16B is implanted in the vertebra. The capture structure 18B is configured for connecting the shank 14B to the receiver 20B and capturing the shank 14B in the receiver 20B. The capture structure 18B has an outer substantially cylindrical surface having a helically wound guide and advancement structure thereon which in the illustrated embodiment is a V-shaped thread 136B extending from near the neck 126B to adjacent to a seating surface 138B. Although a simple thread 136B is shown in the drawings, it is foreseen that other structures including other types of threads, such as buttress, square and reverse angle threads, and non threads, such as helically wound flanges with interlocking surfaces, may be alternatively used in alternative embodiments of the present invention.

The shank 14B further includes a tool engagement structure 140B disposed near a top end surface 142B thereof for engagement of a driving tool (not shown). The driving tool is configured to fit about the tool engagement structure 140B so as to form a socket and mating projection for both driving and rotating the shank body 16B into the vertebra. Specifically in the embodiment shown in FIG. 37, the tool engagement structure 140B is in the shape of a hexagonally shaped extension head coaxial with both the threaded shank body 16B and the threaded capture structure 18B.

The top end surface 142B of the shank 14B is preferably curved or dome-shaped as shown in the drawings, for positive engagement with the longitudinal connecting assembly 1B, when the bone screw assembly 10B is assembled, as shown in FIG. 39 and in any alignment of the shank 14B relative to the receiver 20B. In certain embodiments, the surface 142B is smooth. While not required in accordance with the practice of the invention, the surface 142B may be scored or knurled to further increase frictional engagement between the surface 142B and the assembly 1B.

The shank 14B shown in the drawings is cannulated, having a small central bore 144B extending an entire length of the shank 14B along the axis BB. The bore 144B is of circular cross-section and has a first circular opening 146B at the shank tip 128 and a second circular opening 148B at the top surface 142B. The bore 144B is coaxial with the threaded body 16B and the capture structure outer surface. Particularly useful in minimally and less invasive surgery, the bore 144B provides a passage through the shank 14B interior for a length of wire (not shown) inserted into the vertebra prior to the insertion of the shank body 16B, the wire providing a guide for insertion of the shank body 16B into the vertebra.

Also with reference to FIGS. 37 and 39, the receiver 20B includes a base 150B integral with a pair of opposed upstanding arms 152B that extend from the base 150B to a top surface 154B. The arms 152B form a U-shaped cradle and define a U-shaped channel 156B between the arms 152B and include an upper opening 157B and a lower seat 158B having substantially the same radius as the outer coil-like member 4B of the longitudinal connecting member assembly 1B for operably snugly receiving the member assembly 1B.

Each of the arms 152B has an interior surface that defines an inner cylindrical profile and includes a partial helically wound guide and advancement structure 162B. In the illustrated embodiment, the guide and advancement structure 162B is a partial helically wound flangeform configured to mate under rotation with a similar structure on the closure member 30B, as described more fully below. However, it is foreseen that the guide and advancement structure 162B could alternatively be a buttress thread, a square thread, a reverse angle thread or other thread like or non-thread like helically wound advancement structures for operably guiding under rotation and advancing the closure 30B downward between the arms 152B and having such a nature as to resist splaying of the arms 152B when the closure 30B is advanced into the U-shaped channel 156B.

Each of the arms 152B includes a V-shaped-like undercut tool engagement groove 164B formed on a substantially planar outer surface 166B thereof which may be used for holding the receiver 20B with a holding tool (not shown) having projections that are received within the grooves 164B during implantation of the shank body 16B into the vertebra. The grooves 164B may also cooperate with a holding tool during bone screw assembly and during subsequent installation of the connecting member 1B and closure 30B. It is foreseen that tool attachment receiving grooves or apertures may be configured in a variety of sizes and shapes, including radiused, and be disposed at other locations on the arms 152B.

Communicating with the U-shaped channel 156B and located within the base 150B of the receiver 20B is a chamber or cavity 178B partially defined by an inner substantially spherical seating surface 182B, the cavity 178B opening upwardly into the U-shaped channel 156B. The base 150B further includes a restrictive neck 183B adjacent the seating surface 182B. The neck 183B defines an opening or bore communicating with the cavity 178B and a lower exterior 186B of the base 150B. The neck 183B is conically counterbored or beveled to widen the angular range of the shank 14B. The neck 183B is sized and shaped to be smaller than a radial dimension of a fixed or fully expanded retaining and articulating structure 22B so as to form a restriction at the location of the neck 183B relative to the retaining and articulating structure 22B, to prevent the structure 22B from passing from the cavity 178B and out into the lower exterior 186B of the receiver 20B when the retaining and articulating structure 22B is seated on the seating surface 182B. It is foreseen that the retaining and articulating structure could be compressible (such as where such structure has a missing section) and could be up-loaded through the neck 183B and then allowed to expand and fully seat in the spherical seating surface 182B. It is further noted that a retaining and articulating structure may or may not articulate with respect to the receiver, but rather be in a collet or ring shape that is fixed or stationary with respect to the receiver and articulates with respect to the shank.

In the embodiment shown, the retaining and articulating structure 22B has an operational central axis that is the same as the elongate axis BB associated with the shank 14B. The retaining and articulating structure 22B has a central bore 190B that passes entirely through the structure 22B from a top surface 192B to a bottom surface 194B thereof. An inner cylindrical surface defines a substantial portion of the bore 190B and has a helically wound guide and advancement structure thereon as shown by a v-shaped helical rib or thread 198B extending from adjacent the top surface 192B to near the bottom surface 194B. Although a simple helical rib 198B is shown in the drawings, it is foreseen that other helical structures including other types of threads, such as buttress, square and reverse angle threads, and non threads, such as helically wound flanges with interlocking surfaces, may be alternatively used in an alternative embodiment of the present invention. Also, non-helical spline capture designs could be used. The inner thread 198B is configured to mate under rotation with the capture structure outer surface guide and advancement structure or thread 136B.

The illustrated retaining and articulating structure 22B has a radially outer partially spherically shaped surface 200B sized and shaped to mate with the partial spherically shaped seating surface 182B of the receiver and having a radius approximately equal to the radius associated with the surface 182B. The retaining and articulating structure radius is larger than the radius of the neck 183B of the receiver 20B. Although not required, it is foreseen that the outer partially spherically shaped surface 200B may be a high friction surface such as a knurled surface, a shot-pinging surface, sand-blasted surface or the like.

With reference to FIGS. 37 and 39, the closure structure 30B can be any of a variety of different types of closure structures for use in conjunction with the present invention with suitable mating structure on the upstanding arms 152B of the receiver 20B. The closure structure 30B is rotatable between the spaced arms 152B. It is foreseen the closure structure could be slidingly side-loading. The illustrated structure closure structure 30B is substantially cylindrical and includes an outer helically wound guide and advancement structure in the form of a flange form 250B. The illustrated guide and advancement structure 250B operably joins with the guide and advancement structure 162B disposed on the interior of the arms 152B. The guide and advancement structure 250B utilized in accordance with the present invention may take the forms described in Applicant's U.S. Pat. No. 6,726,689, which is incorporated herein by reference. It is also foreseen that according to the invention the guide and advancement structure 250B could alternatively be a buttress thread, a square head, a reverse angle thread or other thread like or non-thread-like helically wound advancement structure for operably guiding under rotation and advancing the closure structure 30B downward between the arms 152B and having such a nature as to resist splaying of the arms 152B when the closure structure 30B is advanced into the U-shaped channel 156B. Again, the closure could be a side-loading wedge-like structure with a radiused bottom.

The closure structure 30B includes a lower substantially planar surface 256B. The surface 256B frictionally engages both the coil-like member 4B and a surface 76B or 77B of a respective support 8B or 9B when rotated between the arms 152B and fully mated with the receiver 20B. The closure structure 30B has a top surface 260B having an internal drive in the form of an aperture 262B, illustrated as a hex-shaped inner drive. A driving tool (not shown) sized and shaped for engagement with the internal drive 262B is used for both rotatable engagement and, if needed, disengagement, of the closure 30B from the arms 152B. Although a hex-shaped internal drive 262B is shown in the drawings, the tool engagement structure may take a variety of tool-engaging forms and may include but is not limited to a star-shaped internal drive, for example, sold under the trademark TORX, or more than one aperture of various shapes. It is also foreseen that the closure structure 30B may alternatively include a break-off head designed to allow such a head to break from a base of the closure at a preselected torque, for example, 80 to 140 inch pounds. Such a closure structure would also include a base having an internal drive to be used for closure removal.

During installation, the lower surface 256B engages both the coil-like member 4B and the projections 12B or 13B of a respective support 8B or 9B of the connecting assembly 1B. The closure structure 30B is rotated, using a tool engaged with the inner drive 262B until a selected pressure is reached at which point the longitudinal connecting assembly 1B is urged toward, but not completely to the lower seat 158B of the channel 156B. In turn, the coil-like member 4B and cooperating support 8B or 9B press directly against the upper surface 142B of the shank 14B. The pressure placed on the assembly 1B by the closure structure 30B is sufficient to clamp the member 4B between the structure 30B and the shank 14B, but the flexible coil-like member 4B is not crushed or otherwise deformed because of the support provided by the projection 12B or 13B, with such projection directly resisting the clamping pressure as the projection 12B or 13B is flush with an outer surface of the coil-like member 4B.

In use, prior to the polyaxial bone screw assembly 10B being implanted in a vertebra, the retaining and articulating structure 22B is typically first inserted or top-loaded, into the receiver U-shaped channel 156B, and then into the cavity 178B to dispose the structure 22B adjacent the inner seating surface 182B of the receiver 20B. The shank capture structure 18B is preloaded, inserted or bottom-loaded into the receiver 20B at the neck bore 183B. The retaining and articulating structure 22B, now disposed in the receiver 20B is coaxially aligned with the shank capture structure 18B so that the helical v-shaped thread 136B rotatingly mates with the thread 198B of the retaining and articulating structure 22B. The shank 14B and/or the retaining and articulating structure 22B are rotated to fully mate the structures 136B and 198B, fixing the capture structure 18B to the retaining and articulating structure 22B. At this time the shank 14B is in slidable and rotatable engagement with respect to the receiver 20B, while the retaining and articulating structure 22B and the lower aperture or neck 183B of the receiver 20B cooperate to maintain the shank body 16B in rotational relation with the receiver 20B. The shank body 16B can be rotated through a substantial angular rotation relative to the receiver 20B, both from side to side and from front to rear so as to substantially provide a universal or ball joint wherein the angle of rotation is only restricted by engagement of the neck 126B of the shank body 16B with the neck 183B of the receiver 20B.

The assembly 10B is then typically screwed into a vertebra by rotation of the shank 14B using a driving tool (not shown) with a socket that operably drives and rotates the shank 14B by engagement thereof with the shank at the tool engagement structure 140B. It is foreseen that in other embodiments according to the invention, the hex-shaped driving formation 140B may be replaced by other types of outer or inner tool engaging formations or recesses. The retaining structure and the shank may also be crimped together so as to not come apart with rotation or a one-way unlocking thread form could be used.

At least two and up to a plurality of bone screw assemblies 10B are implanted into vertebrae for use with the longitudinal connecting member assembly 1B. Each vertebra may be pre-drilled to minimize stressing the bone. Furthermore, when minimally invasive surgical techniques are followed and a cannulated bone screw shank is utilized, each vertebra will have a guide wire or pin (not shown) inserted therein that is shaped for the bone screw cannula 144B of the bone screw shank and provides a guide for the placement and angle of the shank 14B with respect to the vertebra. A further tap hole may be made and the shank body 16B is then driven into the vertebra by rotation of the driving tool (not shown).

With particular reference to FIG. 37, the longitudinal connecting member assembly 1B is assembled by inserting the core 6B into the bore 66B defined by the inner cylindrical surface 55B of the coil-like member 4B. The end 44B of the core 6B is placed into the open end 69B of the coil-like member 4B and the member 4B is moved in an axial direction AB toward the fixed support 8B. When the support 8B abuts the end 69B, the coil-like member 4B is rotated with respect to the core 6B, with the projection 12B extending into the slit 72B and the coil-like member 4B winding about the projection 12B. Rotation of the coil-like member 4B with respect to the core 6B is continued until the fixed support 8B is at a desired location and the core 6B is substantially received within the coil-like member 4B along an entire length thereof. The location 42B of the support 8B along the core 6B corresponds to a location of a bone screw assembly 10B that has been implanted. An adjustable support 9B is then inserted onto the core 6B at either end 44B or 45B, depending upon the relative location of a second bone screw assembly 10B that has been implanted. The adjustable support 9B slidingly mounts on the core 6B and is then rotated such that the projection 13B is guided into the slit 72B and wound therethrough, with the outer surface 77B flush with the outer surface 62B of the coil-like member 4B. The support 9B is rotated until the support is at a distance from the support 8B that corresponds to a distance between two implanted bone screw assemblies 10B. If the assembly 1B is to be connected to more than two bone screw assemblies 10B, additional supports 9B are mounted on the core 6B and rotated within the coil-like member 4B in similar fashion. A tool (not shown) sized and shaped to engage the support 9B within the bore 66B is utilized to rotate the supports 9B.

The connecting member assembly 1B is eventually positioned within the U-shaped channels 156B of two or more bone screw assemblies 10B with the supports 8B and 9B located within the receivers 20B. The closure structure 30B is then inserted into and advanced between the arms 152B. As the closure structure 30B is rotated between the arms 152B, the surface 256B makes contact with the coil-like member 4B outer surface 62B and either the outer surface 76B of the projection 12B or the outer surface 77B of the projection 13B uniformly pressing the assembly 1B against the shank top surface 142B, pressing the retaining and articulating structure outer surface 200B against the seating surface 182B to set the angle of articulation of the shank body 16B with respect to the receiver 20B. However, the supports 8B and 9B protect the coil-like member 4B from being deformed and thus, at the support 9B, the core 6B remains in sliding engagement with the support 9B.

If removal of the assembly 1B from any of the assemblies 10B is necessary, or if it is desired to release the assembly 1B at a particular location, disassembly is accomplished by using the closure driving tool (not shown) on the closure structure internal drive 262B to rotate and remove the closure structure 30B from the receiver 20B. Disassembly of the assembly 10B is accomplished in reverse order to the procedure described previously herein for assembly. It is foreseen that the assembly could use fixed integral bone anchors, such as screws and hooks.

With reference to FIGS. 40-42, a fifth embodiment of a dynamic longitudinal connecting member assembly according to the invention, generally 1C, is substantially identical to the assembly 1 illustrated in FIGS. 1-4, with the exception that the stop 42 is replaced by a connecting member having a solid outer surface illustrated by a rod 42C. In particular, the assembly 1C includes an outer coil-like member 4C and an inner solid cylindrical core 8C identical or substantially similar to the respective coil-like member 4 and the inner core 8 of the connecting member assembly 1 previously described herein. Therefore details of the coil-like member 4C and the inner core 8C will not be repeated here.

The inner core 8C is fixed or integral with a longitudinal connecting member extension or solid rod 42C. The rod 42C is integral or fixedly attached to the inner core 8C at a first end 43C thereof. The rod 42C is substantially coaxial with the inner core 8C and may be of any desired length, measured from the end 43C to an opposite end 44C, for attaching to one or more bone screw assemblies. The illustrated rod 42C is solid, but it is foreseen that it may be hollow. The rod 42C has a circular cross section, but may also be of other shapes including rectangular, square, and other polygonal and curved cross-sections. In the embodiment shown, the rod 42C includes a flat abutment surface 45C and an outer cylindrical surface 46C. In the illustrated embodiment, the cylindrical surface 46C has an outer diameter that is approximately the same as an outer diameter of the coil-like member 4C allowing for attachment of the same size polyaxial bone screw assembly 10 or 401. However, in certain embodiments, it may be desirable to have a more flexible rod 42C that may be of smaller diameter than the diameter of the coil-like member 4C, or in other instances, a slightly larger diameter, stiffer rod, each requiring a different sized bone screw receiver or receiver components. It is noted that a variety of hook and bone screw assemblies may cooperate with the solid rod surface 46C, including, but not limited to the polyaxial bone screw assembly 10B described herein and also the bone screw assembly described in detail in U.S. Pat. No. 6,716,214, incorporated by reference herein. The rod 42C is preferably of a length for secure attachment to at least one bone screw with at least one other cooperating bone screw assembly 10 or 401 being attached to the longitudinal connecting member at the coil-like member 4C, similar to what is illustrated and described herein with respect to the coil-like member 4 and shown in FIGS. 5-7 and 14-15. If a patient requires more rigid support along a substantial portion of the spine, the rod 42C may be of a longer length to cooperate and attach with two or more bone screws, each implanted on separate vertebra. Thus, an assembly 1C according to the invention may be used to provide protected movement of the spine along the coil-like member 4C and spinal fusion along the length of the rod 42C. It is foreseen that the rods 42C and 8C could be curvilinear in use.

Near the end 43C, the inner core 8C includes a cylindrical portion 48C of greater diameter than the remaining cylindrical surface of the core 8C, the portion 48C sized and shaped to provide a frictional press fit between the coil-like member 4C and the inner core 8C at only the portion 48C, when the inner core 8C is fully received in the coil-like member 4C. Thus, other than at the portion 48C, the coil-like member 4C is movable or slidable along the inner core 8C. Other structure may be used to attach the coil-like member 4C to the inner core 8C at only one location, such as the snap-on nob 48 and cooperating recess 68 of the assembly 1 previously described herein.

Figure 43:
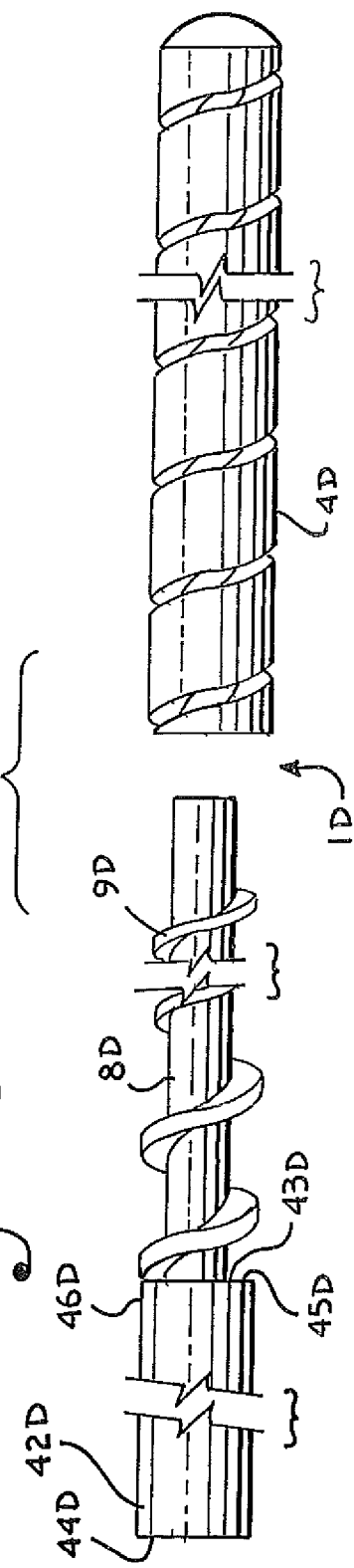
FIG. 43 is an exploded and partial front elevational view of a sixth embodiment of a dynamic fixation connecting member assembly according to the invention including an outer coil-like member a threaded inner cylindrical core and a solid rod integral with the threaded core.

With reference to FIG. 43, a sixth embodiment of a dynamic longitudinal connecting member assembly according to the invention, generally 1D, is substantially identical to the assembly 1A illustrated in FIGS. 10-13, with the exception that the stop 42A has been replaced by a solid connecting member or rod 42D. In particular, the assembly 1D includes an outer coil-like member 4D and an inner solid cylindrical core 8D having a helical thread 9D identical or substantially similar to the respective coil-like member 4A, the inner core 8A and the thread 9A of the connecting member assembly 1A previously described herein. Therefore details of the coil-like member 4D and the inner threaded core 8D will not be repeated here. Again, the connecting members could be curvilinear.

The inner core 8D is fixed or integral with a longitudinal connecting member extension illustrated as a solid rod 42D. The rod 42D is attached to the inner core 8D at a first end 43D thereof. In the embodiment shown, the rod 42D is substantially coaxial with the inner core 8D and may be of any desired length, measured from the end 43D to an opposite end 44D, for attaching to one or more bone screw assemblies. The illustrated rod 42D is solid, but it is foreseen that it may be hollow. The rod 42D has a circular cross section, but may also be of other shapes including rectangular, square, and other polygonal and/or curved cross-sections. In the embodiment shown, the rod 42D includes a flat abutment surface 45D and an outer cylindrical surface 46D. In the illustrated embodiment, the cylindrical surface 46D has an outer diameter that is approximately the same as an outer diameter of the coil-like member 4D allowing for attachment of the same size polyaxial bone screw assembly 10 or 401. However, in certain embodiments, it may be desirable to have a more flexible rod 42D that may be of smaller diameter than the diameter of the coil-like member 4D, or in other instances, a slightly larger diameter, stiffer rod, each requiring a different sized bone screw receiver or receiver components. It is noted that a variety of bone screw assemblies may cooperate with the solid rod surface 46D, including, but not limited to the polyaxial bone screw assembly 10B described herein and also the bone screw assembly described in detail in U.S. Pat. No. 6,716,214, incorporated by reference herein. The rod 42D is preferably of a length for secure attachment to at least one bone screw with at least one other cooperating bone screw assembly 10 or 401 being attached to the longitudinal connecting member at the coil-like member 4D, similar to what is illustrated and described herein with respect to the coil-like member 4A and shown, for example, in FIGS. 14-15 and 22. If a patient requires more rigid support along a substantial portion of the spine, the rod 42D may be of a longer length to cooperate and attach with two or more bone screws, each implanted on separate vertebra. Thus, an assembly 1D according to the invention may be used to provide protected movement of the spine along the coil-like member 4D and spinal fusion along the length of the rod 42D.

Figure 44:
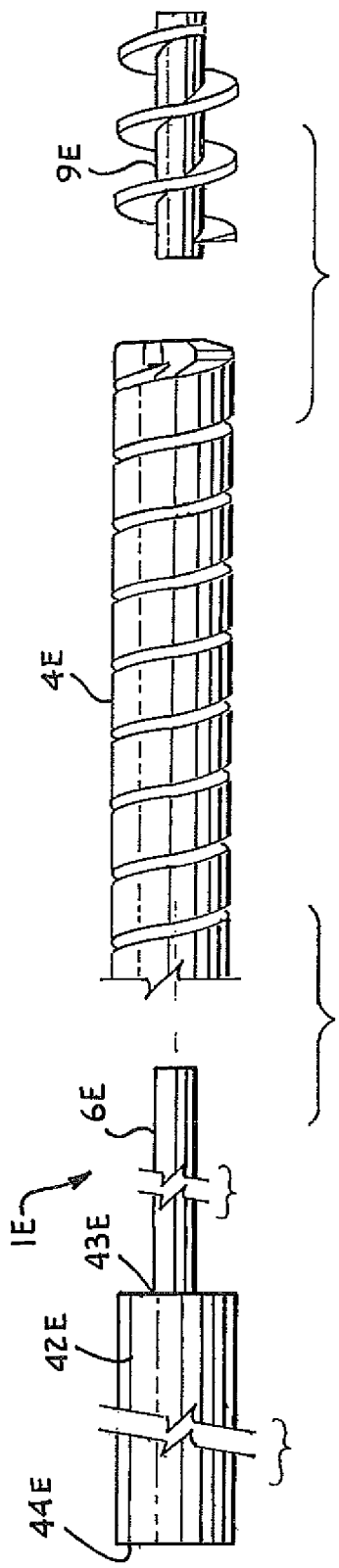
FIG. 44 is an exploded and partial front elevational view of a seventh embodiment of a dynamic fixation connecting member assembly according to the invention including an outer coil-like member, an inner cylindrical core, at least one threaded insert and a solid rod integral with the cylindrical core.

With reference to FIG. 44, a seventh embodiment of a dynamic longitudinal connecting member assembly according to the invention, generally 1E, is substantially identical to the assembly 1B illustrated in FIGS. 35-36, with the exception that a solid connecting member or rod 42E is integral or otherwise fixed to an inner cylindrical core 6E. In particular, the assembly 1E includes an outer coil-like member 4E, the inner core 6E, and at least one threaded insert 9E receivable on the core 6E, identical or substantially similar to the respective coil-like member 4B, the inner core 6B and the threaded inserts 9B of the connecting member assembly 1B previously described herein. Therefore details of the coil-like member 4E, core 6E and insert 9E will not be repeated here. Although not shown in FIG. 44, the core 6B may also include one or more fixed threaded support similar or identical to the support 8B previously described herein with respect to the core 6B.

The inner core 6E is fixed or integral with a longitudinal connecting member extension illustrated as a solid rod 42E near an end 43E thereof. The rod 42E is substantially coaxial with the inner core 6E and may be of any desired length, measured from the end 43E to an opposite end 44E, for attaching to one or more bone screw assemblies. The illustrated rod 42E is identical or substantially similar to the rods 42C and 42D described previously herein with the respective assemblies 1C and 1D.

It is to be understood that while certain forms of the present invention have been illustrated and described herein, it is not to be limited to the specific forms or arrangement of parts described and shown.

What is claimed is:

1. A pivotal bone anchor assembly for a securing a longitudinal connecting member to a bone, the pivotal bone anchor assembly comprising:
    a receiver having a lower body with a bottom opening and a pair of upwardly extending arms having opposed interior surfaces forming a receiver channel for receiving the longitudinal connecting member therebetween, the interior surfaces having a discontinuous splay preventing helically wound guide and advancement structure thereon and at least one retaining recess having a downwardly-facing top surface formed into the interior surfaces below the helically wound guide and advancement structure so as to extend only partially into at least one of the arms, and the lower body having a cavity in communication with the receiver channel and partially defined by a partially spherical-shaped internal surface adjacent the bottom opening;
    a shank having a body with an upper end portion and threaded lower portion for attachment to the bone, the upper end portion having a capture structure with a partially spherical-shaped lower surface that extends radially outward and axially upward from the threaded lower portion, the shank upper end portion being disposed within the receiver cavity; and
    an insert top loaded into the receiver channel after the shank upper end portion is disposed within the receiver cavity, the insert having a body with a connecting member-engaging upper surface, the insert being downwardly displaceable within the receiver channel, the body having a pair of upwardly-extending arms that have an upper portion projecting laterally near a top thereof, each laterally-projecting upper portion having a top surface thereon that is flush with a top surface of the upwardly-extending arms, at least one top surface being snapped under the at least one recess top surface to prevent upward movement of the insert when the insert is fully disposed within the receiver channel,
    wherein the partially spherical-shaped lower surface of the shank capture structure engages the partially spherical-shaped internal surface of the receiver cavity to provide pivotal motion of the shank with respect to the receiver.

2. The pivotal bone anchor assembly of claim 1, wherein the helically wound guide and advancement structure on the pair of receiver upwardly-extending arms is located entirely above the at least one retaining recess.

3. The pivotal bone anchor assembly of claim 1, wherein the helically wound guide and advancement structure is a helical flange.

4. The pivotal bone anchor assembly of claim 1, wherein the helically wound guide and advancement structure is a reverse angle thread.

5. The pivotal bone anchor assembly of claim 1, further comprising a closure structure having a continuous helically wound external structure directly engaging the helically wound guide and advancement structure of the receiver, the closure being rotatable at least 360 degrees within the receiver channel.

6. The pivotal bone anchor assembly of claim 5, wherein the closure structure further comprises a two-piece closure having a closed outer ring fastener with the continuous helically wound external thread positioned in the receiver channel above the connecting member, and an inner set screw extending from a bottom surface of the ring fastener, the inner set screw being configured to bias the connecting member toward and against the upper surface of the insert, the set screw being rotatable at least 360 degrees within the closed outer ring fastener.

7. The pivotal bone anchor assembly of claim 1, wherein the shank is cannulated.

8. The pivotal bone anchor assembly of claim 1, wherein the shank capture structure mates with a retainer having a partially spherical-shaped outer surface that conforms with a profile of the partially spherical-shaped lower surface of the shank capture structure and engages the partially spherical-shaped internal surface of the cavity.

9. The pivotal bone anchor assembly of claim 8, wherein a bottom surface of the insert engages the retainer.

10. The pivotal bone anchor assembly of claim 9, wherein at least a portion of the insert bottom surface includes a partially spherical-shaped inner surface that is complimentary with the retainer partially spherical-shaped outer surface.

11. The pivotal bone anchor assembly of claim 1, wherein a bottom surface of the insert is spaced from the upper end portion of the shank.

12. The pivotal bone anchor assembly of claim 1, wherein at least one laterally-projecting upper portion top surface on the insert remains within the retaining recess of the receiver when the pivotal bone anchor assembly is fully locked.

13. The pivotal bone anchor assembly of claim 1, wherein the insert top surfaces are sloped to engage with a complimentary sloped lower surface of a closure.

14. The pivotal bone anchor assembly of claim 1, wherein the insert has a bottom surface in compressive contact against a separate ring shaped structure engaged with the upper end portion of the shank, with the insert bottom surface remaining spaced from the shank upper end portion.

15. The pivotal bone anchor assembly of claim 14, wherein the separate ring shaped structure is positioned in the receiver before the insert.

16. The pivotal bone anchor assembly of claim 15, wherein the separate ring shaped structure is a locking member for locking the bone anchor assembly.

17. The pivotal bone anchor assembly of claim 1, wherein the receiver tool attachment grooves extend circumferentially from a front surface to a back surface of the receiver, and are located proximate a top surface of the receiver, the tool attachment grooves being positioned entirely above a top surface of the longitudinal connecting member locked within the receiver channel against the upper surface of the insert.

18. The pivotal bone anchor assembly of claim 17, wherein the tool attachment grooves have a lower downwardly sloping surface toward the receiver lower body.

19. The pivotal bone anchor assembly of claim 1, wherein the receiver channel blocks rotation between the receiver and the longitudinal connecting member when the longitudinal connecting member is positioned within the channel.

20. The pivotal bone anchor assembly of claim 1, wherein the insert is snapped into place with a tool.

21. The pivotal bone anchor assembly of claim 1, wherein the insert has a bottom with an outer circumferential rim comprising a continuous un-interrupted surface.

22. A pivotal bone anchor assembly for a securing a longitudinal connecting member to a bone, the pivotal bone anchor assembly comprising:
a receiver having a lower body with a bottom opening and a pair of upwardly extending arms with opposed interior surfaces forming a receiver channel for receiving the longitudinal connecting member therebetween, the interior surfaces having a discontinuous splay preventing helically wound guide and advancement structure thereon and at least one retaining recess having a downwardly-facing top surface formed into the interior surfaces entirely below the helically wound guide and advancement structure, and the lower body having a cavity in communication with the receiver channel and partially defined by a partially spherical-shaped internal seating surface adjacent the bottom opening;
a shank having a body with an integral upper end portion and threaded lower portion for attachment to the bone, the upper end portion having a capture structure with a partially spherical-shaped surface that extends radially outward and axially upward from the threaded lower portion; and
an insert top loaded into the receiver channel and having a body with a connecting member-engaging upper surface, the insert being downwardly displaceable within the receiver channel, the body having a pair of upwardly-extending arms with an upper portion projecting laterally near a top thereof, each laterally-projecting upper portion having a laterally-extending upper portion top surface thereon, at least one top surface being snapped under the at least one recess top surface to prevent upward movement of the insert when the insert is fully disposed within the receiver channel,
wherein the partially spherical-shaped surface of the shank upper end portion engages the partially spherical-shaped internal seating surface of the receiver cavity to provide pivotal motion of the shank with respect to the receiver, and
wherein the insert has a lower surface that remains spaced apart from the shank upper end portion.

23. A pivotal bone anchor assembly for a securing a longitudinal connecting member to a bone, the pivotal bone anchor assembly comprising:
a receiver having a lower body with a bottom opening and a pair of upwardly extending arms with opposed interior surfaces forming a receiver channel for receiving the longitudinal connecting member therebetween, the interior surfaces having a discontinuous helically wound guide and advancement structure thereon and at least one retaining recess having a downwardly-facing top surface formed into the interior surfaces entirely below the helically wound guide and advancement structure, and the lower body having a cavity in communication with the receiver channel and partially defined by a partially spherical-shaped internal surface adjacent the bottom opening;
a shank having a body with an upper end portion and threaded lower portion for attachment to the bone, the upper end portion having a partially spherical-shaped lower surface that extends radially outward and axially upward from the threaded lower portion, the partially spherical-shaped lower surface of the shank capture structure engaging the partially spherical-shaped internal surface of the receiver cavity to provide pivotal motion of the shank with respect to the receiver;
an insert disposable within the receiver channel and having a body with a connecting member-engaging upper surface, the insert being downwardly displaceable within the receiver channel, the body having a pair of upwardly-extending arms that have an upper portion projecting laterally near a top thereof, each laterally-projecting upper portion having a top surface thereon, at least one top surface being snapped under the at least one recess top surface to prevent upward movement of the insert when the insert is fully disposed within the receiver channel, and
a ring shaped structure with a central opening disposed intermediate the upper end portion of the shank and the insert and engaging the shank upper end portion above the partially spherical-shaped lower surface to space a bottom surface of the insert from the upper end portion of the shank,
wherein a downward compressive force applied to the insert is transmitted through the ring shaped structure to the shank upper end portion to frictionally engage the shank partially spherical-shaped lower surface with the cavity partially spherical-shaped internal surface to lock an orientation of the shank relative to the receiver.

24. The pivotal bone anchor assembly of claim 23, wherein the ring shaped structure is angularly fixed with respect to the receiver and angularly articulating with respect to the shank.

25. The pivotal bone anchor assembly of claim 24, wherein the ring shaped structure is a round collet.

26. The pivotal bone anchor assembly of claim 23, wherein the ring shaped structure articulates with respect to the receiver and is fixed with respect to the shank.

27. The pivotal bone anchor assembly of claim 23, wherein the ring shaped structure is a retainer that cooperates with the insert and the receiver to keep the shank within the receiver cavity.

28. The pivotal bone anchor assembly of claim 23, wherein the ring shaped structure prevents the shank upper end portion from exiting the receiver cavity through the bottom opening.

* * * * *

UNITED STATES PATENT AND TRADEMARK OFFICE
CERTIFICATE OF CORRECTION

PATENT NO. : 10,039,571 B2
APPLICATION NO. : 15/419740
DATED : August 7, 2018
INVENTOR(S) : Roger P. Jackson Page 1 of 1

It is certified that error appears in the above-identified patent and that said Letters Patent is hereby corrected as shown below:

In the Claims

- In Claim 10, Column 43, Line 1, delete "complimentary" and insert --complementary--, therefor.

- In Claim 13, Column 43, Line 12, delete "complimentary" and insert --complementary--, therefor.

- In Claim 17, Column 43, Line 27, delete "the" occurring before 'receiver tool attachment'.

Signed and Sealed this
Fourteenth Day of May, 2019

Andrei Iancu
*Director of the United States Patent and Trademark Office*